United States Patent
Lyerly et al.

(10) Patent No.: US 11,224,665 B2
(45) Date of Patent: Jan. 18, 2022

(54) MITOCHONDRIAL ANTIVIRAL SIGNALING (MAVS) PROTEIN COMPOSITIONS AND METHODS OF USING THE SAME

(71) Applicant: Duke University, Durham, NC (US)

(72) Inventors: Herbert K. Lyerly, Durham, NC (US); Zachary C. Hartman, Durham, NC (US)

(73) Assignee: Duke University, Durham, NC (US)

(*) Notice: Subject to any disclaimer, the term of this patent is extended or adjusted under 35 U.S.C. 154(b) by 923 days.

(21) Appl. No.: 15/726,099

(22) Filed: Oct. 5, 2017

(65) Prior Publication Data

US 2018/0092989 A1    Apr. 5, 2018

Related U.S. Application Data

(60) Provisional application No. 62/404,559, filed on Oct. 5, 2016.

(51) Int. Cl.

| | |
|---|---|
| *A61K 45/06* | (2006.01) |
| *C07K 14/47* | (2006.01) |
| *A61K 48/00* | (2006.01) |
| *C12N 15/86* | (2006.01) |
| *C07K 14/82* | (2006.01) |

(52) U.S. Cl.
CPC ............ *A61K 48/005* (2013.01); *A61K 45/06* (2013.01); *C07K 14/47* (2013.01); *C07K 14/4702* (2013.01); *C07K 14/82* (2013.01); *C12N 15/86* (2013.01); *C12N 2710/10343* (2013.01)

(58) Field of Classification Search
CPC ... A61K 48/005; C07K 14/47; C07K 14/4702
See application file for complete search history.

(56) References Cited

U.S. PATENT DOCUMENTS

| | | |
|---|---|---|
| 6,734,172 B2 | 5/2004 | Scholler et al. |
| 8,445,268 B2 | 5/2013 | Lee et al. |
| 8,846,080 B2 | 9/2014 | Biemans et al. |
| 9,216,229 B2 | 12/2015 | Brown et al. |
| 9,226,959 B2 | 1/2016 | Kramps et al. |
| 9,956,276 B2 | 5/2018 | Lyerly et al. |
| 2003/0143568 A1 | 7/2003 | Singer et al. |
| 2003/0228606 A1 | 12/2003 | Tatarewicz et al. |
| 2003/0232350 A1 | 12/2003 | Afar et al. |
| 2004/0253606 A1 | 12/2004 | Aziz et al. |
| 2005/0266409 A1 | 12/2005 | Brown et al. |
| 2008/0057064 A1 | 3/2008 | Zhou |
| 2009/0214518 A1 | 8/2009 | Buckanovich et al. |
| 2010/0055093 A1 | 3/2010 | Shepard et al. |
| 2010/0279399 A1 | 11/2010 | Robins et al. |
| 2011/0281748 A1 | 11/2011 | Singh et al. |
| 2012/0014984 A1 | 1/2012 | Shahabi |
| 2014/0017259 A1 | 1/2014 | Aurisicchio et al. |
| 2014/0221329 A1 | 8/2014 | Cronin et al. |
| 2015/0047065 A1 | 2/2015 | Brack et al. |
| 2015/0258099 A1 | 9/2015 | Hager et al. |
| 2020/0216506 A1* | 7/2020 | Kagan ...................... C12N 9/12 |
| 2020/0377551 A1* | 12/2020 | Lin ..................... C07K 14/4702 |

FOREIGN PATENT DOCUMENTS

| | | | |
|---|---|---|---|
| WO | WO 2003/080835 | 10/2003 | |
| WO | WO-2004111088 A2 * | 12/2004 | ........... C07K 14/515 |
| WO | WO 2011/060260 | 5/2011 | |
| WO | WO 2011/146568 | 11/2011 | |
| WO | WO 2011/154863 | 12/2011 | |
| WO | WO 2012/125864 | 9/2012 | |
| WO | WO 2016/007499 | 1/2016 | |
| WO | WO 2016/007504 | 1/2016 | |
| WO | WO 2017/120576 | 7/2017 | |

OTHER PUBLICATIONS

Napolitani, G et al. "Selected Toll-like receptor agonist combinations synergistically trigger a T helper type 1-polarizing program in dendritic cells." (2005) Nat Immunol 8:769-76.
Nitta, T., et al., "Preliminary trial of specific targeting therapy against malignant glioma" Lancet 355:368-371 (1990).
Norton, J.A., et al. "Inhibition of host signal transducer and activator of transcription factor 6 results in cure with cyclophosphamide and interleukin 12 immunotherapy." (2006) Ann Surg Oncol 13:118-24.
O'Neil, L.A., et al. "The family of five: TIR-domain-containing adaptors in toll-like receptor signaling." (2007) Nat Rev Immunol 7:353-64.
O'Neil, L.A., et al. "Therapeutic targeting of toll-like receptors for infectious and inflammatory diseases and cnacer." (2009) Pharmacol Rev 61:177-97.
O'Neil, L.A. "How toll-like receptors signal: what we know and what we don't know." (2006) Curr Opin Immunol 18:3-9.
Osada, T., et al. "Vaccination targeting human HER3 alters the phenotype of infiltrating T cells and respones to immune checkpoint inhibition." (2017). OncoImmunology 0(0).
Palm, N.W., et al. "Pattern recognition receptors and control of adaptive immunity." (2009) Immunol Rev. 227:221-33.
Pederson, M.W., et al. "Sym004: a novel synergistic anti-epidermal growth factor receptor antibody mixture with superior anticancer efficacy." (2010) Cancer Res 70:588-97.
Puel, A., et al. "Heritable defects of the human TLR signaling pathways." (2005) J Endotoxin Res 11:220-4.
Pulaski, B.A., et al. "Reduction of established spontaneous mammary carcinoma metastases following immunotherapy with major histocompatibility complex class II and B7.1 cell-based tumor vaccines." (1998) Cancer Res. 58:1486-93.
Rakoff-Nahoum, S. & Medzhitov, R. "Toll-like receptors and cancer." (2009) Nat Rev 9:57-63.
Renard, V. et al., "HER-2 DNA and Protein Vaccines Containing Potent Th Cell Epitopes Induce Distinct Protective and Therapeutic Antitumor Responses in HER-2 Transgenic Mice" (2003) J Immunol 171(3): 1588-1595.

(Continued)

*Primary Examiner* — Antonio Galisteo Gonzalez
(74) *Attorney, Agent, or Firm* — Quarles & Brady LLP

(57) ABSTRACT

The invention generally relates to compositions and methods for preventing and treating cancer. More specifically, the invention relates to MAVS compositions and their use in cancer therapeutics that may be used to treat various cancers alone or in combination with other anti-cancer therapeutic agents.

13 Claims, 52 Drawing Sheets

Specification includes a Sequence Listing.

(56) References Cited

OTHER PUBLICATIONS

Ren, X.R., et al. "Polyclonal Her2-specific antibodies induced by vaccination mediate receptor internalization and degradation in tumor cells" (2012) Breast cancer research 14: R89.
Rosenberg, S.A., et al. "Adoptive cell transfer: a clinical path to effective cancer immunotherapy". Nat. Rev. Cancer 8 (4): 299-308 (2008).
Roskoski, R. Jr. "The ErbB/HER family of protein-tyrosine kinases and cancer". Pharmacological research : the official journal of the Italian Pharmacological Society. 2014;79:34-74.
Sakai, K., et al. "A novel HER dimerization inhibitor, inhibits the growth of human lung cancer cells mediated by the HER3 signaling pathway". Cancer Sci. 2007;98(9):1498-503.
Salazar-Mather, T.P., et al. "A chemokine-to-cytokine-to-chemokine cascade critical in antiviral defense." (2000) J Clin Invest 105:985-93.
Schoeberl, B., et al. "An ErbB3 Antibody, MM-121, Is Active in Cancers with Ligand-Dependent Activation" (2010) Cancer Research: 70(6): 2485-2494.
Shin, D.S. & Ribas, A. "The evolution of checkpoint blockade as a cancer therapy: what's here, what's next?" Curr Opin Immunol. 2015;33:23-35.
Soares, K.C., et al. "PD-1/PD-L1 blockade together with vaccine therapy facilitates effector T-cell infiltration into pancreatic tumors". J Immunother. 2015;38(1):1-11.
Tabi, Z. & Man, S. "Challenges for cancer vaccine development." (2006) Adv Drug Deliv Rev 58:902-15.
Takeshita, F., et al. "Toll-like receptor adaptor molecules enhaced DNA-raised adaptive immune responses against influenza and tumors through activation of innate immunity." (2006) J Virol 80:6218-24.
Tanaka, T. et al., "Efficient generation of antibodies to oncoproteins by using synthetic peptide antigens," (1985) Proc. Natl. Acad. Sci. USA 82:3400-3404.
Tiriveedhi, V., et al. "Safety and preliminary evidence of biologic efficacy of a mammaglobin-a DNA vaccine in patients with stable metastatic breast cancer". Clinical cancer research : an official journal of the American Association for Cancer Research. 2014;20(23):5964-75.
Topalian, S.L., et al. "Immune checkpoint blockade: a common denominator approach to cancer therapy". Cancer Cell. 2015;27(4):450-61.
Van Elsas, A., et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation". J Exp Med. 1999;190(3):355-66.
Yoo, J.Y., et al., "Downregulation of ErbB3 Expression by Adenovirus Expressing ErbB3 Specific shRNA Enhances Antitumor Efficacy through Apoptosis Induction" (2009) Molecular Therapy: 17(Suppl. 1): S106.
Yuan, J., et al., "CTLA-4 blockade increases antigen-specific CD8(+) T cells in prevaccinated patients with melanoma: three cases" (2011) Cancer Immunol Immunother, 60(8): 1137-1146.
Yu, P., et al. "Targeting the primary tumor to generate CTL for the effective eradication of spontaneous metastases." (2007) J Immunol 179:1960-8.
Zitvogel, L., et al. "The anticancer immune response: indispensable for therapeutic success?" (2008) 118:1991-2001.
Hartman et al.; AACR Tumor Immunology and Immunotherapy Special Conference. Abstract: Submission-Intralesional vaccination with Ad-MAVS alters the immunosuppressive tumor microenvironment and elicits robust anti-tumor immunity in non-immunogenic cancers. Oct. 20-23, 2016 Boston MA.
Agus, D.B., et al. "Targeting ligand-activated ErbB2 signaling inhibits breast and prostate tumor growth." (2002) 2:127-37.
Amalfitano, A., et al. "Production and characterization of improved adenovirus vectors with the E1, E2b, and E3 genes deleted" (1998) J Virol. 72(2):926-33.

Amin, D.N., et al. "The role of HER3, the unpretentious emmber of the HER family, in cancer biology and cancer therapuetics." (2010) Semin Cell Dev Biol 2010:8.
Arteaga, C. et al. "Treatment of HER2-positive breast cancer: current status and future perspectives" (2012) Nature Reviews Clinical Oncology, 9: 16-32.
Atkins, M.B., et al. "Phase I evaluation of intravenous recombinant human interleukin 12 in patients with advanced malignancies." (1997) Clin Cancer Res 3:409-17.
Ben-Kasus, T. et al. "Persistent elimination of ErbB-2/HER2-overexpressing tumors using combinations of monoclonal antibodies: relevance of receptor endocytosis." (2009) Proc Natl Acad Sci USA 106:3294-99.
Binder, D.C., et al. "Antigen-specific bacterial vaccine combined with anti-PD-L1 rescues dysfunctional endogenous T cells to reject long-established cancer" (2013) Cancer immunology research 1(2):123-33.
Blattman, J.N., et al. "Cancer immunotherapy: a treatment for the masses." (2004) Science 305:200-5.
Cai., Z., et al. "Targeting erbB receptors" 2010 Seminars in cell & developmental biology 21(9):961-6.
Campbell, M.R., et al. "HER3 comes of age: new insights into its functions and role in signaling, tumor biology, and cancer therapy." Clin cancer Res (2010) 16:1373-83.
Clay, T. et al., "Polyclonal Immune Responses to Antigens Associated With Cancer Signaling Pathways and New Strategies to Enhance Cancer Vaccines" (2011) Immunolo Res 49(0): 235-247.
Drake, C.G., et al. Mechanisms of immune evasion by tumors. (2006) Adv Immunol 90:51-81.
Dranoff, G. "Cytokines in cancer pathogenesis and cancer therapy." (2004) Nat Rev Cancer 4:11-22.
Eager, R., et al. "GM-CSFF gene-transduced tumor vaccines." (2005) Mol Ther. 12:18-27.
Emens, L.A., et al. "Abstract PD1-6: Inhibition of PD-L1 by MPDL3280A leads to clinical activity in patients with metastatic triple-negative breast cancer" (2015) Cancer Res. 75(9 Supplement):PD1-6-PD1-6.
Fourcade, J., et al. "PD-1 and Tim-3 regulate the expansion of tumor antigen-specific CD8(+) T cells induced by melanoma vaccines" (2014) Cancer Res. 74(4):1045-55.
Friedman, L.M., et al. "Synergistic down-regulation of receptor tyrosine kinase by combinations of mAbs: implications for cancer immunotherapy." (2005) Proc Natl Acad Sci USA 102:1915-20.
Fu, J. et al., "Preclinical evidence that PD1 blockade cooperates with cancer vaccine TEGVAX to elicit regression of established tumors" (2014) Cancer Res, 74(15): 4042-4052.
Gala, K., & Chandarlapaty, S. "Molecular pathways: HER3 targeted therapy" (2014) Clin Cancer Res 20(6):1410-6.
Gallo, P. et al., "Xenogenic Immunization in Mice Using HER2 DNA Delivered by an Adenoviral Vector" (2005) Int. J. Cancer 113(1): 67-77.
Goldman, B., et al. "The cancer vaccine roller coaster." (2009) Nat Biotechnol 27:129-39.
Grupp, S., et al. Chimeric antigen receptor-modified T cells for acute lymphoid leukemia. New England J. Med. 368:1509-18, (2013).
Hartman, Z., et al. "An Adenoviral vaccine encoding full-length inactivated human Her2 exhibits potent immunogenicity and enhanced therapeutic efficacy without oncogenicity" (2010) Clin Cancer Res 16(5): 1466-1477.
Hartman, Z., et al. "Adenoviral infection induces a multi-faceted innate cellular immune response that is mediated by the toll-like receptor pathway in A549 cells." (2007) Virology 358:3570-72.
Hartman, Z., et al. "Adenovirus infection triggers a rapid, MyD88-regulated transcriptome response critical to acute-phase and adaptive immune resopnses in vivo." (2007) J Virol 81:1796.
Hartman, Z., et al. "Ligand-independent TLR signals generated by ectopic overexpression of MyD88 generate local and systemic anti-tumor immunity" (2010) Cancer Res 70(18): 7209-7220.
Hartman, Z., et al. "Growth of triple-negative breast cancer cells relies upon coordinate autocrine expression of the proinflammatory cytokines IL-6 and IL-8" (2013) Cancer Res 73(11): 3470-3480.

(56) References Cited

OTHER PUBLICATIONS

Hartman, Z., et al. "Increasing vaccine potency through exosome antigen targeting" (2011) Vaccine Nov. 21;29(50):9361-7.
He, T.C., et al. "A simplified system for generating recombinant adenoviruses." (1998) Proc Natl Acad Sci USA 95:2509-14.
Hsieh, A.C. & Moasser, M.M. "Targeting HER proteins in cancer therapy and the role of the non-target HER3" (2007) Br J Cancer. 97(4):453-7.
Huang, B., et al. "Toll-like receptors on tumor cells facilitate evasion of immune surveillance." (2005) Cancer Res 65:5009-14.
Ignatiadis, M. & Sotiriou, C. "Luminal breast cancer: from biology to treatment" (2013) Nature Rev Clin Oncol 10, 494-506.
Kanzler, H., et al. "Therapeutic targeting of innate immunity with Toll-like receptor agonists and antagonists." (2007) Nat Med 13:552-9.
Karyampudi, L., et al. "Accumulation of memory precursor CD8 T cells in regressing tumors following combination therapy with vaccine and anti-PD-1 antibody" 2014 Cancer Res 74(11):2974-85.
Kershaw, M.H. et al., "Gene-engineered T cells as a superior adjuvant therapy for metastatic cancer" (2004) J Immunol 173(3): 2143-2150.
Kol, A., et al. "HER3, serious partner in crime: therapeutic approaches and potential biomarkers for effect of HER3-targeting". Pharmacol Ther. 2014;143(1):1-11.
Ku, C.L., et al. "Inherited disorders of human toll-like receptor signaling: immunological implications." (2005) Immunol Rev 203:10-20.
Laheru, D.A., et al. "Genes to vaccines for immunotherapy: how the molecular biology revolution has influenced cancer immunology." (2005) Mol Cancer Ther 4:1645-52.
Lee-Hoeflich, S.T., et al. "A central role for HER3 in HER2-amplified breast cancer: implications for targeted therapy." (2008) Cancer Res 68:5878-87.
Li, B., et al. "Anti-programmed death-1 synergizes with granulocyte macrophage colony-stimulating factor—secreting tumor cell immunotherapy providing therapeutic benefit to mice with established tumors". Clin Cancer Res. 2009;15(5):1623-34.
Liddy, N., et al., Monoclonal TCR-redirected tumor cell killing. Nature Med. 18:980-7 (2012).
Luo, J., et al. "A protocol for rapid generation of recombinant adenoviruses using the AdEasy system" (2007) Nature Protocols 2:1236.
Makhija, S., et al. "clinical activity of gemcitabine plus pertuzumab in platinum-resistant ovarian cancer, fallopian tube cancer, or primary peritoneal cancer." (2010) J Clin Oncol 28:1215-23.
Mazzolini, G., et al. "Genetic heterogeneity in the toxicity to systemic adenoviral gene transfer of interleukin-12." (2001) Gene Ther 8:259-67.
Medzhitov, R., et al. "MyD88 is an adaptor protein in the hToll/IL-1 receptor family signaling pathways." (1998) Mol Cell 2:253-8.
Morse, M.A., et al. Synergism from combined immunologic and pharmacologic inhibition of HER2 in vivo. (2010) Int J Cancer 126:2893-903.
Nabholtz, J.M., et al., "Anastrozole is superior to tamoxifen as first-line therapy for advanced breast cancer in postmenopausal women: results of a North American multicenter randomized trial. Arimidex Study Group" (2000) J Clin Oncol 18(22): 3758-3767.
Nanda, R., et al. Pembrolizumab in Patients With Advanced Triple-Negative Breast Cancer: Phase Ib Keynote-012 Study. J Clin Oncol. 2016;34(21):2460-7.

* cited by examiner

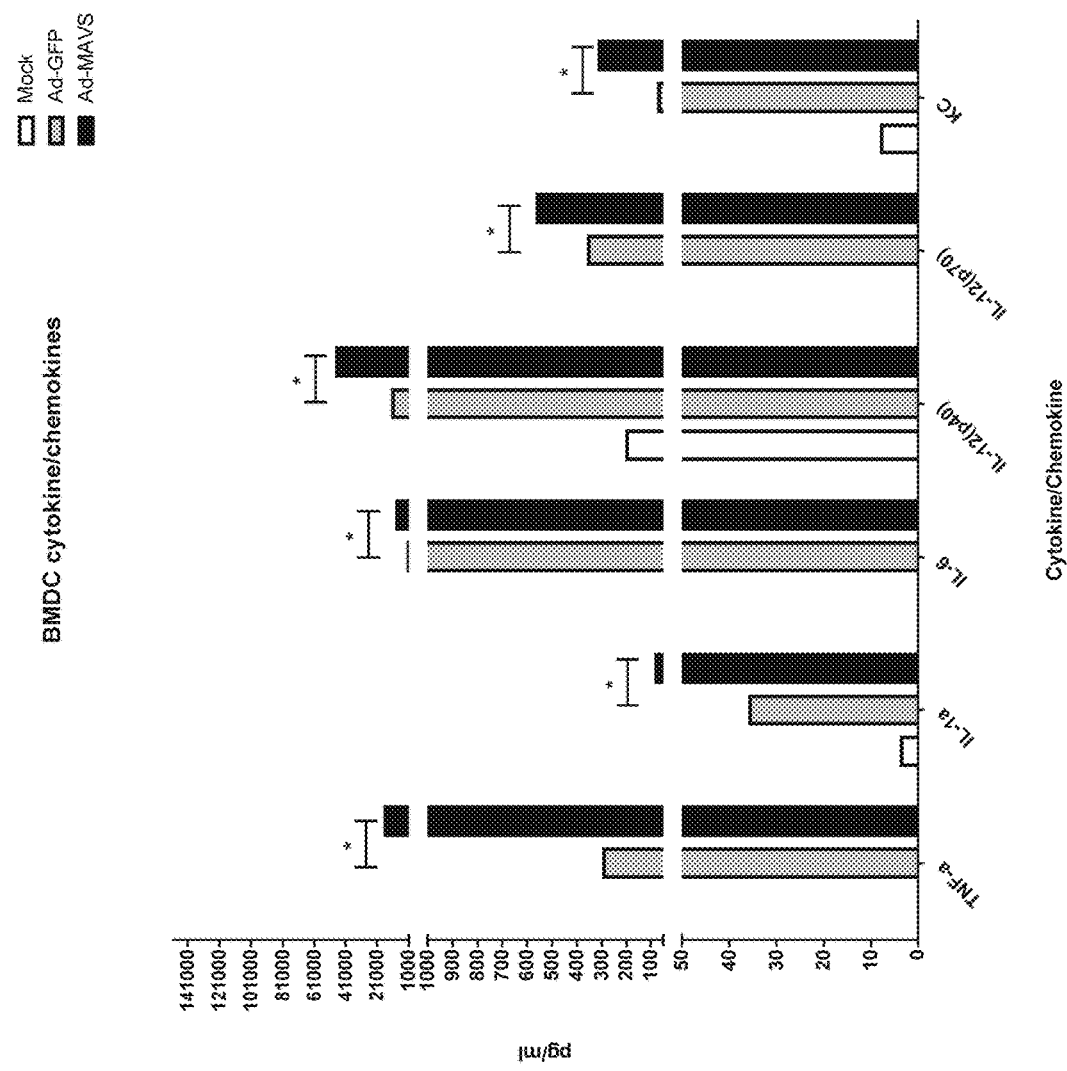

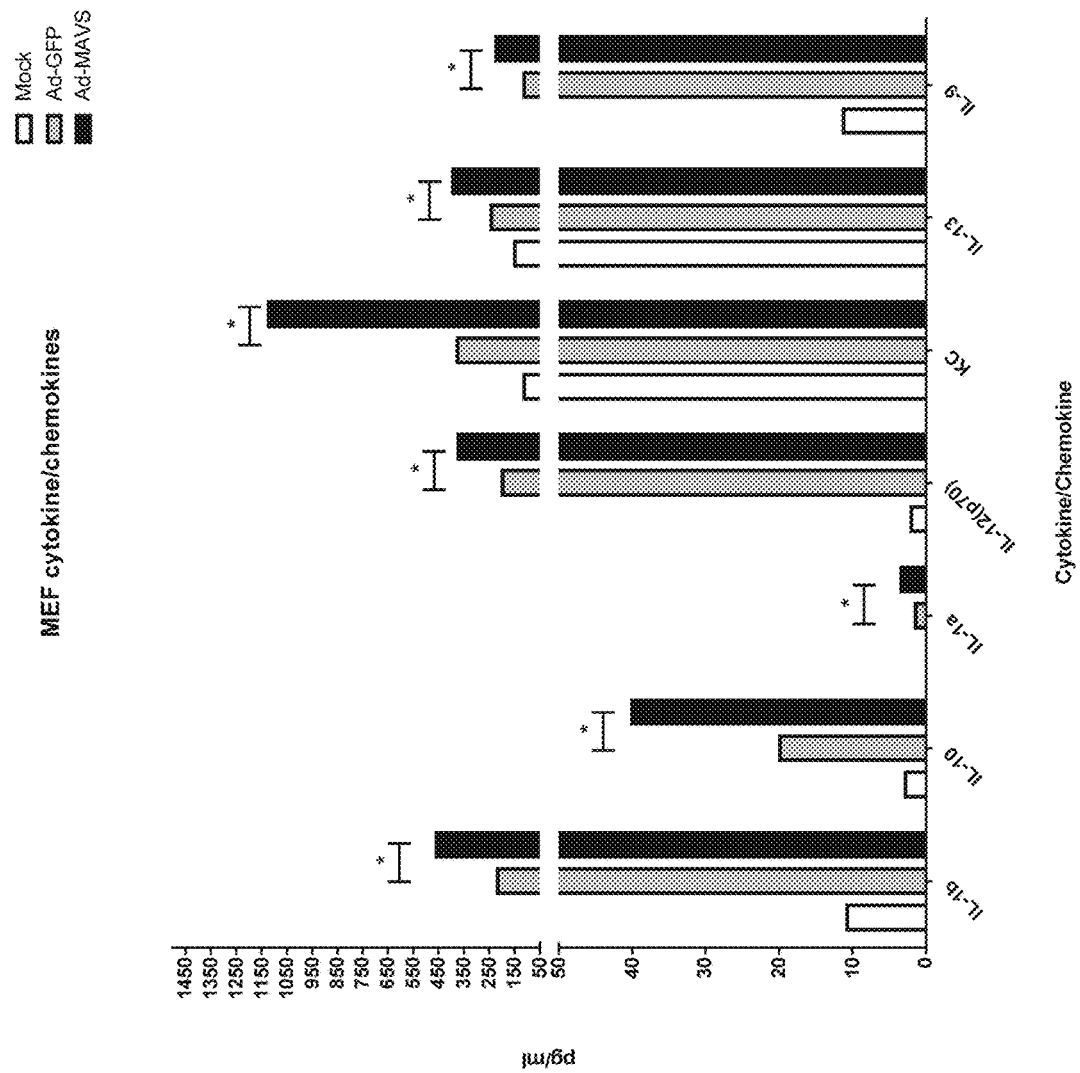

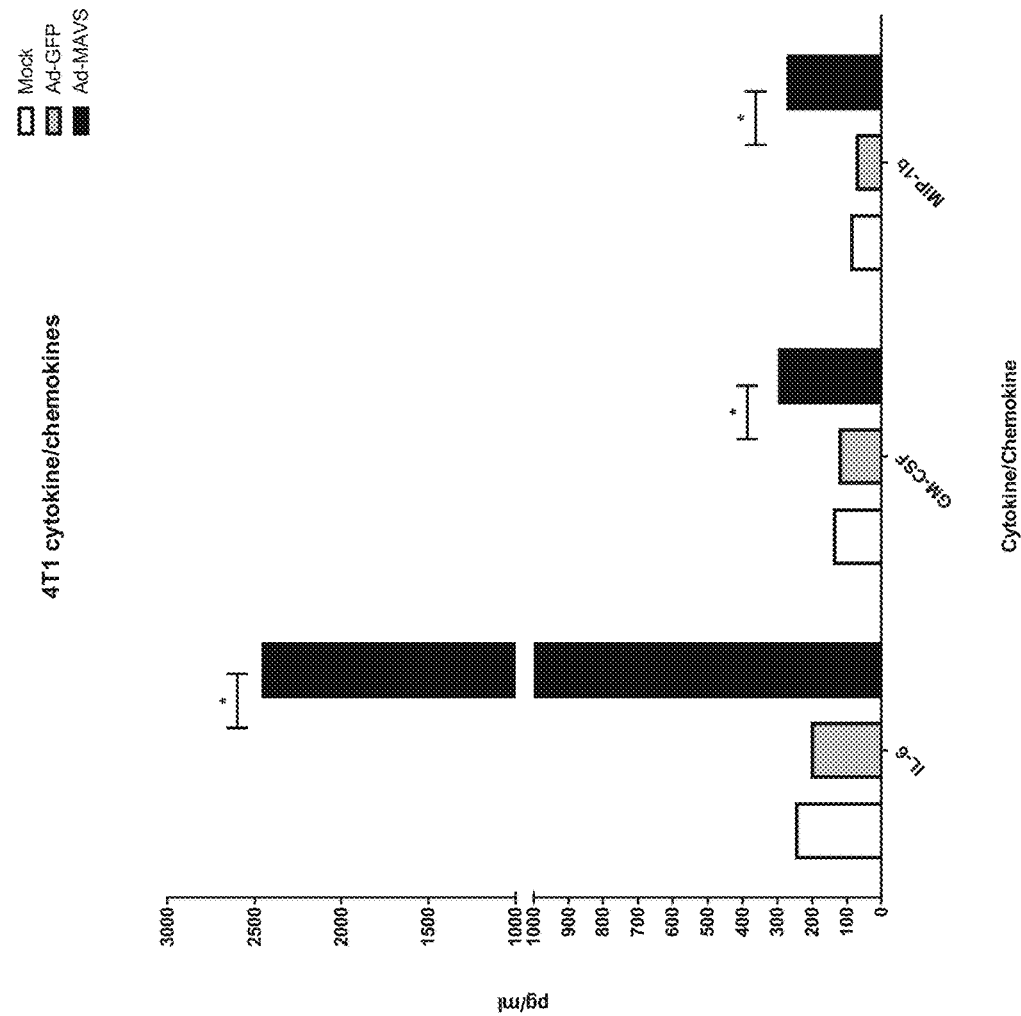

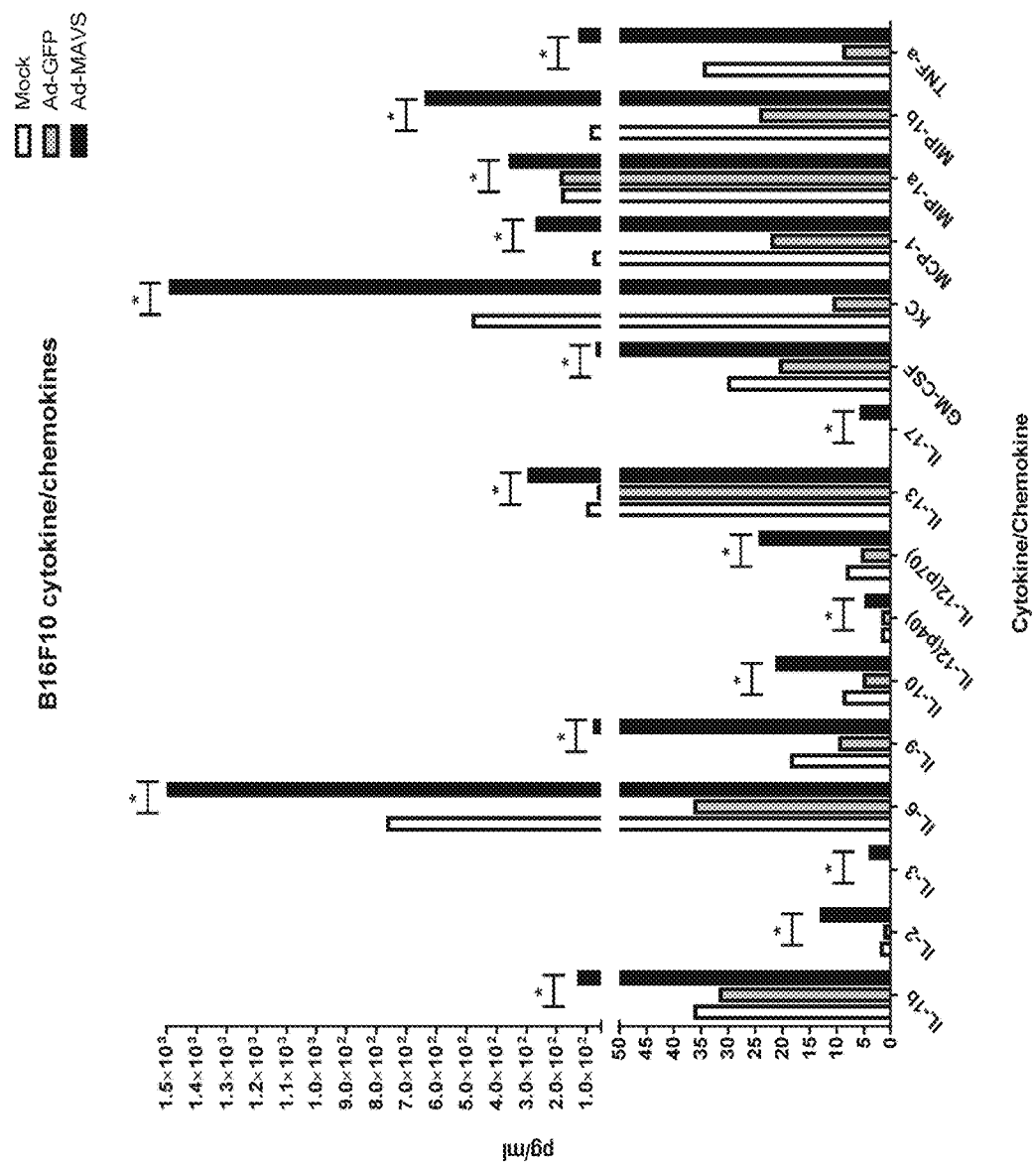

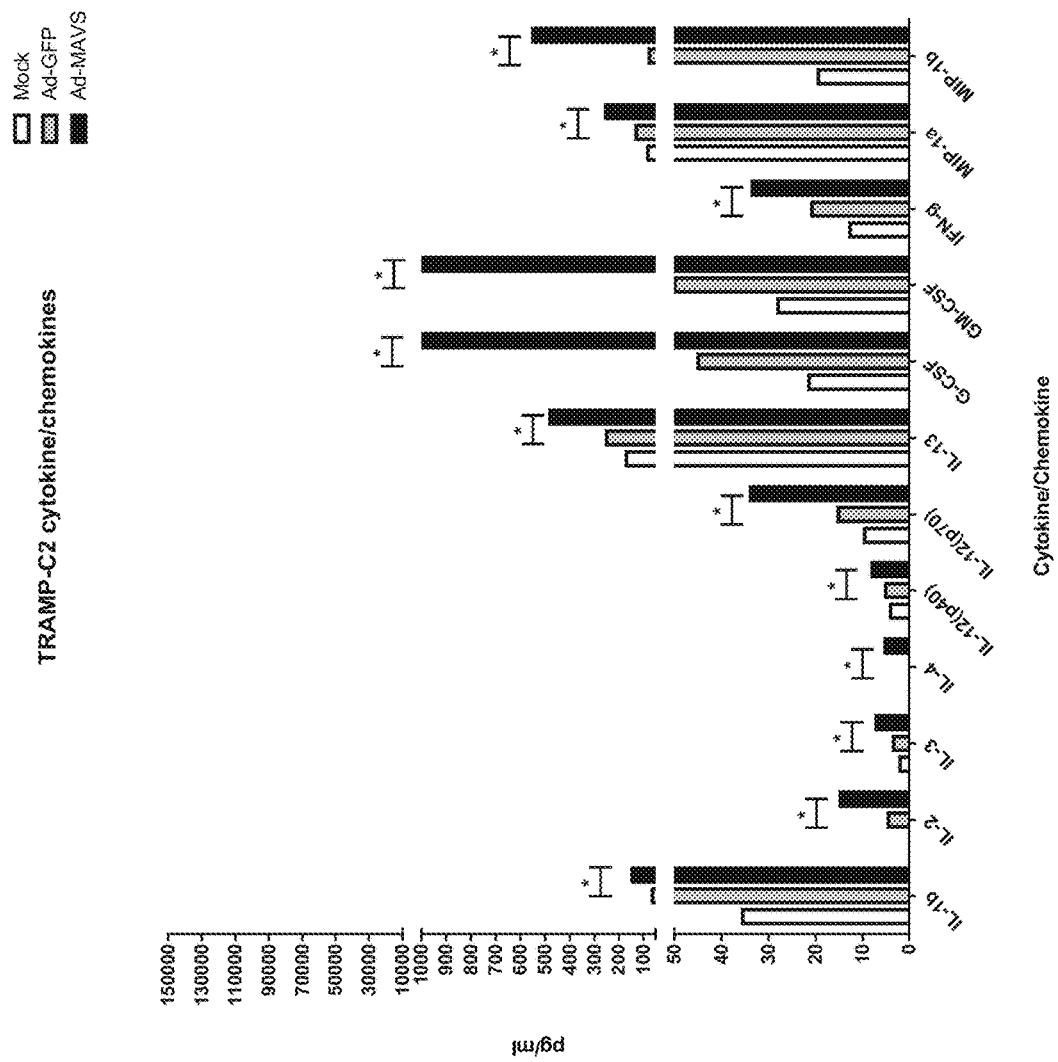

Figs. 2C and 2D
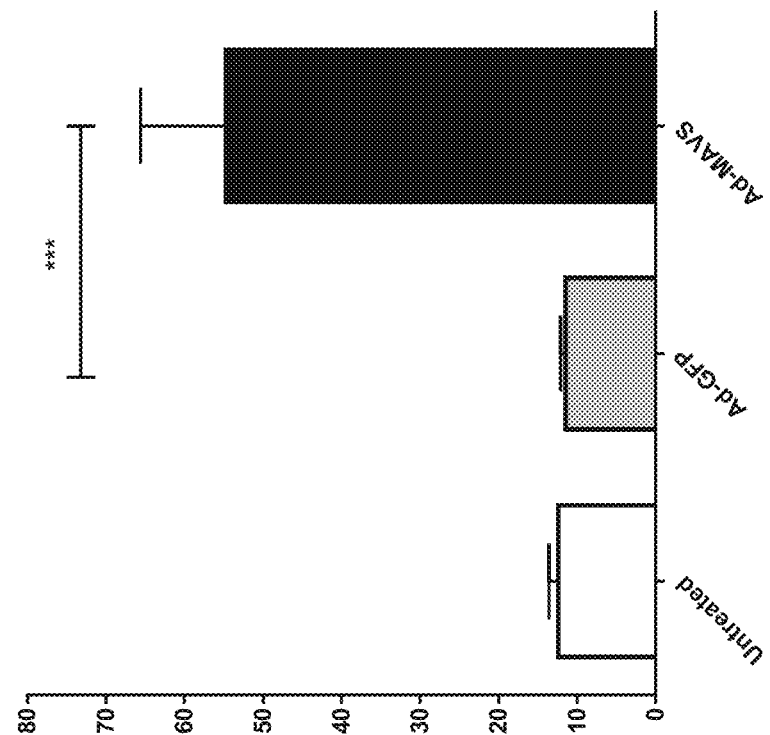
Fig. 2D
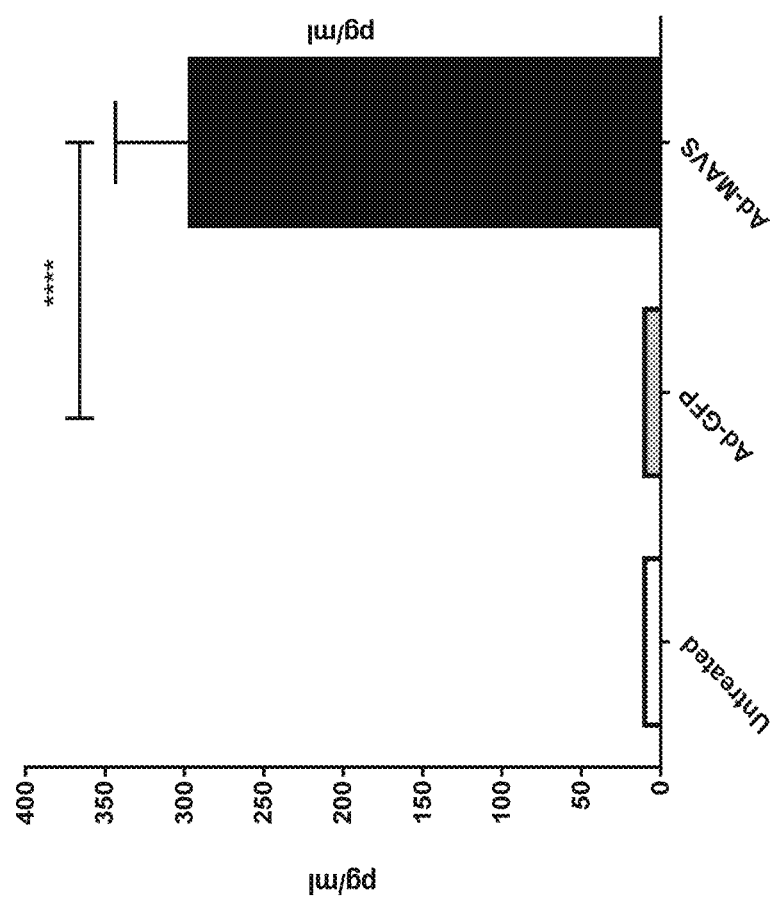
Fig. 2C

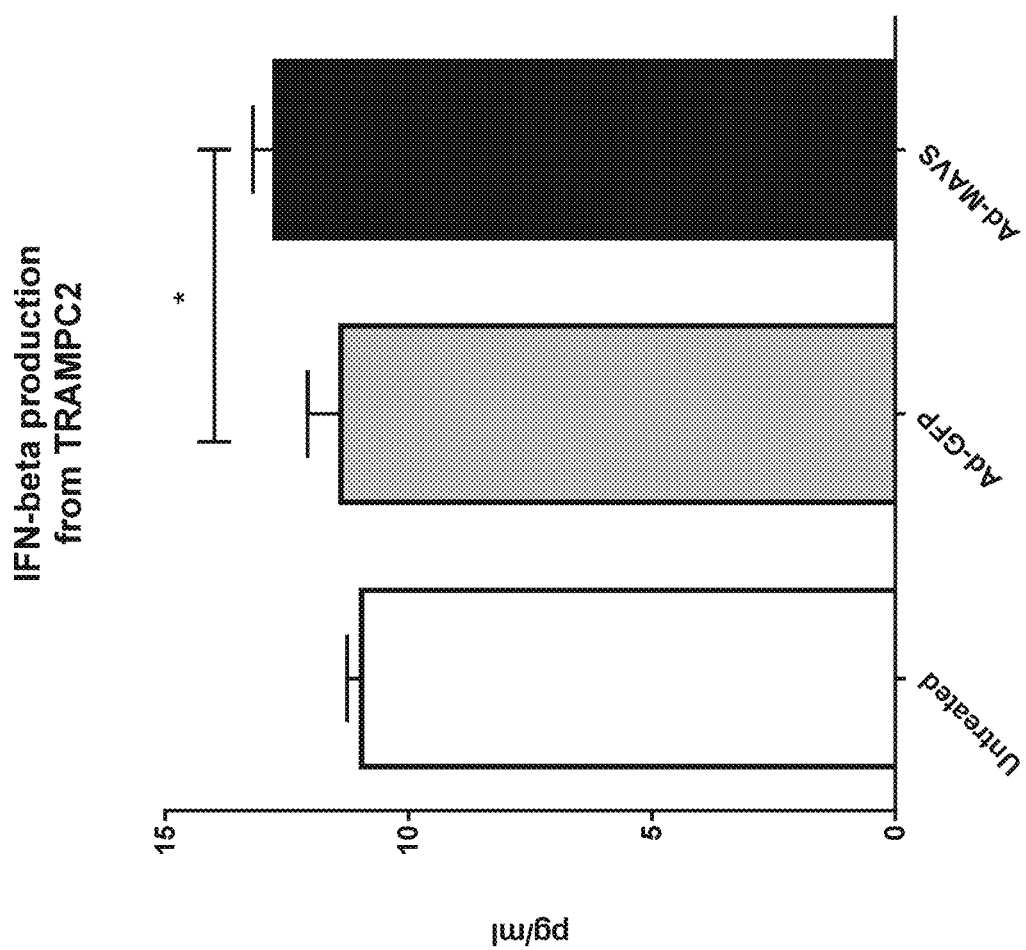

Figs 3A-3B
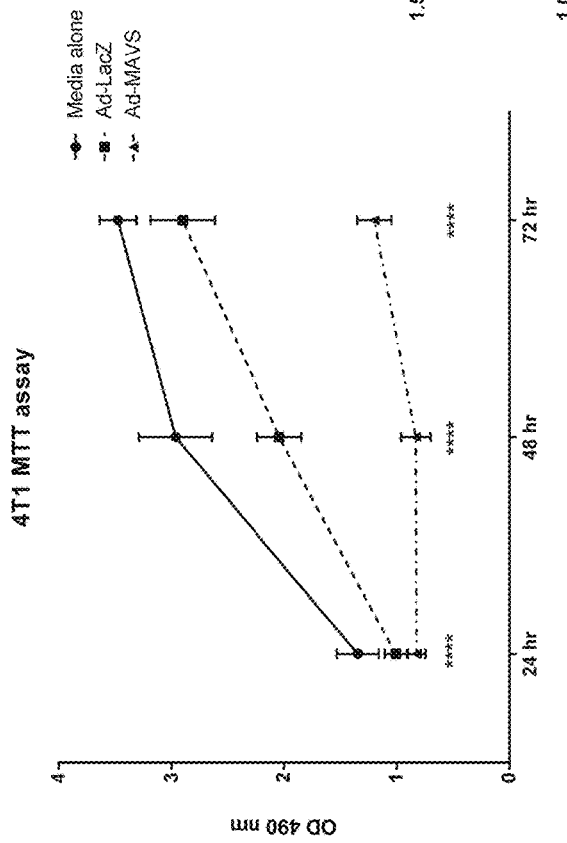
Fig. 3A
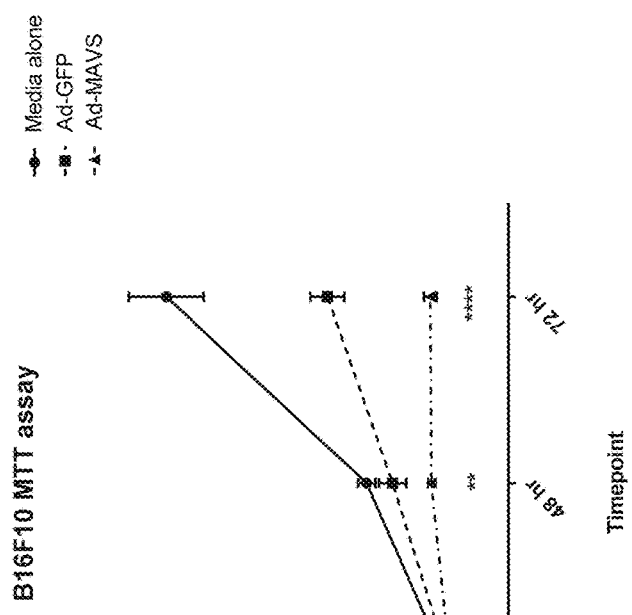
Fig. 3B

Figs 3C-3D
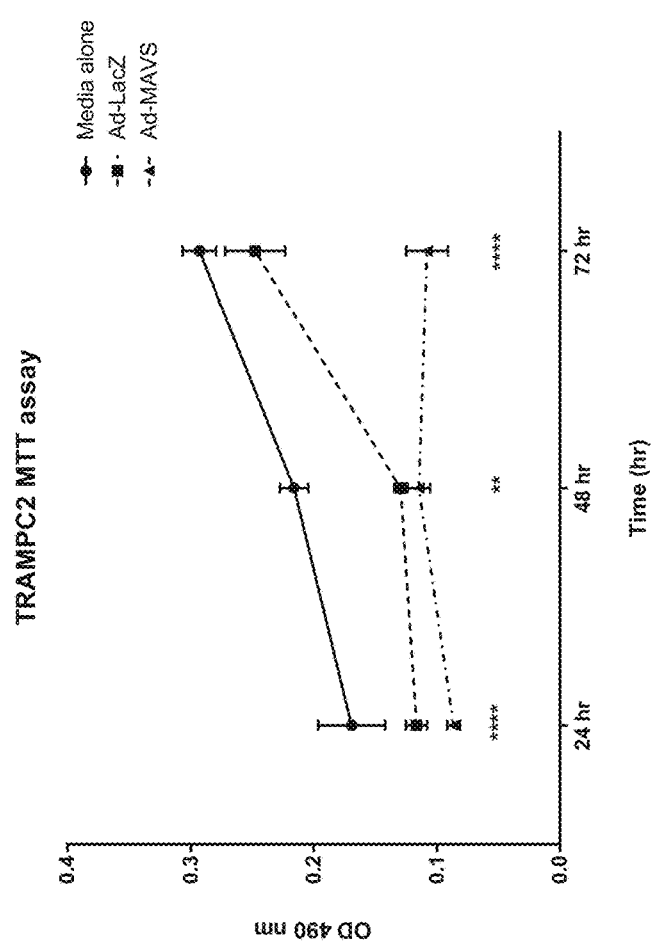
Fig. 3D
TRAMPC2 MTT assay
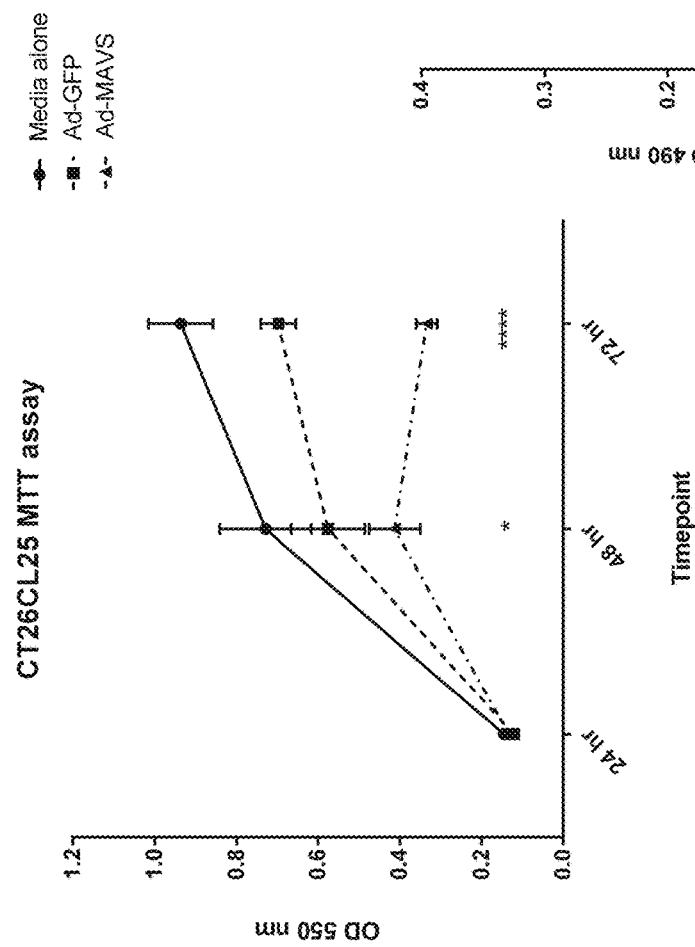
Fig. 3C
CT26CL25 MTT assay

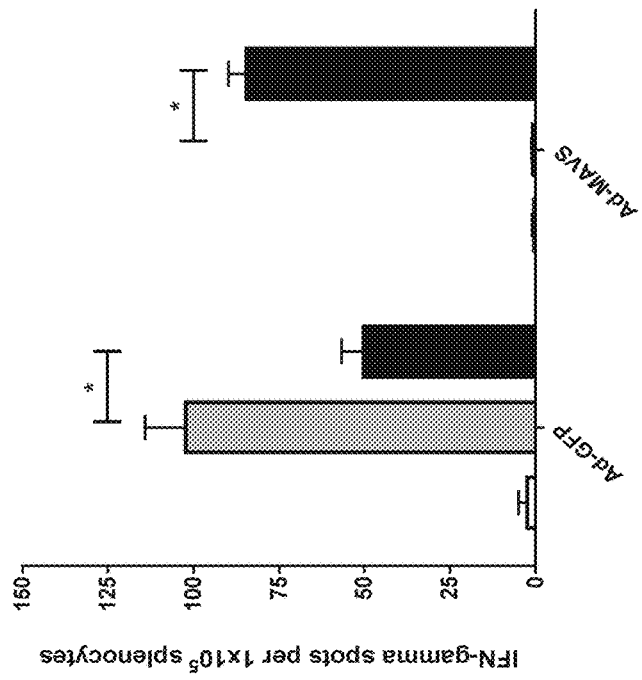
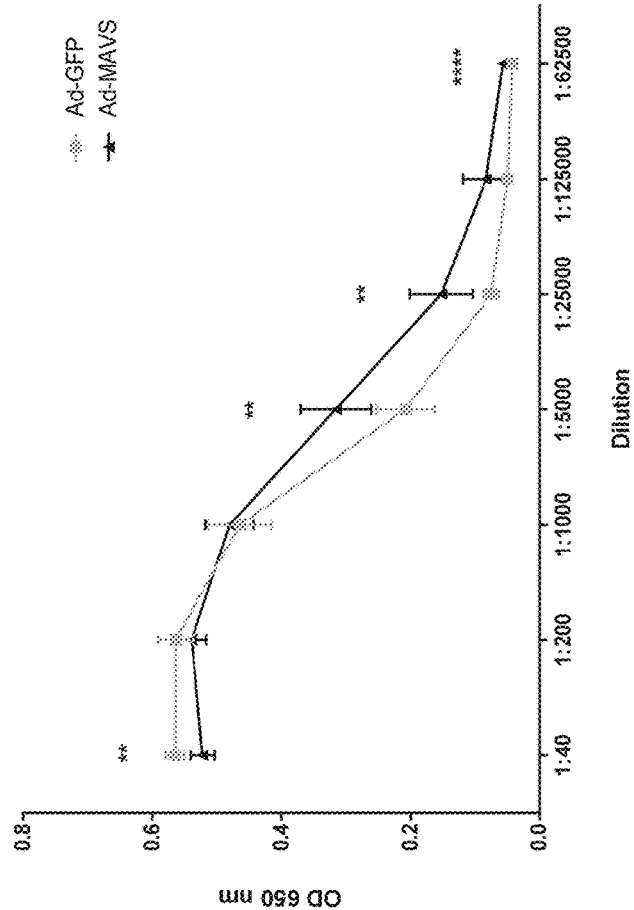
Fig. 4A
Fig. 4B

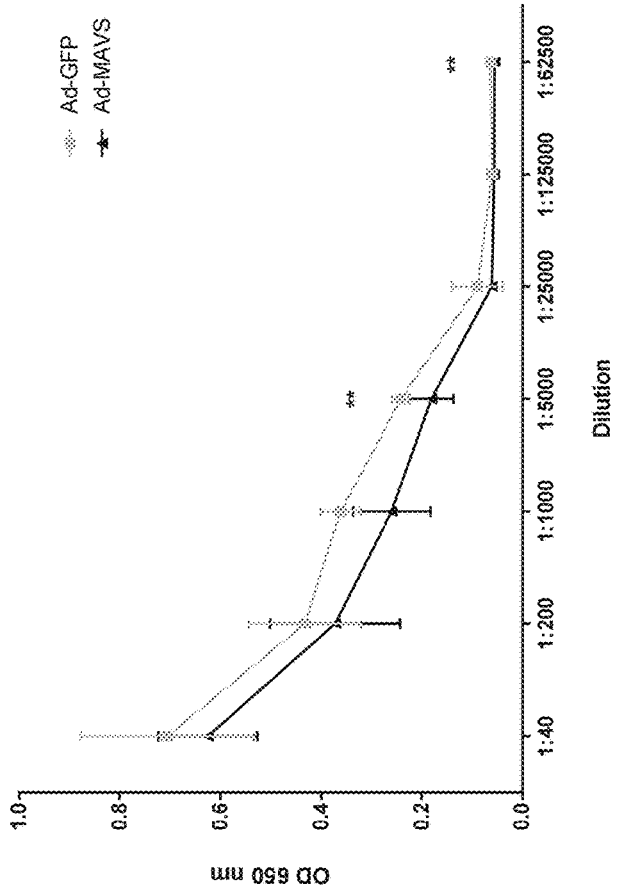
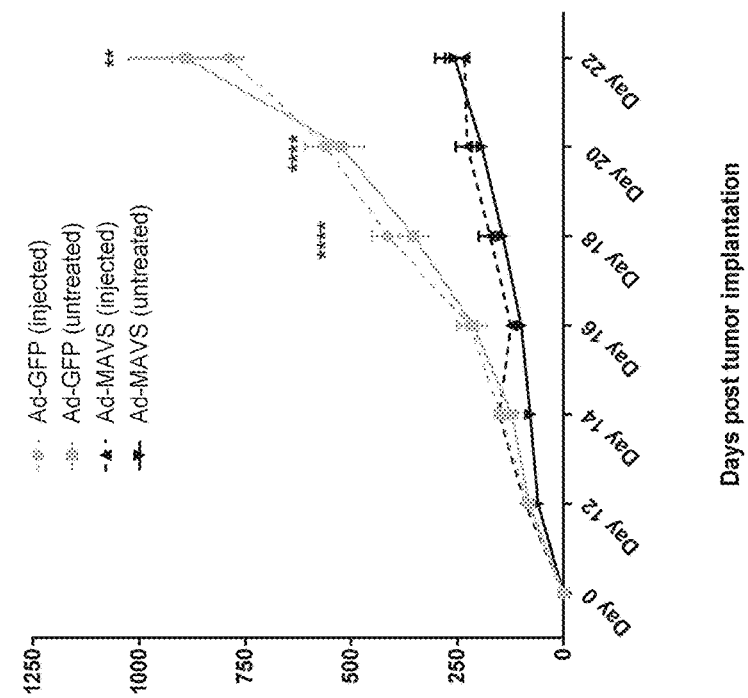

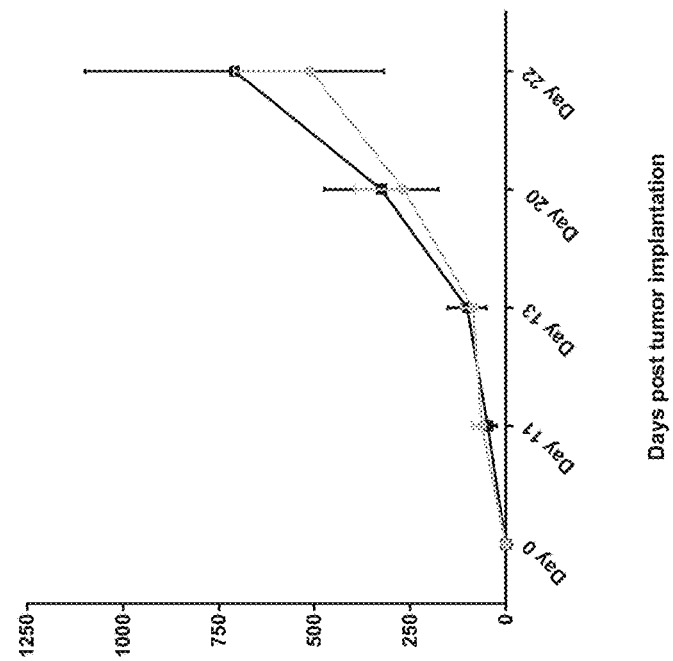
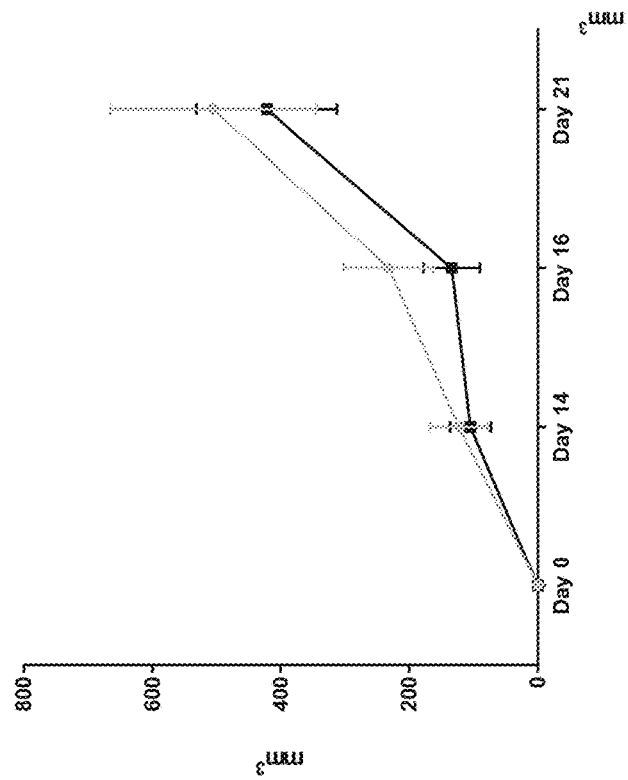

Figs 5A-5B
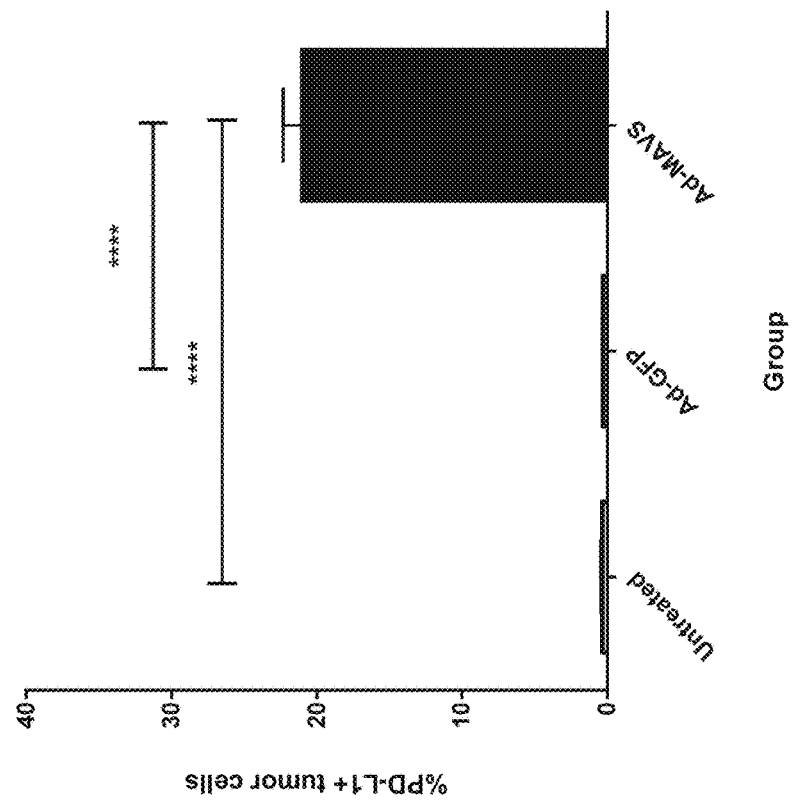
Fig. 5A
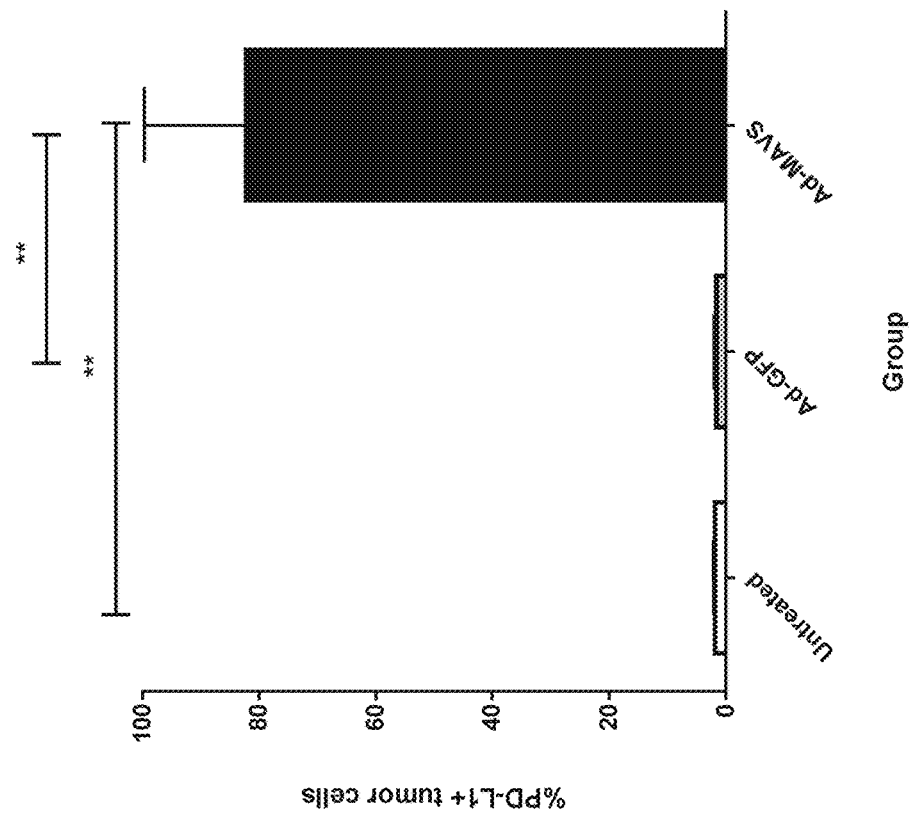
Fig. 5B

Figs 5C-5D
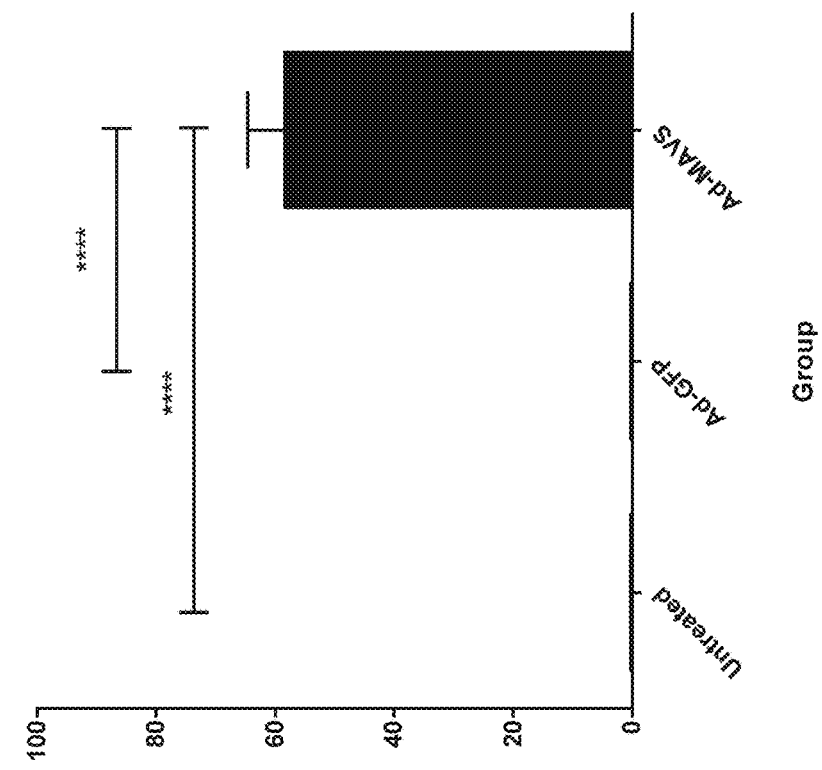
Fig. 5D
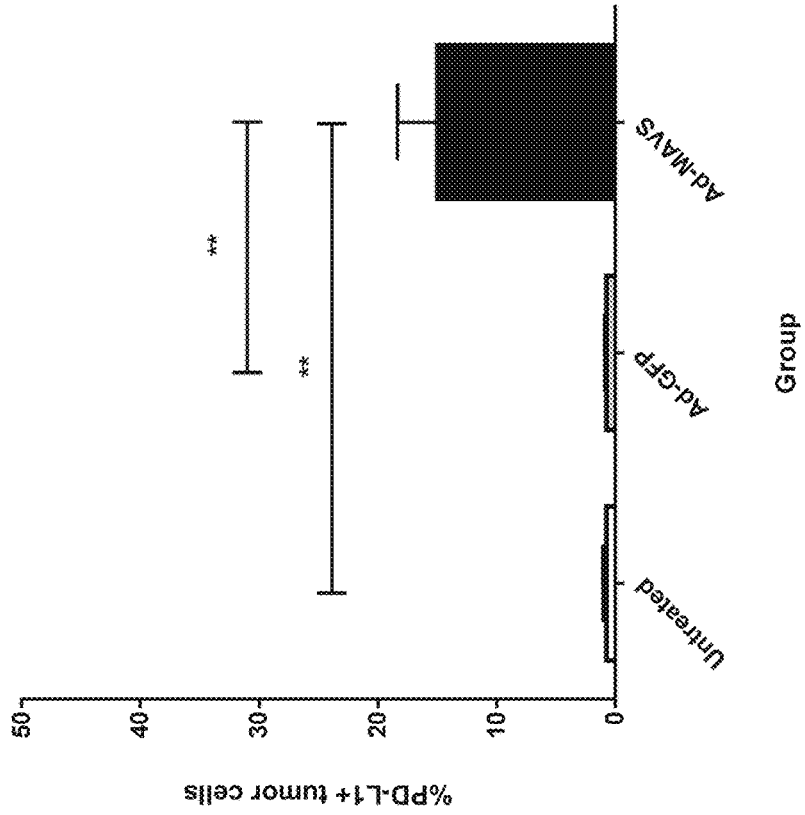
Fig. 5C

Figs 5E-5F
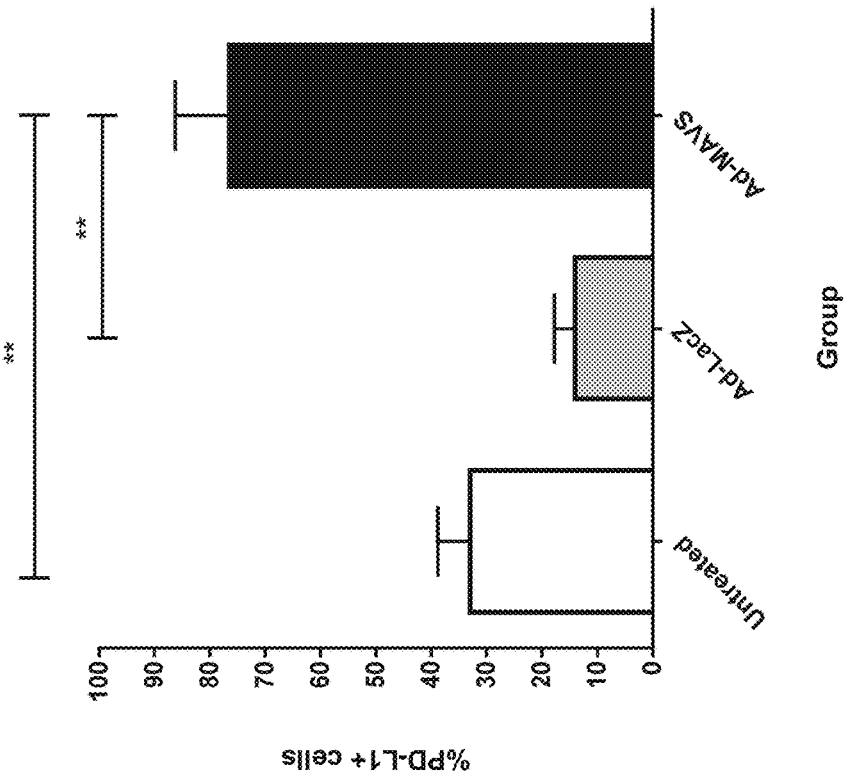
Fig. 5F
Primary MEFs PD-L1 expression
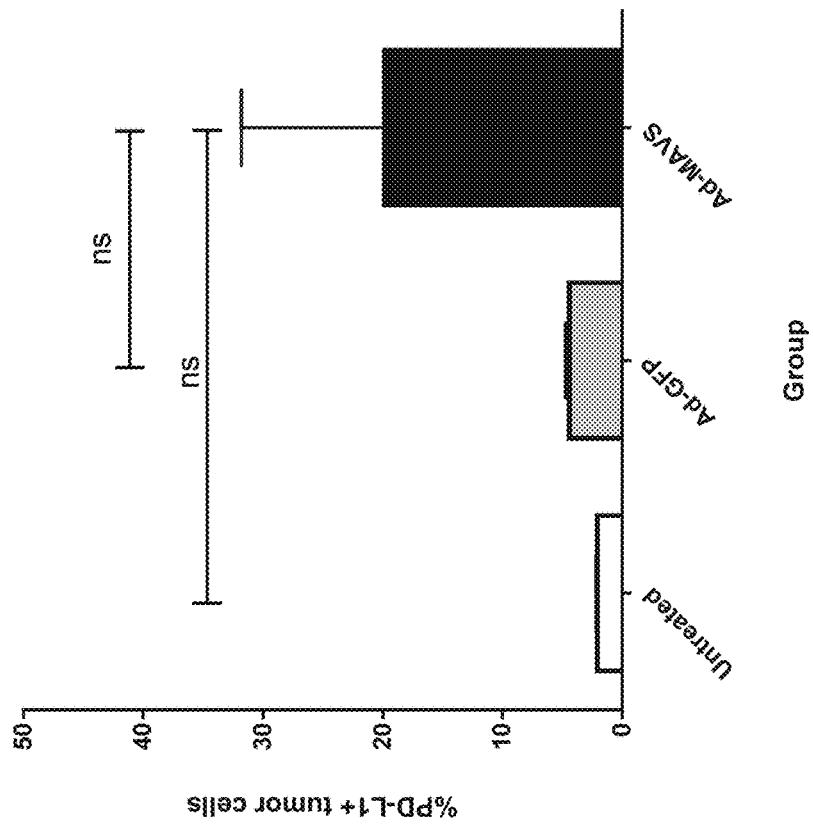
Fig. 5E
TRAMPC2 PD-L1 expression

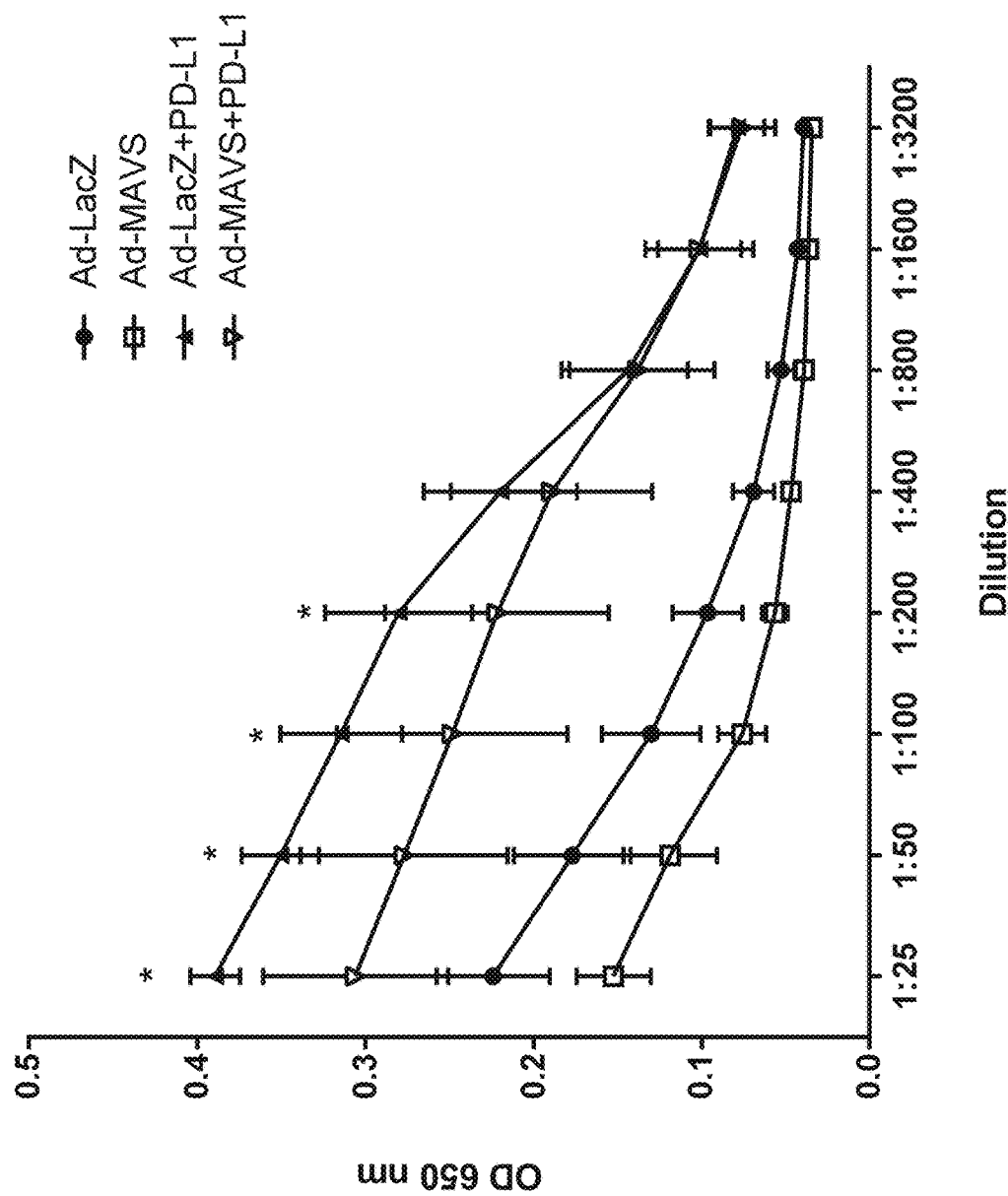

Figs 6B-6C
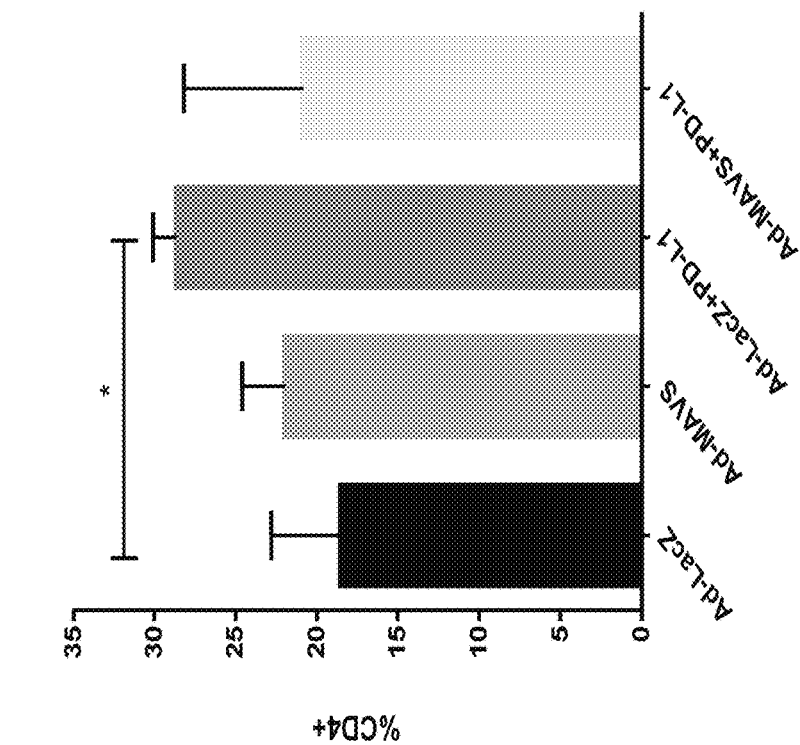
Fig. 6C
CD4 cells
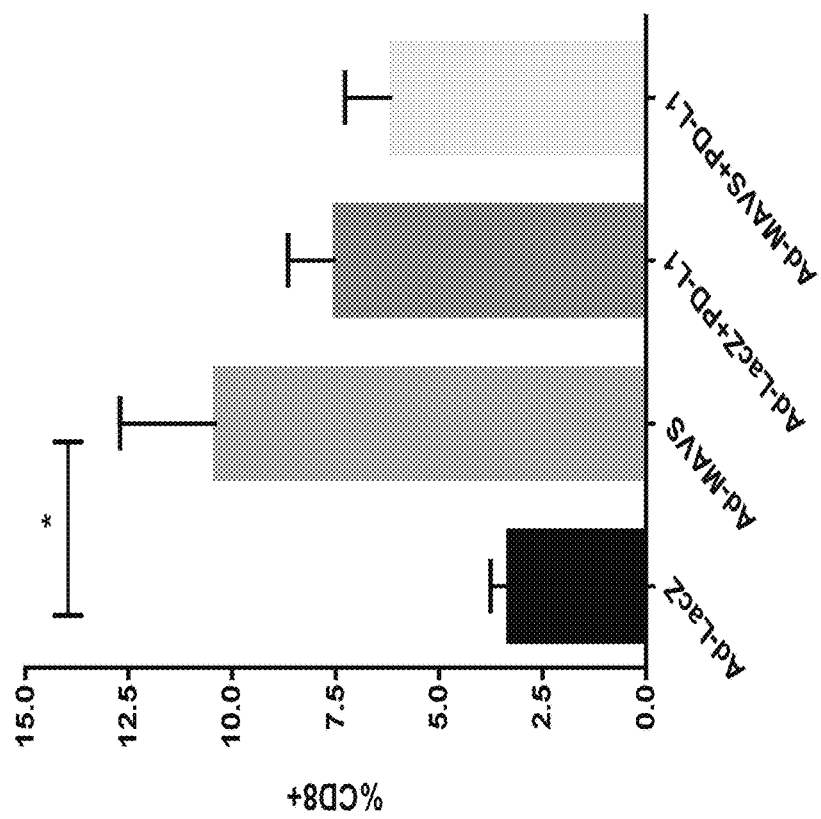
Fig. 6B
CD8 cells

Figs 6D-6E
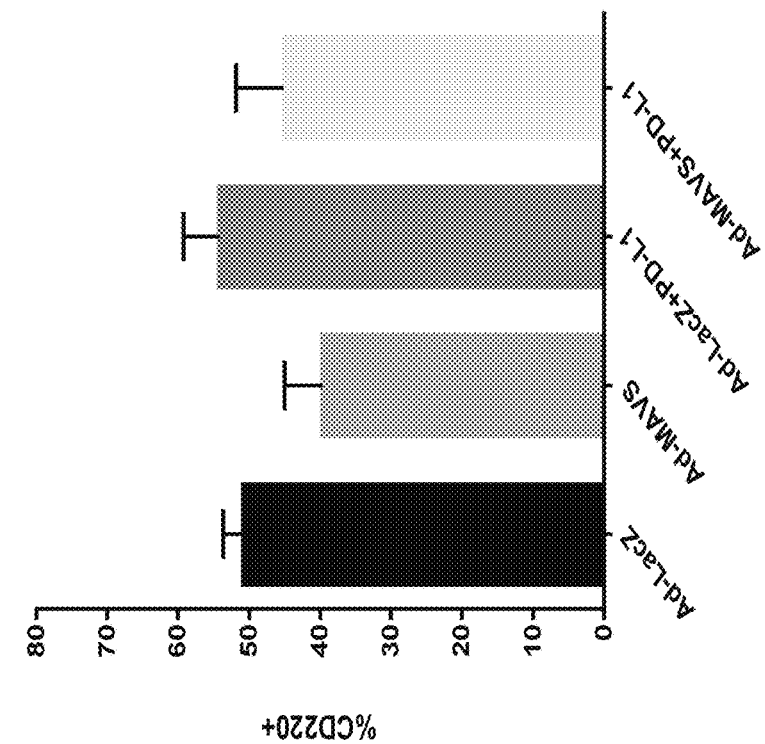
Fig. 6D
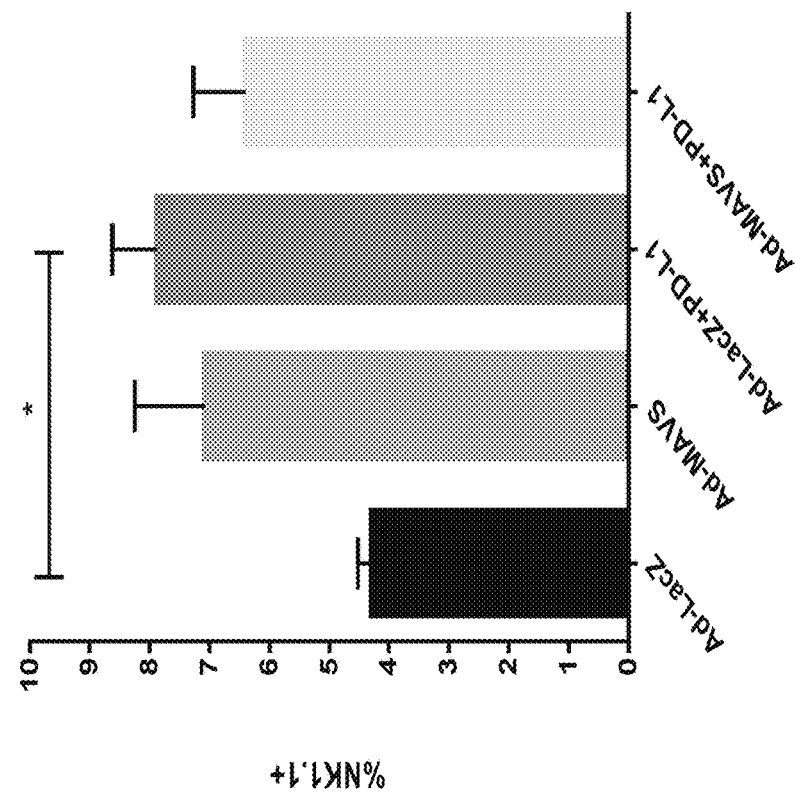
Fig. 6E

Figs 6F-6G
Fig. 6F
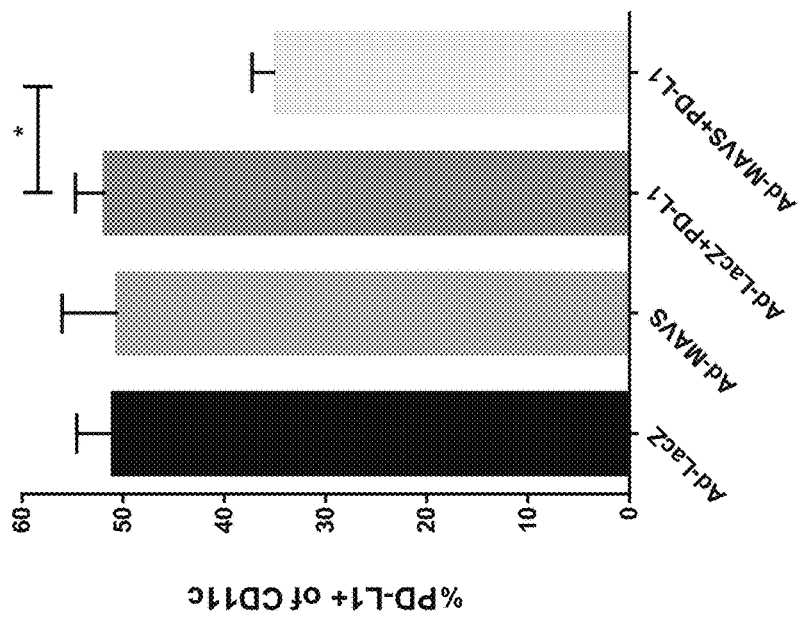
Fig. 6G
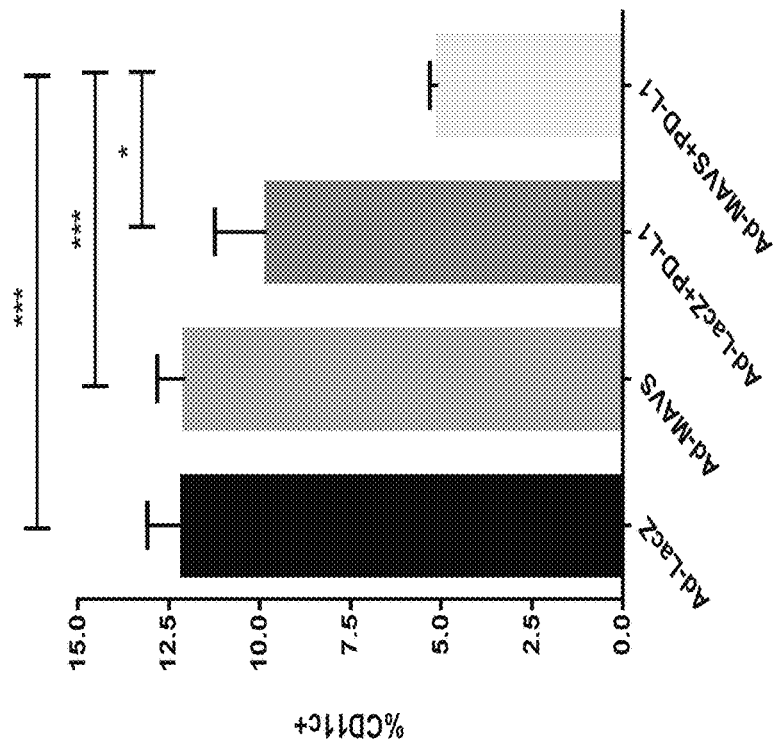

Figs 6H-6I
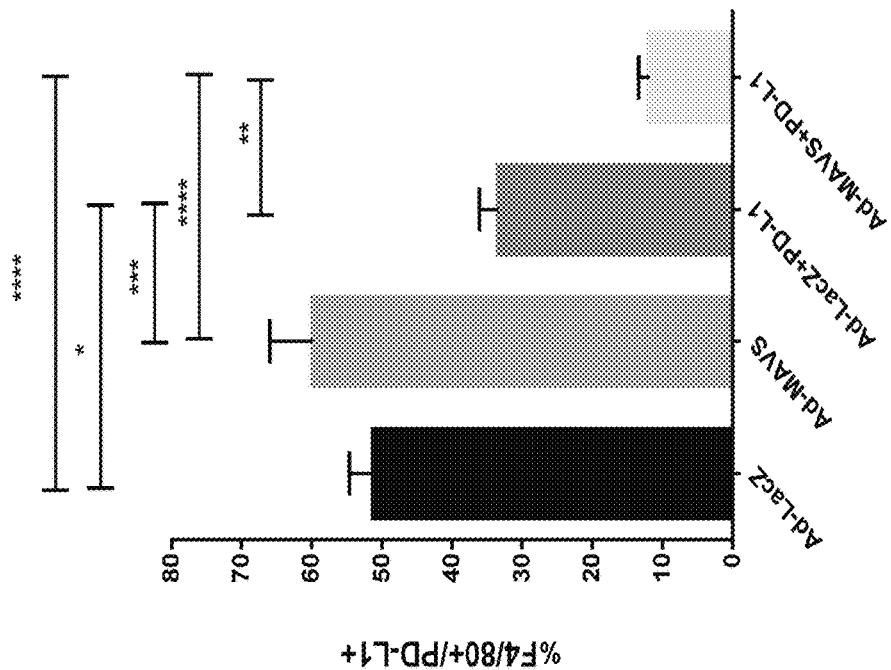
Fig. 6H
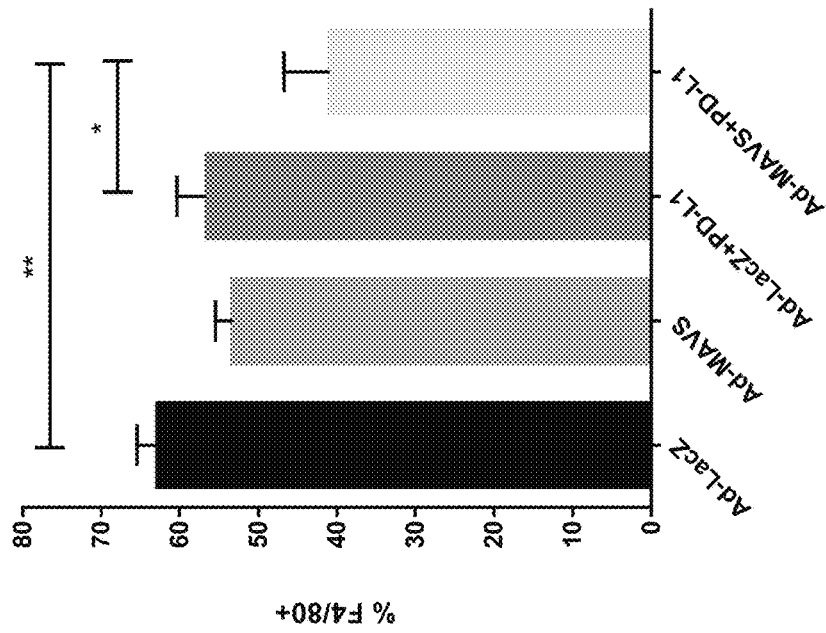
Fig. 6I

Figs 6J-6K
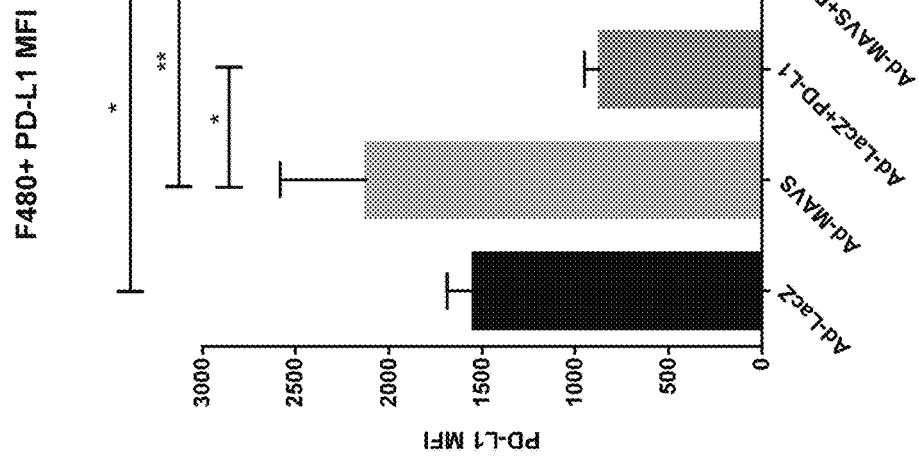
Fig. 6K
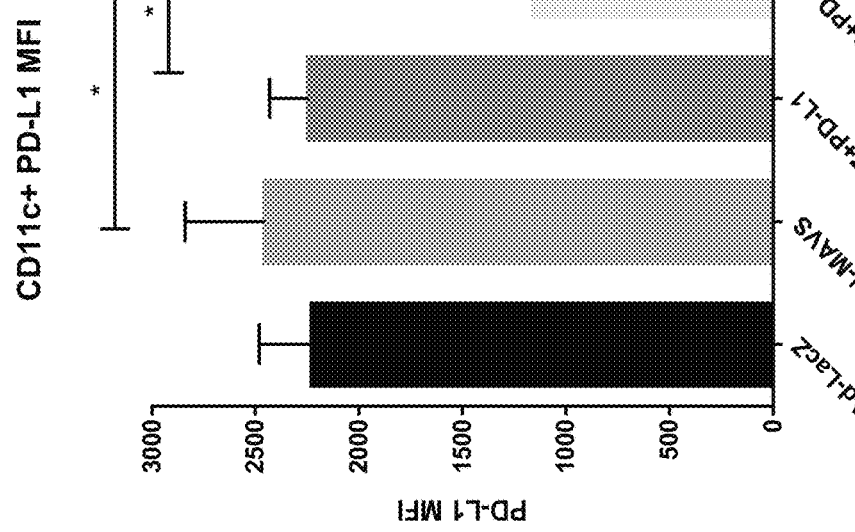
Fig. 6J

Figs 7E-7F
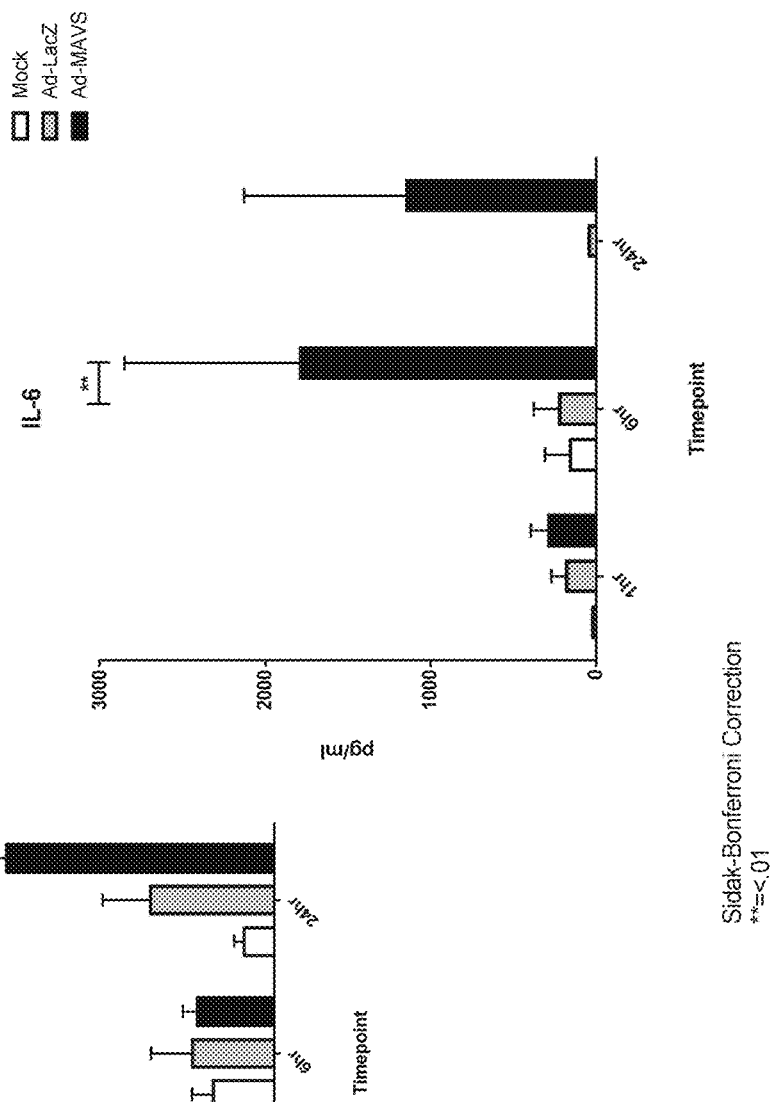
Fig. 7E
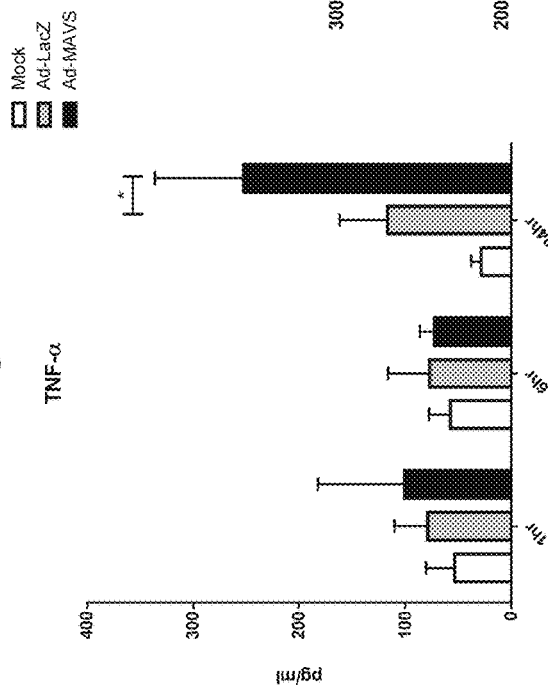
Fig. 7F

Figs 7G-7H
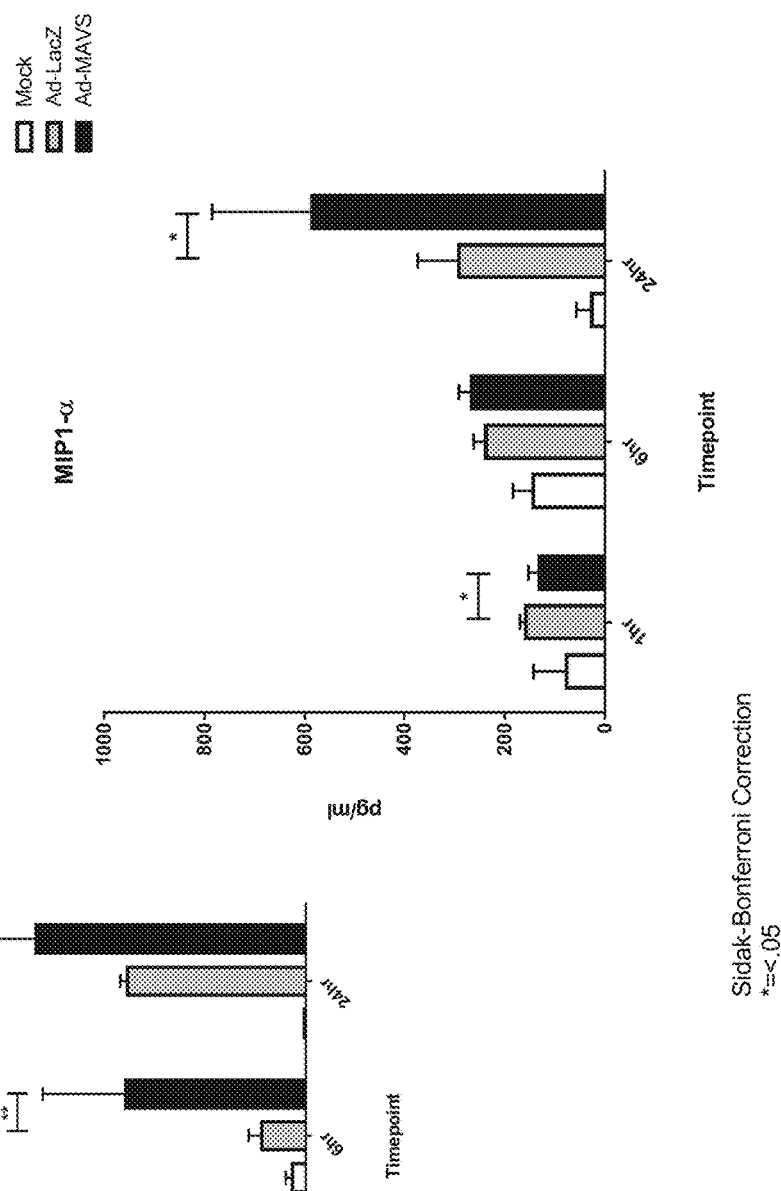
Fig. 7G
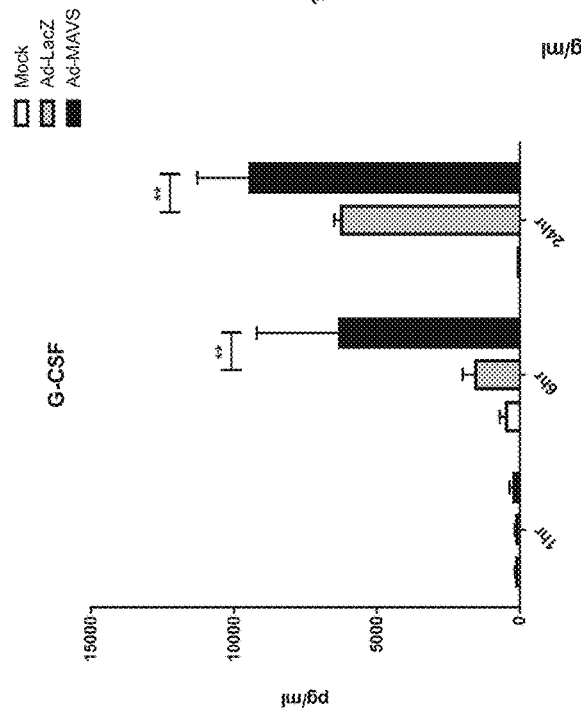
Fig. 7H

Figs 7I-7J
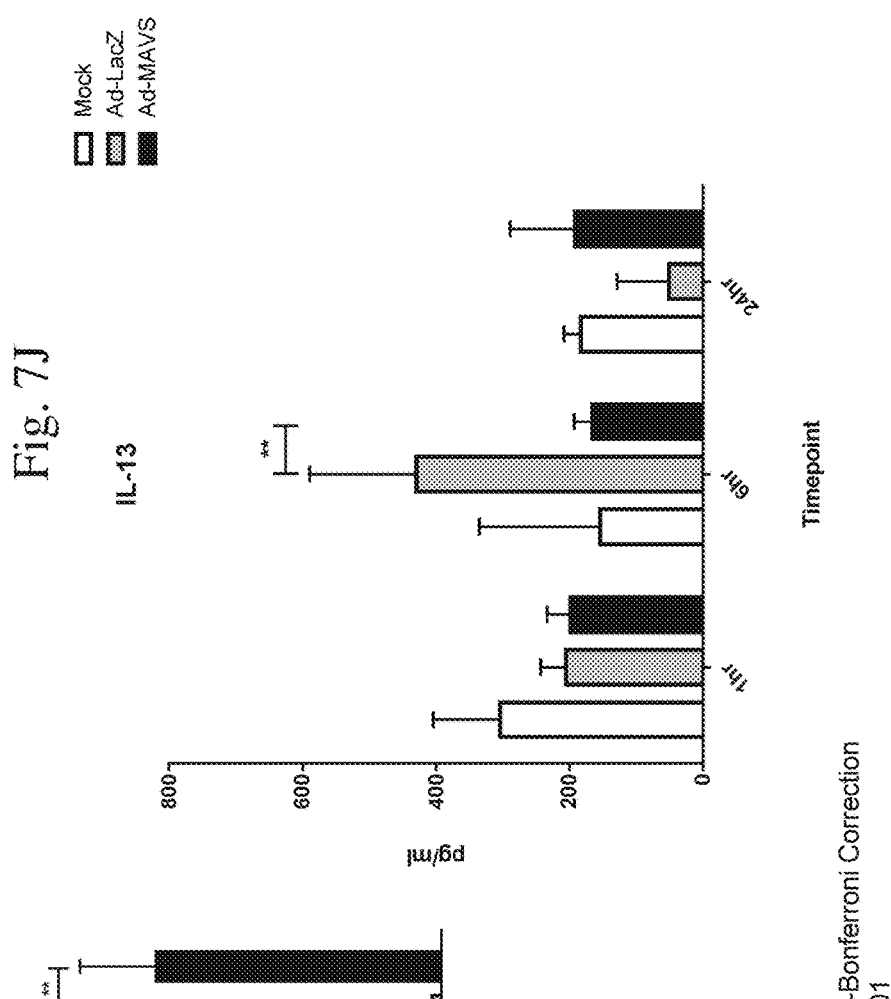
Fig. 7J
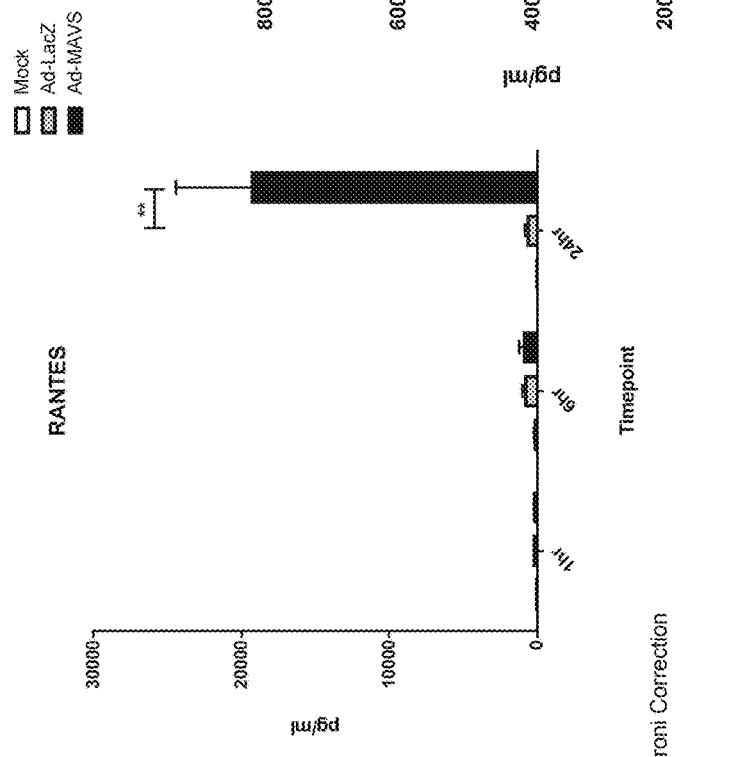
Fig. 7I

Figs 8A-8B
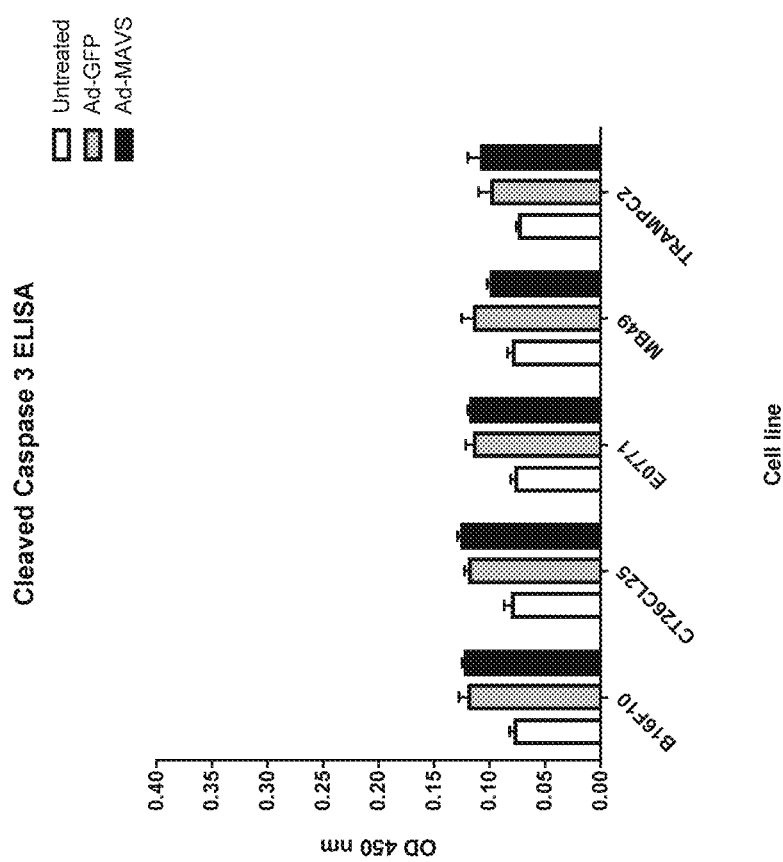
Fig. 8A
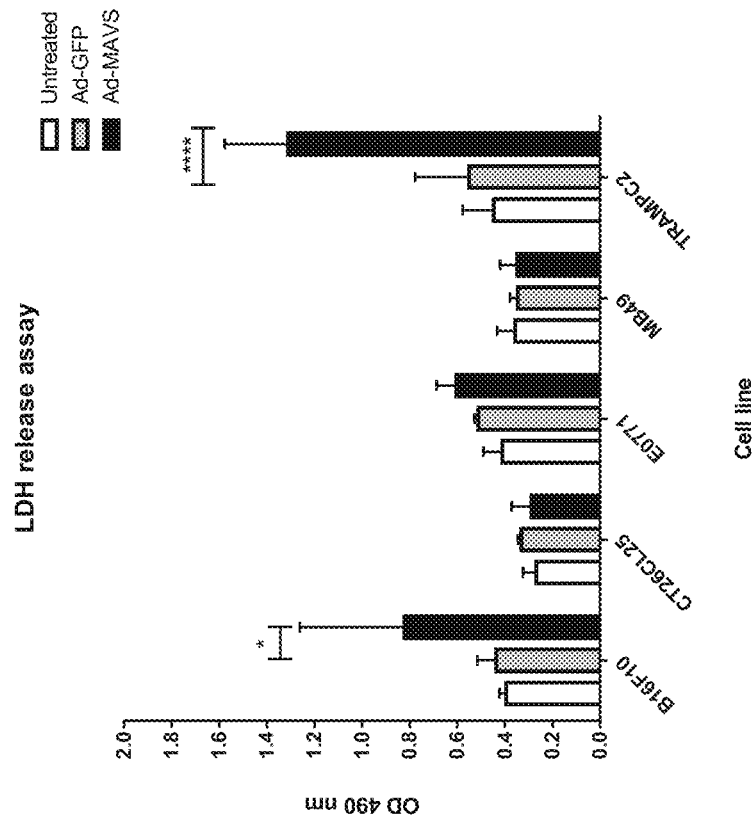
Fig. 8B

Figs 9C-9D
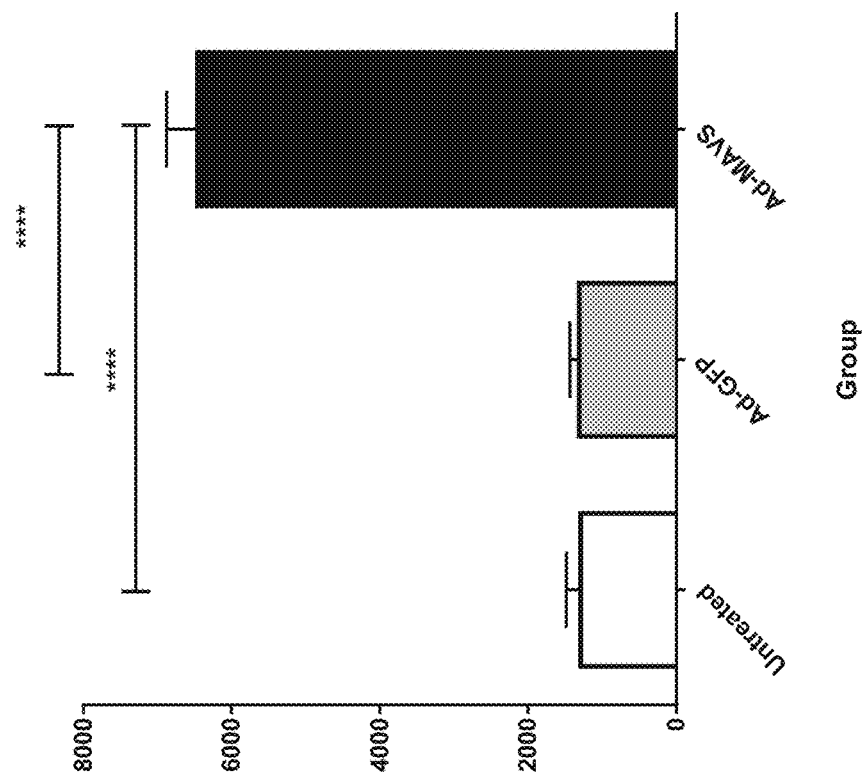
Fig. 9C
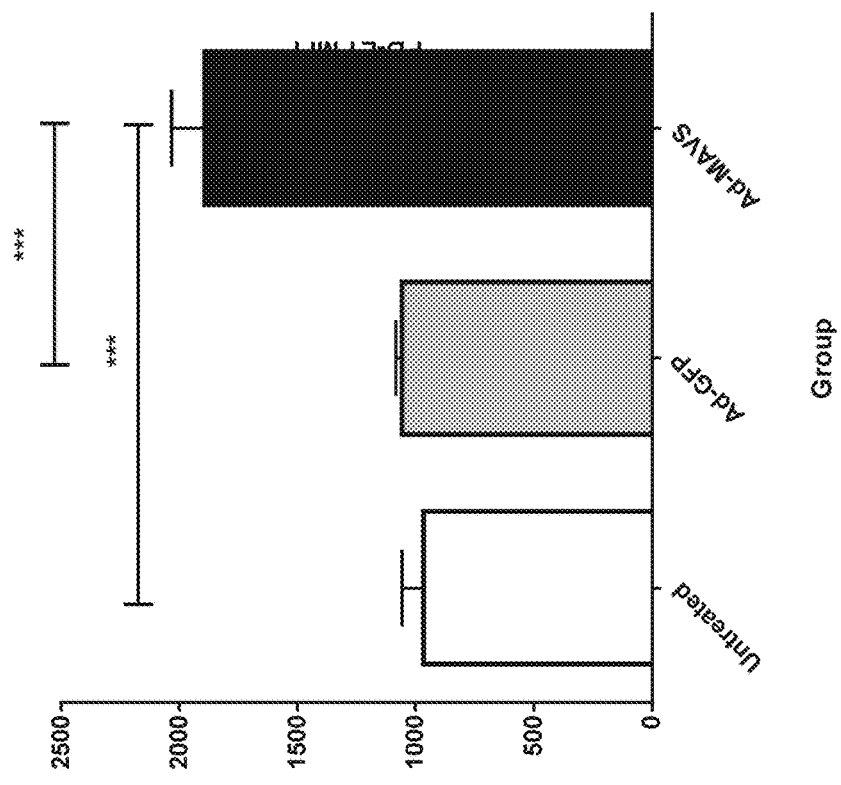
Fig. 9D

Figs 9E-9F
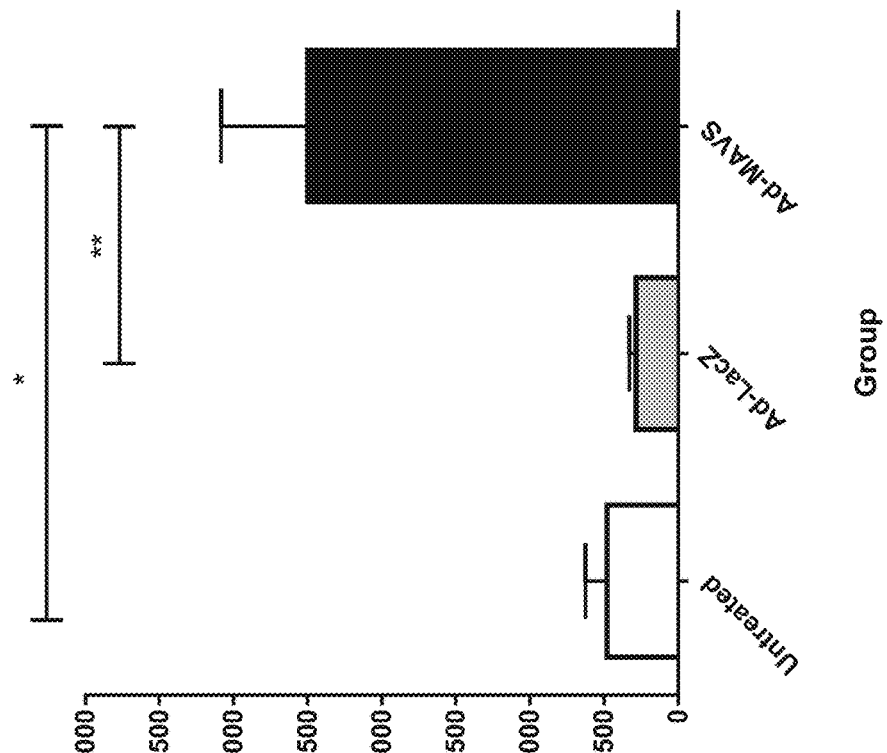
Fig. 9F
Primary MEFs PD-L1 MFI
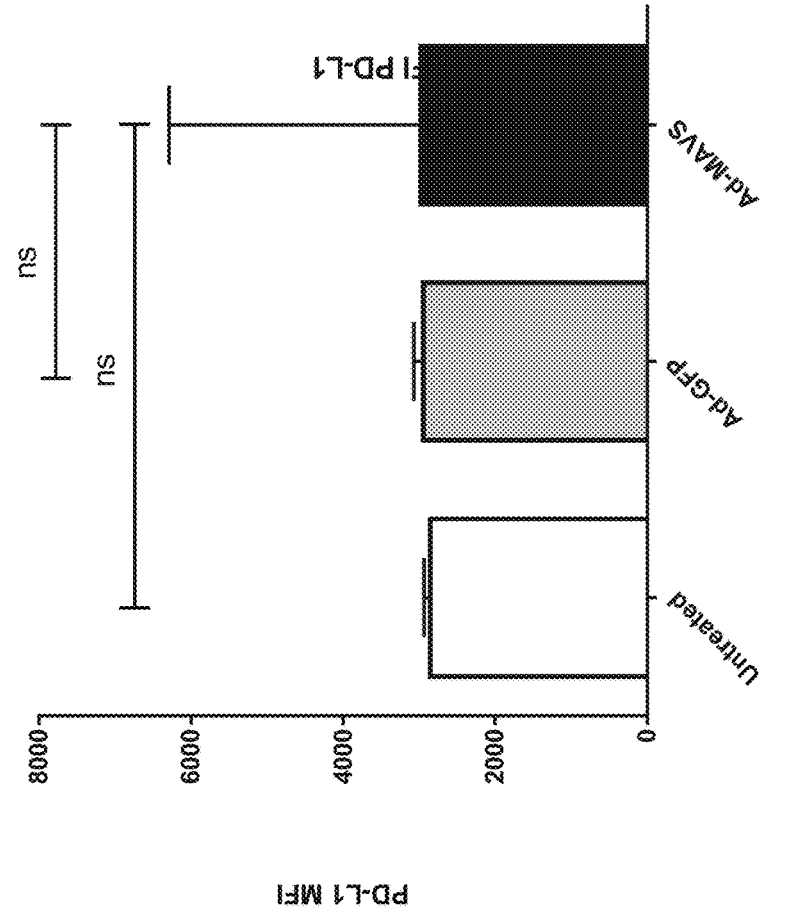
Fig. 9E
TRAMPC2 PD-L1 MFI CT26CL25 PDL1 expression B16F10 PDL1 expression

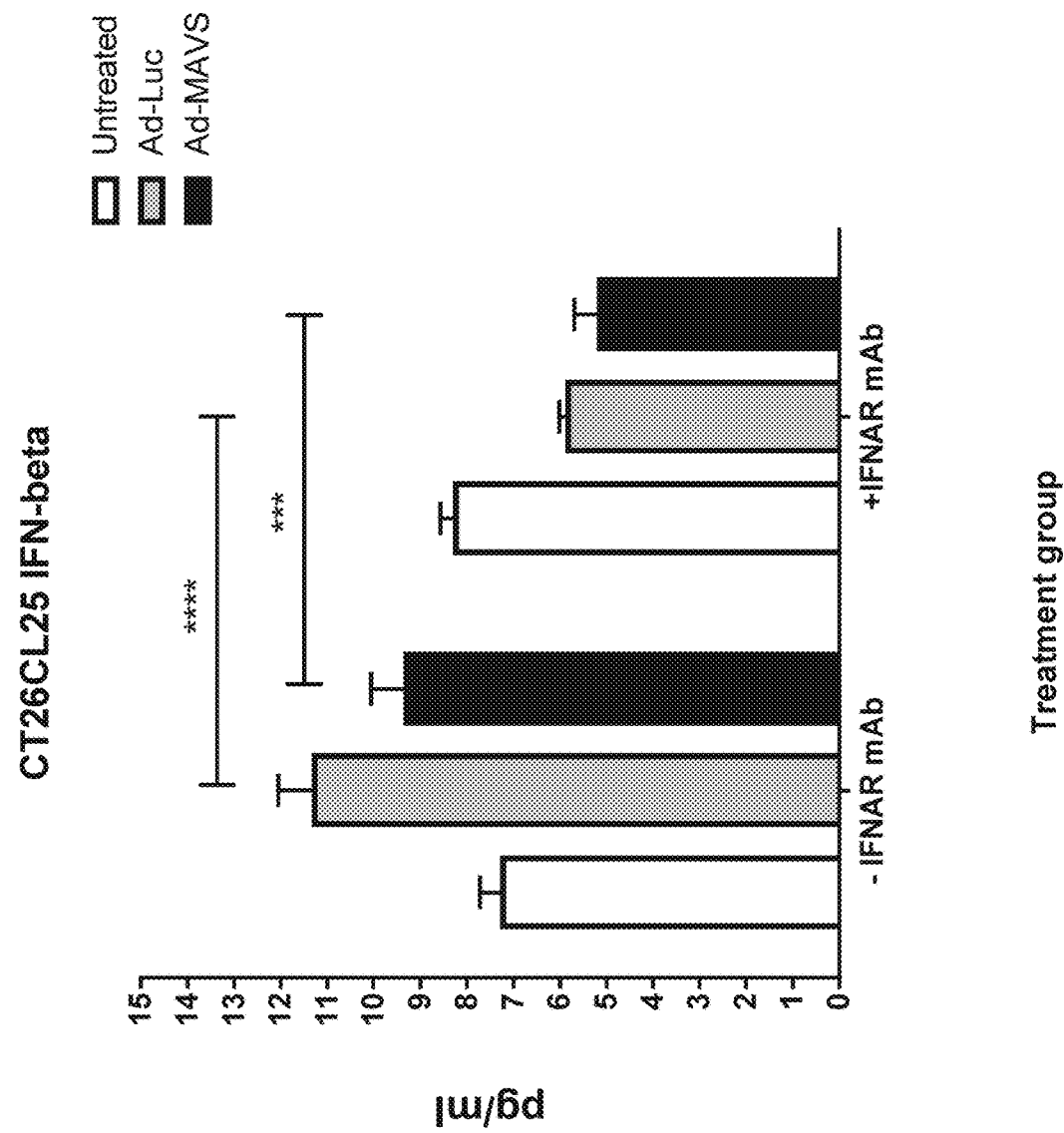

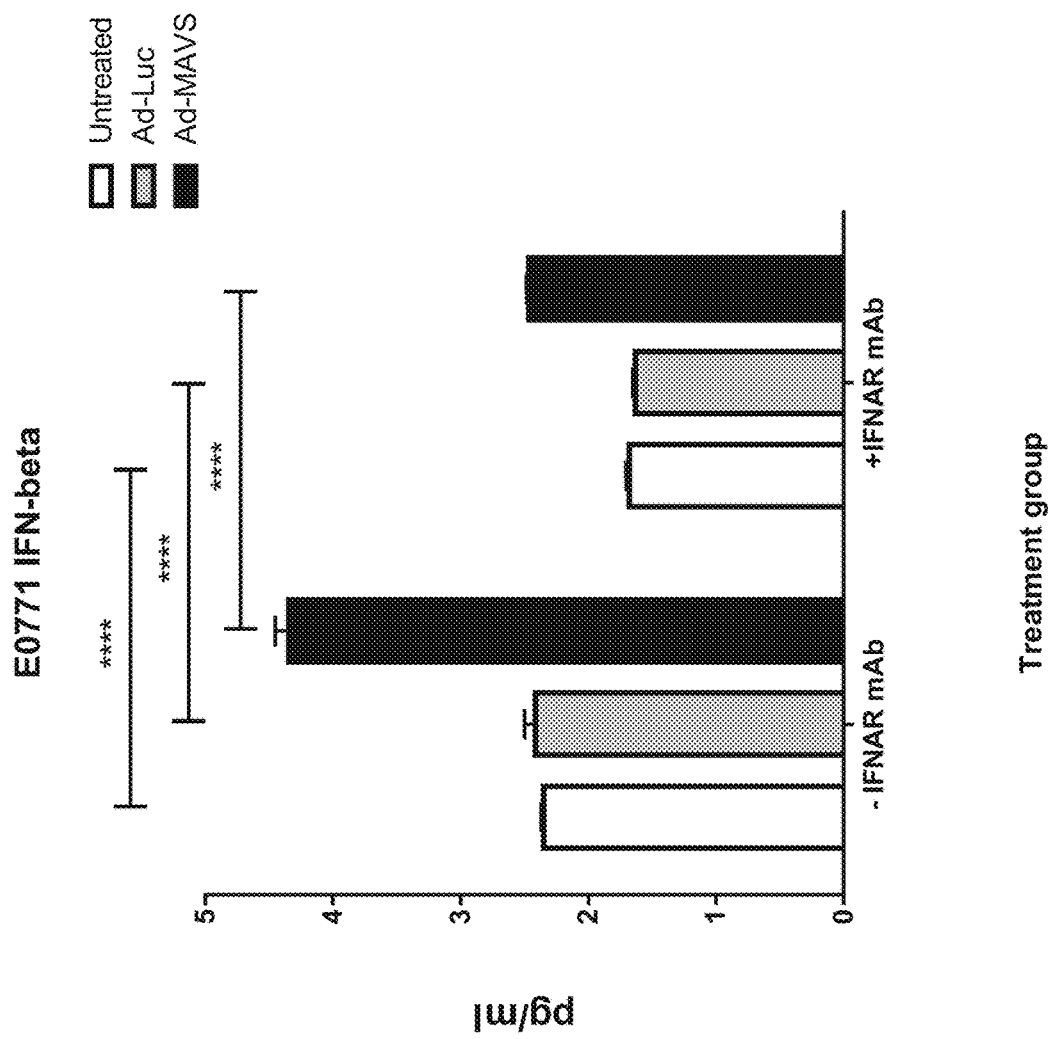

Figs 10G-I

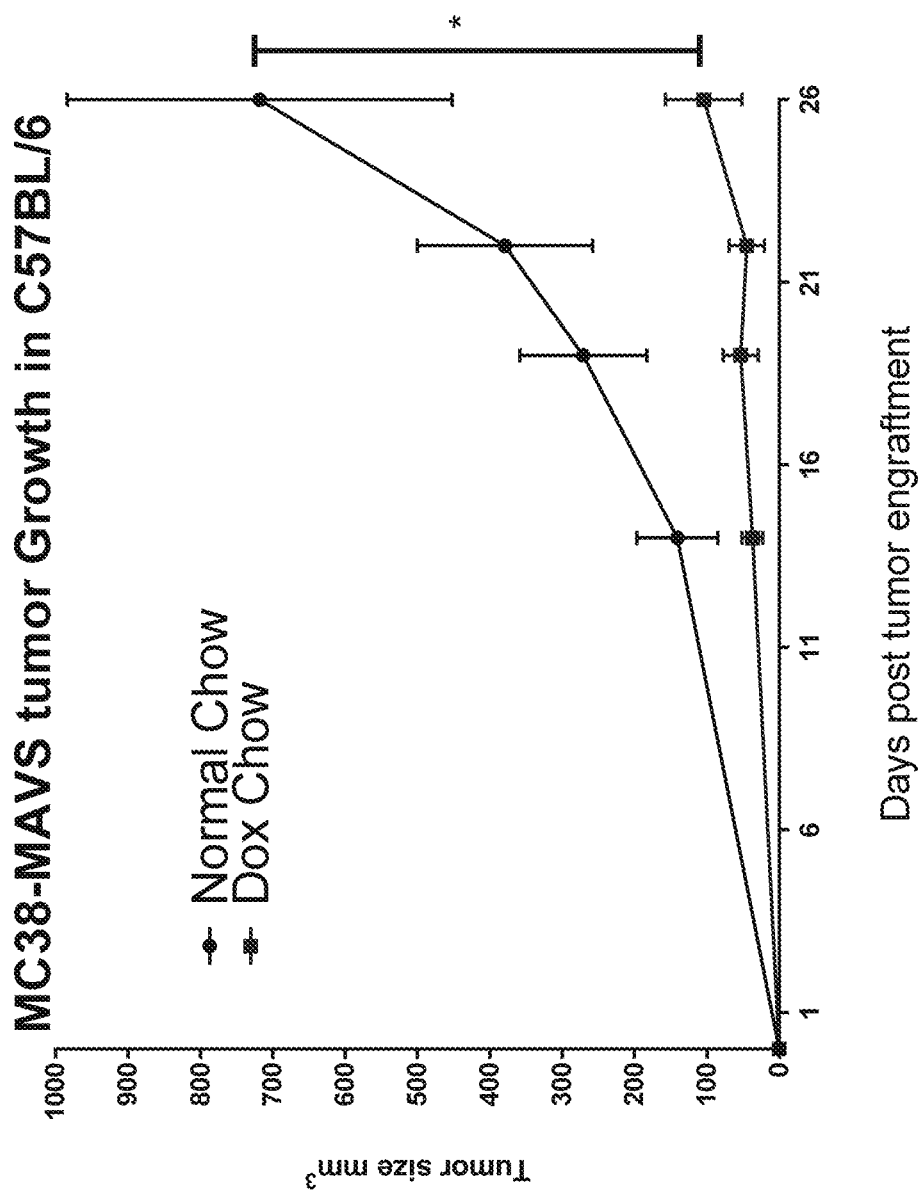

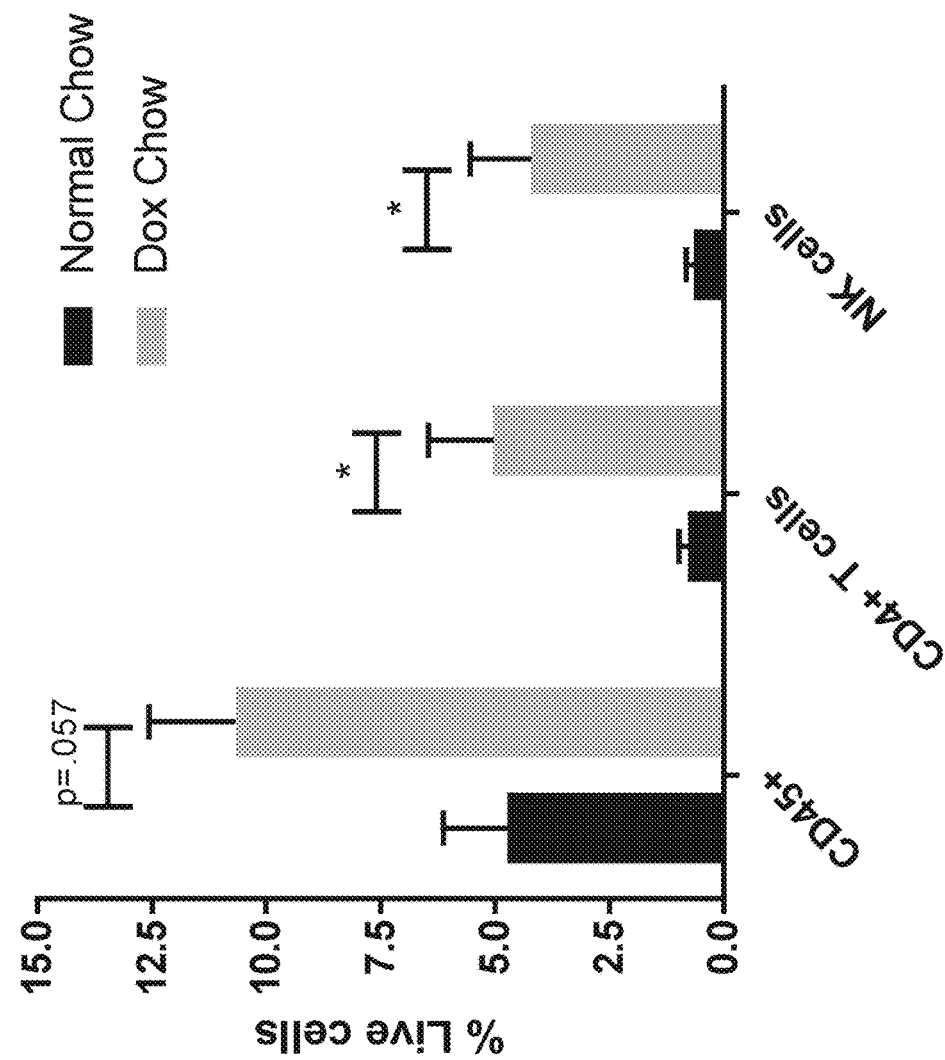

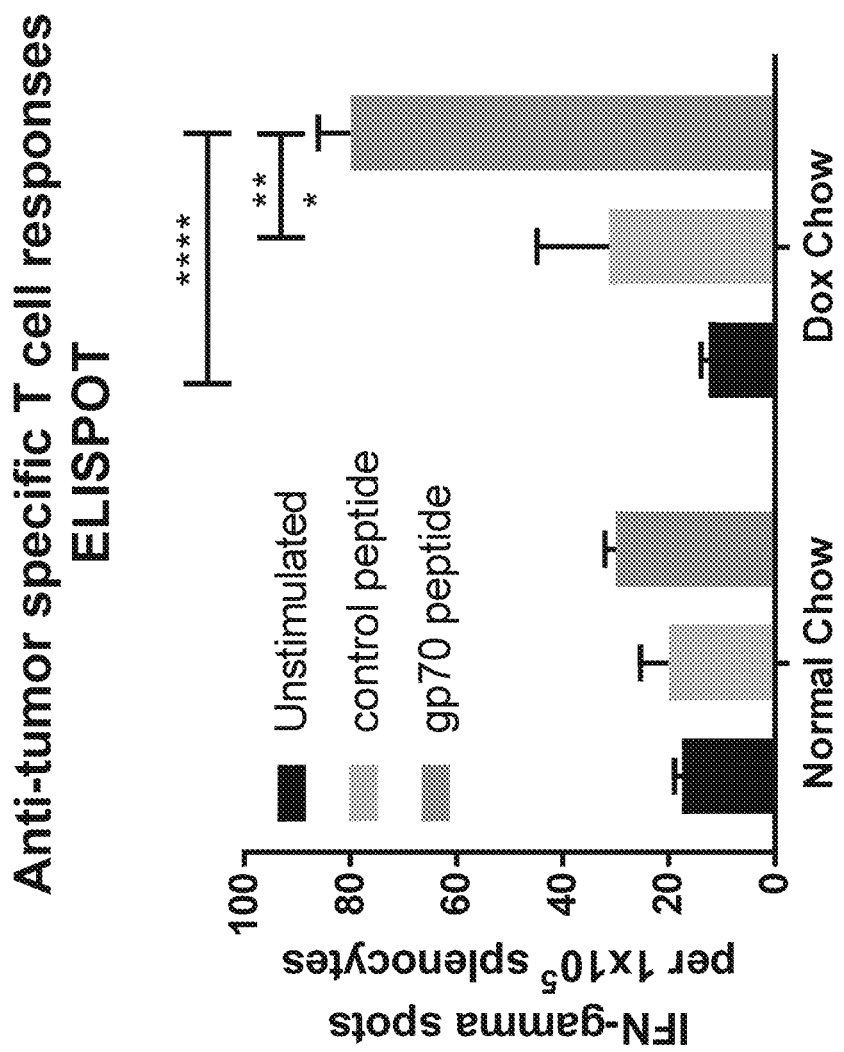

MITOCHONDRIAL ANTIVIRAL SIGNALING (MAVS) PROTEIN COMPOSITIONS AND METHODS OF USING THE SAME

CROSS-REFERENCE TO RELATED APPLICATIONS

This application claims the benefit of priority of United States Provisional Patent Application No. 62/404,559, filed Oct. 5, 2016, which is incorporated herein by reference in its entirety.

STATEMENT REGARDING FEDERALLY SPONSORED RESEARCH

This invention was made with United States government support awarded by the National Cancer Institute grant number 5T32CA009111. The United States has certain rights in this invention.

SEQUENCE LISTING

This application is being filed electronically via EFS-Web and includes an electronically submitted Sequence Listing in .txt format. The .txt file contains a sequence listing entitled "2017-10-05 5667-00414_ST25.txt" created on Oct. 5, 2017 and is 16,745 bytes in size. The Sequence Listing contained in this .txt file is part of the specification and is hereby incorporated by reference herein in its entirety.

INTRODUCTION

Cancer immunotherapy is responsible for a major paradigm shift in the way physicians treat cancer. It is becoming more apparent that the next generation of cancer therapies will be based on the principal of harnessing the specificity and potency of the human immune system to eradicate cancer. There are several prominent therapeutics that have undergone FDA approval and currently many more in various phases of preclinical/clinical testing. The overwhelming majority of these approaches aim to directly manipulate/mimic portions of the adaptive arm of the immune system.

While the use of cancer immunotherapies, such as immune checkpoint blockade, has gained significant traction as viable therapies for certain cancers, many tumors remain refractory to these immunotherapies due to their highly immunosuppressive microenvironment. There, thus, remains a need in the art for new compositions and methods for modifying the immune-suppressive microenvironment found in tumors to both efficiently suppress tumor growth and stimulate anti-tumor immune responses.

SUMMARY

The invention generally relates to compositions and methods for preventing and treating cancer. More specifically, the invention relates to MAVS compositions and their use in cancer therapeutics that may be used to treat various cancers alone or in combination with other anti-cancer therapeutic agents.

In one aspect, Mitochondrial Antiviral Signaling protein (MAVS) polypeptides are provided. The MAVS polypeptides may have at least 50%, 55%, 60%, 65%, 70%, 75%, 80%, 85%, 90%, 95%, 98%, or 99% sequence identity to SEQ ID NO: 1 (human MAVS protein), SEQ ID NO: 2 (mouse MAVS protein), or a homolog thereof.

In another aspect, polynucleotides encoding any of the MAVS polypeptides disclosed herein are also provided. In some embodiments, polynucleotides including a first heterologous promoter operably connected to a first polynucleotide encoding any one of the MAVS polypeptides described herein are provided. The polynucleotides of the present invention invention may also include a first heterologous promoter operably connected to a first polynucleotide encoding any one of the MAVS polypeptides described herein and a second polynucleotide encoding a cancer antigen operably connected to the first promoter or a second promoter.

In a further aspect, vectors including any one of the polynucleotides described herein are provided. The vectors may include an origin of replication suitable to allow maintenance of the polynucleotide within a prokaryotic or eukaryotic host cell or within a viral nucleic acid. The vector may be viral vectors, a DNA-based plasmid vector, or mini-circle DNA (mcDNA) vectors.

In another aspect, compositions including any of the MAVS polypeptides or polynucleotides and an anti-cancer therapeutic agent are also provided. Suitable anti-cancer therapeutic agents may include, without limitation, radiation, chemotherapy agents, anti-cancer biologics, or immunotherapy agents. In some embodiments, the anti-cancer therapeutic agent includes an agent targeting HER2, HER1, estrogen receptor, EGFR, or IGF1R.

In a further aspect, delivery particles including any one of the compositions disclosed herein are also provided. The delivery particles may be used to deliver either the MAVS polypeptide compositions or MAVS polynucleotide compositions into cells.

In another aspect, pharmaceutical compositions including any of the compositions described herein are also provided. The pharmaceutical compositions may include a pharmaceutical carrier, excipient, diluent, or adjuvant.

In a further aspect, methods of treating a cancer or precancer in a subject are also provided. The methods may include administering to the subject a therapeutically effective amount of any one of the MAVS compositions described herein to the subject having the cancer or precancer. The methods of the present invention also include methods of treating cancer in a subject including administering to the subject a therapeutically effective amount of any of the MAVS compositions described herein and administering to the subject a therapeutically effective amount of an anti-cancer therapeutic agent to the subject.

In a still further aspect, kits are also provided. The kits may include any of the MAVS compositions described herein and an anti-cancer therapeutic agent.

In a further aspect, cells engineered to have reduced or no expression of at least one innate immune signaling gene are also provided. The innate immune signaling gene may be any gene involved in an innate immune signaling pathway within a cell including, without limitation, MyD88, TRIF, MAVS, IRAK4, or TRAF6.

In another aspect, methods of producing a virus in a cell are also provided. The methods may include introducing a virus into any one of the engineered cells described herein.

BRIEF DESCRIPTION OF THE DRAWINGS

FIGS. 1B-1G show in vitro inflammatory profiles of Ad-MAVS infection of different cells types (n=3). Analysis carried out via standard ANOVA with Sidak-Bonferroni correction, *=<0.05. Cytokine/chemokine profiles of Ad-MAVS, Ad-GFP control, or mock infected cell are shown for bone marrow derived Dendritic cells (bmDCs) (FIG. 1B), murine embryonic fibroblasts (MEFs) (FIG. 1C), 4T1 murine breast cancer cells (FIG. 1D), B16-F10 murine melanoma cells (FIG. 1E), CT26CL25 murine colorectal cancer cells (FIG. 1F), and TRAMPC2 murine prostate cancer cells (FIG. 1G). In all experiments N=3 and analysis carried out via unpaired t test, *=<0.05 =<0.01 *=<0.001 ****=<0.0001.

FIGS. 2A-2E show in vitro derived IFN-β in response to Ad-MAVS infection in multiple cancer cell types (n=3) including murine embryonic fibroblasts (MEFs) (FIG. 2A), 4T1 murine breast cancer cells (FIG. 2B), B16-F10 murine melanoma cells (FIG. 2C), CT26CL25 murine colorectal cancer cells (FIG. 2D), and TRAMPC2 murine prostate cancer cells (FIG. 2E). Analysis carried out via unpaired t test, *=<0.05 =<0.01 *=<0.001 ****=<0.0001.

FIGS. 3A-3D show that Ad-MAVS leads to tumor growth inhibition in vitro in multiple cancer cell types (n=3) including 4T1 murine breast cancer cells (FIG. 3A), B16-F10 murine melanoma cells (FIG. 3B), CT26CL25 murine colorectal cancer cells (FIG. 3C), and TRAMPC2 murine prostate cancer cells (FIG. 3D). Analysis carried out via standard ANOVA with Sidak-Bonferroni correction, *=<0.05 =<0.01 *=<0.001.

FIGS. 4A-4D show MAVS induced adaptive immune responses and anti-tumor responses after intralesional injection of a LacZ+CT26CL25 murine colorectal tumor model (n=5). CT26.CL25 cells were engrafted bilaterally into the flanks of Balb/C mice. After one week, a tumor at one side were intralesionally challenged with control Ad-GFP or Ad-MAVS (5×10^10 viral particles). Tumor growth was measured for 3 weeks. Analysis carried out via standard ANOVA with Sidak-Bonferroni correction, *=<0.05 =<0.01 **=<0.0001. (FIG. 4A) Splenocytes from engrafted mice were assessed for CT26.CL25-specific (anti-LacZ) T cell responses by IFN-gamma ELISPOTS assay. (FIG. 4B) CT26.CL25-specific antibodies in the serum were assessed by ELISA analysis for anti-Ad IgG. (FIG. 4C) CT26.CL25-LacZ specific antibodies in the serum were assessed by ELISA analysis for anti-LacZ IgG. (FIG. 4D) Tumor growth was measured over 3 weeks in each treatment group. (FIG. 4E) CT26.CL25 cells were engrafted into NOD/SCID mice. After one week, the tumors are challenged with control Ad-GFP or Ad-MAVS. Tumor growth was measured over 3 weeks. (FIG. 4F) CT26.CL25 cells were engrafted into RAGKO mice. After 11 days, the tumors are challenged with control Ad-GFP or Ad-MAVS. Tumor growth was measured over 3 weeks.

FIGS. 5A-5F show MAVS expression leads to a positive immunoregulatory feedback loop to augment the expression of PD-L1 in multiple cancer cell lines by FACS analysis (n=3) including in B16F10 cells (FIG. 5A), CT26CL25 cells (FIG. 5B), E0771 cells (FIG. 5C), MB49 cells (FIG. 5D), TRAMPC2 cells (FIG. 5E), and Primary MEF cells (FIG. 5F). Analysis carried out via unpaired t test, =<0.01 *=<0.001 ****=<0.0001.

FIGS. 6A-6M show combination of Ad-MAVS and PD-L1 inhibition leads to robust anti-tumor immunity and systemic changes in immune profiles (n=5) FIG. 6A. Analysis carried out via standard ANOVA with Sidak-Bonferroni correction, *=<0.05 ***=<0.001. FIGS. 6B-6M show the percentages of the indicated cell types in the response after the indicated treatment. FIG. 6B is the percent CD8 T cells. FIG. 6C is is the percent CD4 T cells. FIG. 6D is the percent NK1.1 cells. FIG. 6E is the percent B cells. FIG. 6F is the percent CD11c cells. FIG. 6G is the percent CD11c and PD-L1 cells. FIGS. 6H and 6I are the percent F4/80 and F4/80 PD-L1 cells, respectively. FIG. 6J is the percent CD11 PD-L1 MFI cells. FIG. 6K is the percent F480 PD-11 MFI cells. FIG. 6L is the PD-L1 B cells and FIG. 6M is the B220 PD-L1 cells.

FIGS. 7A-7L show the effect on systemic inflammation and regulatory responses in response to Ad-MAVS after intra-venous administration to significantly transduce the liver on multiple cytokines and chemokines (7A-L). N=5, analysis carried out via unpaired t test, =<0.01 *=<0.001 ****=<0.0001. FIG. 7A shows IL-1β induction. FIG. 7B shows the IL-2 production. FIG. 7C shows the IL-10 production. FIG. 7D shows the IFN-γ production. FIG. 7E shows the TNF-a production. FIG. 7F shows the IL-6 production. FIG. 7G shows the G-CSF production. FIG. 7H shows the MIP1-α production. FIG. 7I shows the RANTES production. FIG. 7J shows the IL-13 production. FIG. 7K shows the MCP-1 production. FIG. 7L shows the MIP1-β production.

FIGS. 8A-8B show that infection of Ad-MAVS leads to induced cell death in vitro of multiple types of tumor cells using the LDH release assay (FIG. 8A) or the cleaved caspase 3 ELISA (FIG. 8B) (N=3 analysis carried out via unpaired t test, =<0.01 *=<0.001 ****=<0.0001).

FIGS. 9A-9F show immune checkpoint regulation in response to Ad-MAVS in vitro of multiple types of tumor cells (N=3 analysis carried out via unpaired t test, =<0.01 *=<0.001 ****=<0.0001). FIG. 9A shows B16F10 cells. FIG. 9B shows CT26CL25 cells. FIG. 9C shows E0771 cells. FIG. 9D shows MB49 cells. FIG. 9E shows TRAMPC2 cells. FIG. 9F shows primary MEFs.

FIGS. 10A-10I show immune checkpoint regulation of PD-L1 in response to Ad-MAVS and its relation to interferon signaling in multiple types of tumor cells (N=3 analysis carried out via unpaired t test, =<0.01 *=<0.001 ****=<0.0001). FIG. 10A shows B16F10 cells. FIG. 10B shows CT26CL25 cells. FIG. 10C shows E0771 cells. FIG. 10D shows B16F10 cells. FIG. 10E shows CT26CL25 cells. FIG. 10F shows E0771 cells. FIGS. 10G-I shows the Interferon response (FIGS. 11A-11B) Expression of innate immune genes after 24 h doxycycline-mediated MAVS induction in MC38 and CT26.CL25 colorectal carcinoma cells. (FIG. 11C) Expression of innate immune genes after 24 h infection of MC38 cells with Adenovirus expressing MAVS (Ad-MAVS). (FIG. 11D) Extracellular IFNβ measurement of different tumor cell lines infected with Ad-MAVS for 24 h.

FIGS. 12A-12D show MAVS induction in the tumor microenvironment suppresses tumor growth. (FIG. 12A) Implanted CRC tumor model. 10^6 MC38-MAVS cells or 10^5 CT26.CL25-MAVS cells were engrafted subcutaneously in the flank. One week post engraftment, mice were given normal or doxycycline-containing chow for MAVS induction in tumor microenvironment. (FIG. 12B) Confirmation of MAVS induction in tumor mass by RT-qPCR. (FIGS. 12C-12D) Tumor growth was measured after engraftment and treatment as described in (FIG. 12A). n=5 per group.

FIGS. 13A-13C show MAVS induction in the tumor microenvironment promotes immune cells infiltration and anti-tumor specific immune responses. (FIG. 13A) MC38 with dox-inducible MAVS were engrafted in transgenic T-LUX mice (n=5 per group). Luciferase quantification allows for visualization of CD4+ T cells infiltration into tumor mass. (FIG. 13B) FACS analysis of immune cells infiltration in engrafted MC38 tumor (n=5, at 3-4 weeks post engraftment). (FIG. 13C) Splenocytes of engrafted mice were assessed for MC38-specific T cell responses by IFN-gamma ELISPOTS assay.

(FIG. 14A) MC38-MAVS engrafted tumors (4 weeks) as described in FIG. 12A were analyzed by immuno-fluorescence staining for MAVS (Green) and PDL1 (Red). (FIG. 14B) PDL1 expression in engrafted CRC cells after 3-4 weeks were analyzed by FACS. Ad-GFP and Ad-MAVS were treated intralesionally at week 1 post tumor engraftment.

DETAILED DESCRIPTION

Figure 1A:
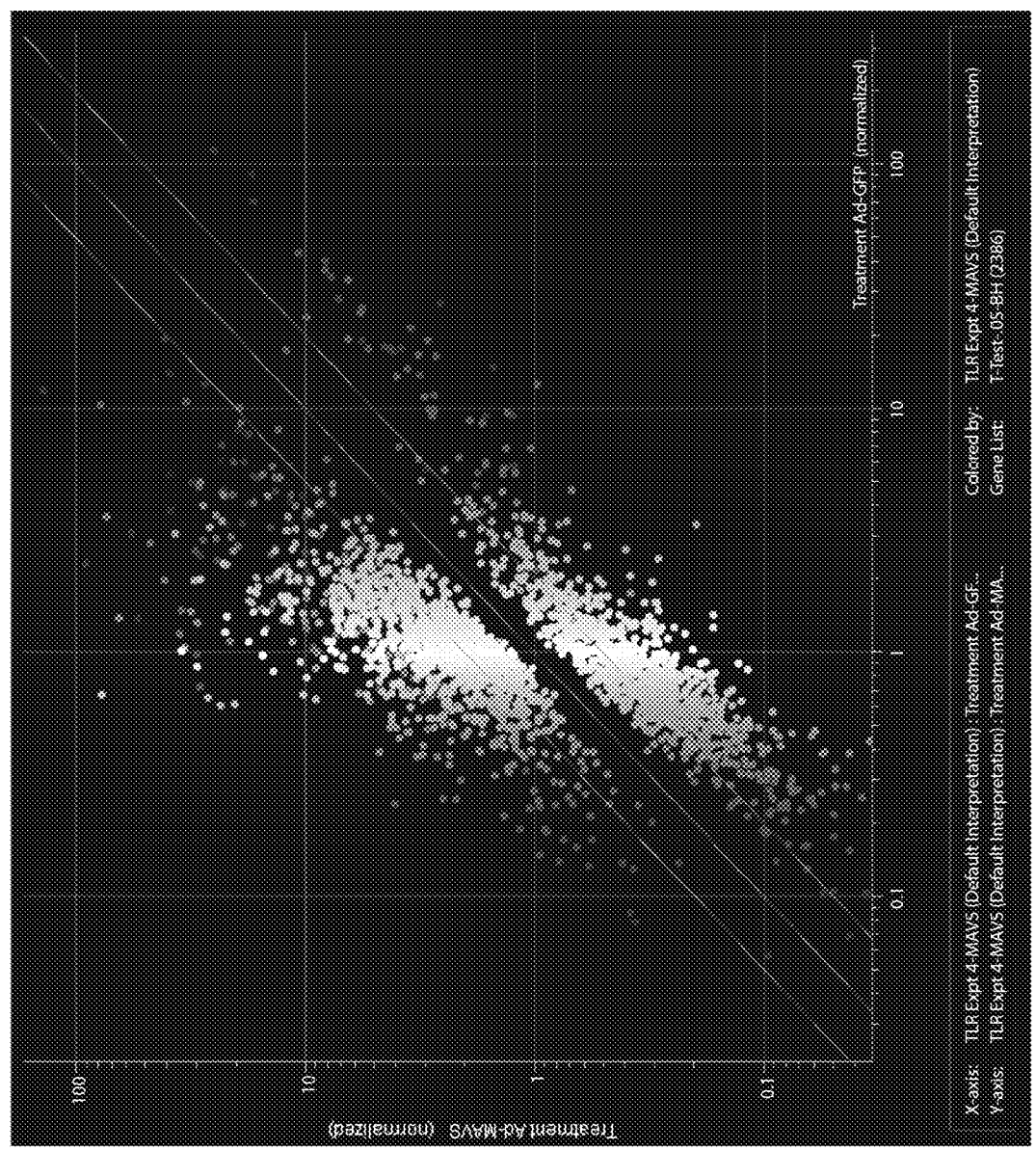
FIG. 1A is a heatmap showing an exemplary comparative gene expression in cells (bone marrow derived Dendritic cells (bmDCs) and murine embryonic fibroblasts (MEFs)) treated with Adenovirus expressing GFP or MAVS.
Figure 1F:
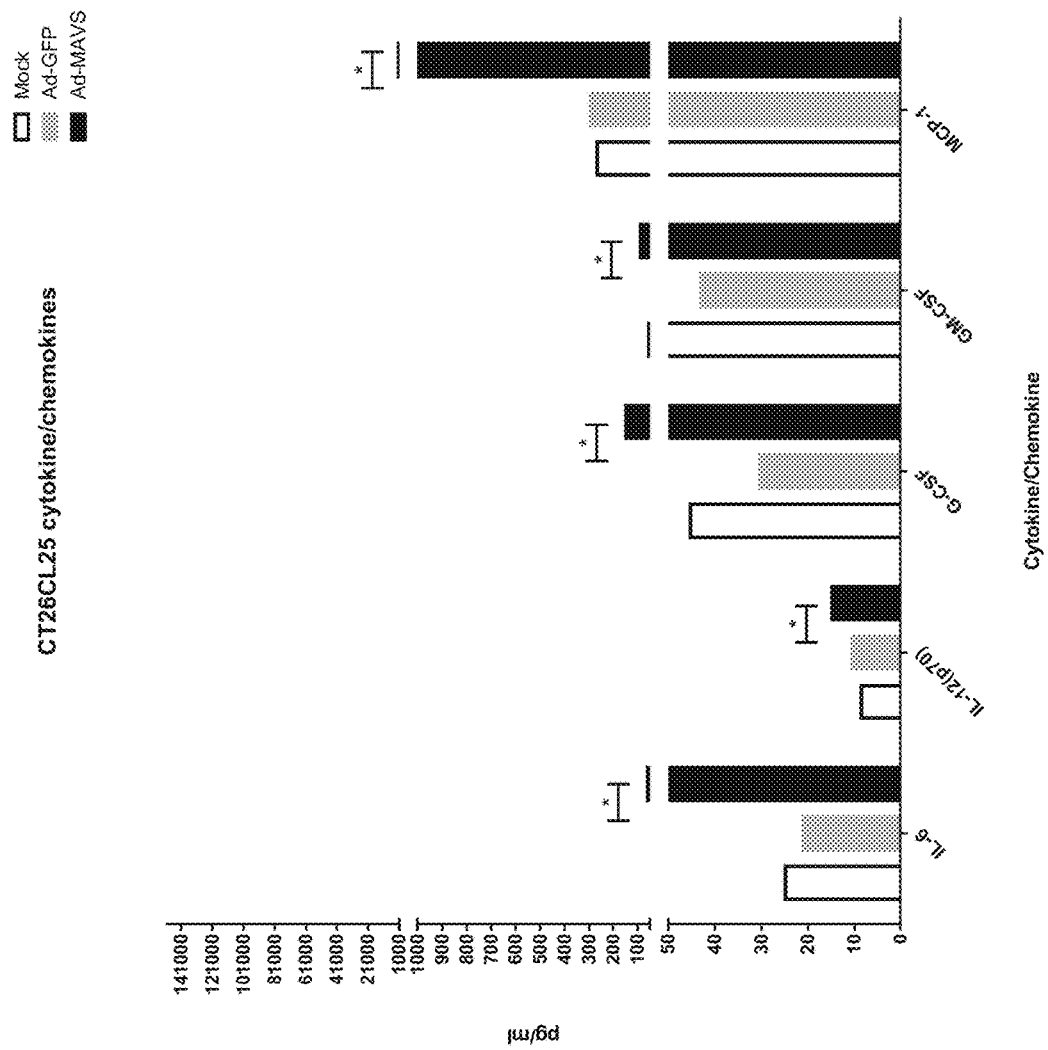
Figure 2A:
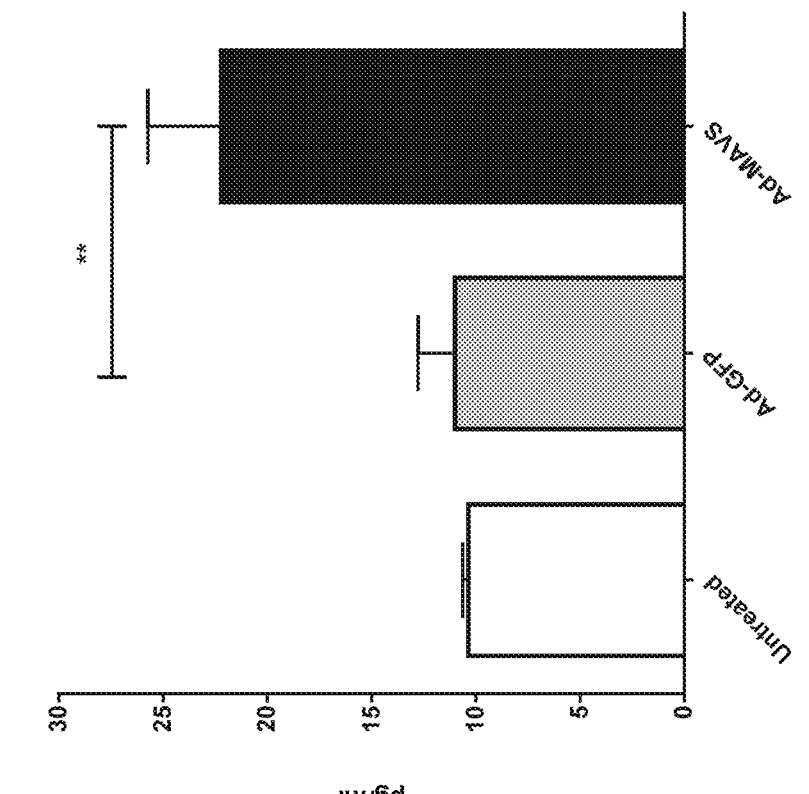
Figure 2B:
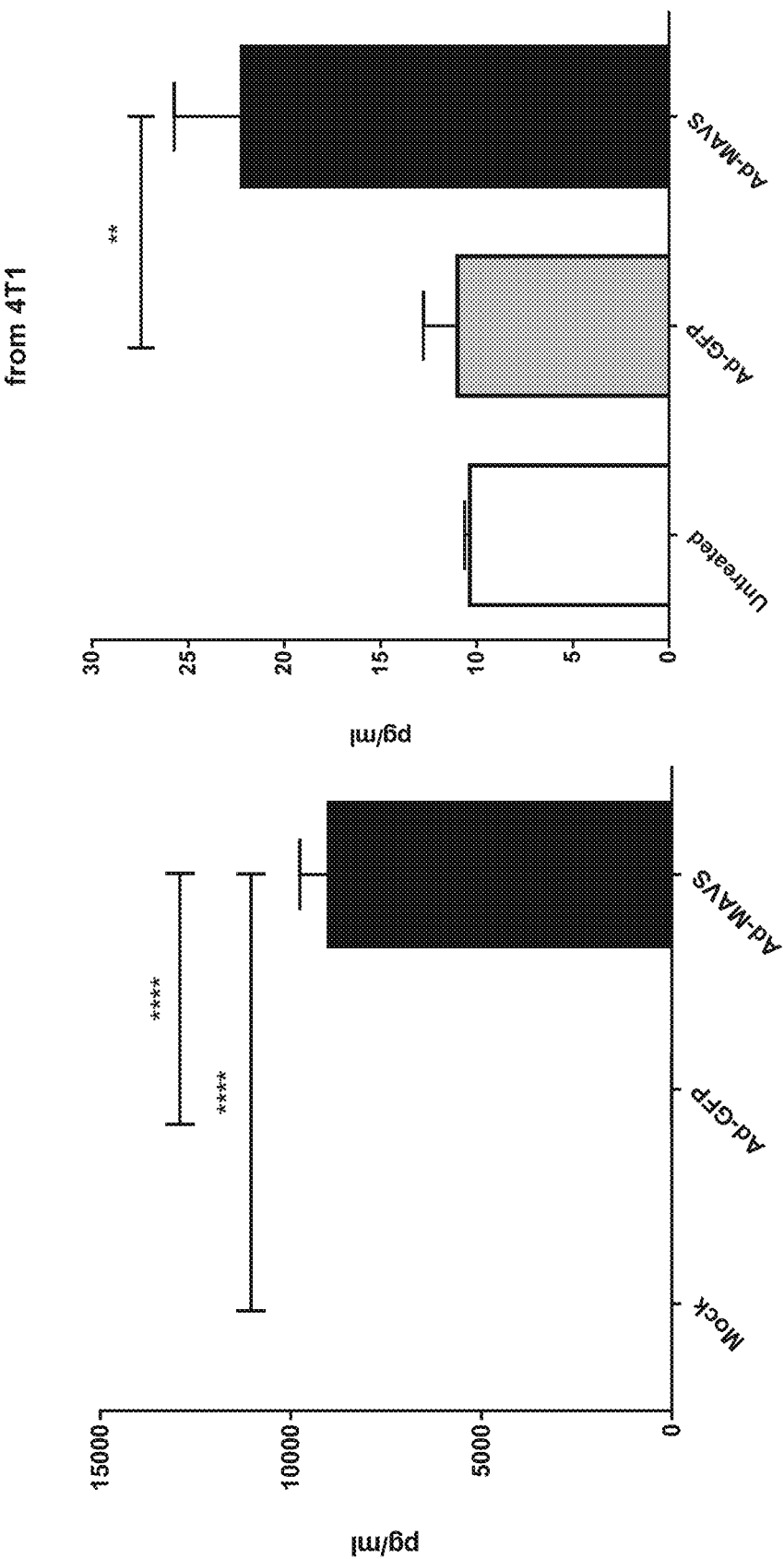

While the use of immune checkpoint blockade and other immunotherapies have gained significant traction as viable therapies for certain cancers, many tumors remain refractory to these immunotherapies due to their highly immunosuppressive microenvironment. This is perhaps best exemplified in the largest group of cancers, colorectal carcinomas (CRCs) where ~90% of CRCs (non-microsatellite instable) are unresponsive to immune checkpoint blockade. As a novel approach to boost local anti-tumor immunity and sensitize cancers to these therapies, the present inventors, in the non-limiting Examples, have demonstrated that overexpressing the innate signaling adaptor molecule, Mitochondrial Antiviral Signaling protein (MAVS), in several different types of cancerous and non-cancerous cells results in innate immune signaling downstream of the RIG-I like receptors (RLRs). Such RLR signaling, without being limited by theory, results in the activation of multiple signaling pathways as well as the release of a Th1 cytokine milieu and type I interferons. The present inventors furthermore demonstrate that overexpression of the MAVS protein in the tumor microenvironment produces robust inflammatory signaling which alters the tumor microenvironment to both efficiently suppress tumor growth and stimulate anti-tumor immune responses. Accordingly, overexpression of MAVS protein in cancerous and/or non-cancerous cells may be effective as a monotherapy as MAVS overexpression has significant anti-tumor properties but MAVS overexpression may also be combined with other anti-cancer therapeutic agents.

Mitochondrial Antiviral Signaling protein (MAVS) polypeptides are provided. The MAVS polypeptides may be any Mitochondrial Antiviral Signaling protein (MAVS) found in a particular species or a variant thereof. In some embodiments, the MAVS polypeptides may have at least 50%, 55%, 60%, 65%, 70%, 75%, 80%, 85%, 90%, 95%, 98%, or 99% sequence identity to SEQ ID NO: 1 (human MAVS protein), SEQ ID NO: 2 (mouse MAVS protein), or a homolog thereof.

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The MAVS polypeptides disclosed herein may further include one or more transport moieties. As used herein, a "transport moiety" may be an amino acid or non-amino acid moiety that aids in transporting a MAVS polypeptide across a cell membrane. Examples of transport moieties may include, without limitation, a Vesicular Stomatitus Virus glycoprotein (VSV-G), cell penetrating peptides (such as Trans-Activator of Transcription (TAT) peptide or penatrin), etc.

The MAVS polypeptides disclosed herein may include "mutant" MAVS polypeptides and variants, mutants, and derivatives thereof. As used herein the term "wild-type" is a term of the art understood by skilled persons and means the typical form of an organism, strain, gene or characteristic as it occurs in nature as distinguished from mutant or variant forms. As used herein, a "variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a MAVS polypeptide mutant or variant molecule may have one or more insertions, deletions, or substitution of at least one amino acid residue relative to the MAVS "wild-type" polypeptide sequence of a particular organism. The polypeptide sequence of the "wild-type" MAVS protein from humans is presented as SEQ ID NO:1 while the polypeptide sequence of the "wild-type" MAVS protein from mice is presented as SEQ ID NO: 2. These sequences may be used as reference sequences.

The MAVS polypeptides provided herein may be full-length polypeptides or may be fragments of the full-length polypeptide. As used herein, a "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 155 contiguous amino acid residues of a reference polypeptide, respectively. In some embodiments, a fragment may comprise at least 5, 10, 15, 20, 25, 30, 40, 50, 60, 70, 80, 90, 100, or 150 contiguous amino acid residues of a reference polypeptide. Fragments may be preferentially selected from certain regions of a molecule. The term "at least a fragment" encompasses the full length polypeptide. A fragment of a MAVS polypeptide may comprise or consist essentially of a contiguous portion of an amino acid sequence of the full-length MAVS polypeptide (SEQ ID NO: 1 or SEQ ID NO: 2). A fragment may include an N-terminal truncation, a C-terminal truncation, or both truncations relative to the full-length FGF polypeptide. Preferably, a fragment of a MAVS polypeptide includes the amino acid residues responsible for the TLR adaptor signaling function of the MAVS polypeptide.

A "deletion" in a polypeptide refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a MAVS polypeptide may have N-terminal insertions, C-terminal insertions, internal insertions, or any combination of N-terminal insertions, C-terminal insertions, and internal insertions.

Regarding polypeptides, the phrases "% sequence identity," "percent identity," and "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent sequence identity for amino acid sequences may be determined as understood in the art. (See, e.g., U.S. Pat. No. 7,396,664, which is incorporated herein by reference in its entirety).

As described herein, variants, mutants, or fragments (e.g., a MAVS polypeptide variant, mutant, or fragment thereof) may have 99%, 98%, 97%, 96%, 95%, 94%, 93%, 92%, 91%, 90%, 80%, 70%, 60%, or 50% amino acid sequence identity relative to a reference molecule (e.g., relative to the MAVS full-length polypeptide (SEQ ID NO: 1 or SEQ ID NO: 2)).

The amino acid sequences of the MAVS polypeptide variants, mutants, or derivatives as contemplated herein may include conservative amino acid substitutions relative to a reference amino acid sequence (e.g., SEQ ID NO: 1 or SEQ ID NO: 2). For example, a variant, mutant, or derivative MAVS polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

It will also be appreciated by those of skill in the art that the "wild-type" MAVS protein sequences from different organisms may be aligned to determine amino acid positions within the protein that may altered in order to create variant or mutant forms of the protein that may be expected to retain the activity of the MAVS protein.

The disclosed MAVS polypeptides, mutants, or variants described herein may have one or more functional or biological activities exhibited by a reference polypeptide (e.g., one or more functional or biological activities exhibited by SEQ ID NO: 1 or SEQ ID NO: 2). Preferably, a mutant or variant of a MAVS polypeptide retains the TLR adaptor signaling function of the MAVS polypeptide.

Polynucleotides encoding any of the MAVS polypeptides disclosed herein are also provided. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Suitably the polynucleotide encodes the full-length polypeptide, however, polynucleotides encoding partial polypeptides are also provided.

Isolated polynucleotides homologous to the polynucleotides described herein are also provided. Those of skill in the art also understand the degeneracy of the genetic code and that a variety of polynucleotides can encode the same polypeptide. In some embodiments, the polynucleotides may be codon-optimized for expression in a particular cell. While particular nucleotide sequences which are found in humans are disclosed herein any nucleotide sequences may be used which encode a desired form of the substituted polypeptides described herein. Thus non-naturally occurring sequences may be used. These may be desirable, for example, to enhance expression in heterologous expression systems of polypeptides or proteins.

The polynucleotides may further include heterologous promoters or enhancers operably connected to the polynucleotides to allow for expression of the polynucleotide in an appropriate host cell. As used herein, a "heterologous promoter" refers to any promoter not naturally associated with a polynucleotide to which it is operably connected. Promoters useful in the practice of the present invention include, without limitation, constitutive, inducible, temporally-regulated, developmentally regulated, chemically regulated, physically regulated (e.g., light regulated or temperature-regulated), tissue-preferred, and tissue-specific promoters. Promoters may include pol I, pol II, or pol III promoters. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Those of skill in the art are familiar with a wide variety of additional promoters for use in various cell types.

In some embodiments, the polynucleotides encoding the MAVS polypeptides disclosed herein further include an inducible promoter operably connected to the polynucleotide.

The isolated polynucleotides or polypeptides provided herein may be prepared by methods available to those of skill in the art. Isolated indicates that the polynucleotides or proteins are not in their naturally occurring state. Such preparations may be cell-free preparations. The polynucleotide or polypeptides may be extracted from the cells by breaking the cell membrane and optionally removing non-desired components. The polypeptides may be made as secreted polypeptides and further isolated using means known to those of skill in the art. Alternatively, desired proteins or nucleic acids can be purified using sequence-specific reagents, including but not limited to oligonucleotide probes, primers, and antibodies. Techniques for isolating cell-free preparations are well known in the art, and any that are convenient can be used. The term "substantially isolated or purified" refers to polypeptides or polynucleotides that are removed from their natural environment, and are at least 60% free, preferably at least 75% free, and more preferably at least 90% free, even more preferably at least 95% free from other components with which they are naturally associated.

In some embodiments, polynucleotides including a first heterologous promoter operably connected to a first polynucleotide encoding any one of the MAVS polypeptides described herein are provided.

The polynucleotides of the present invention invention may also include a first heterologous promoter operably connected to a first polynucleotide encoding any one of the MAVS polypeptides described herein and a second polynucleotide encoding a cancer antigen operably connected to the first promoter or a second promoter.

The cancer antigen may be any antigen that is capable of eliciting an immune response to a cancer or tumor. In some embodiments, the cancer antigen may be an ESR1 polypeptide, mutant or portion thereof; a HER3 polypeptide, mutant or portion thereof; a mutant HER2 polypeptide or portions thereof, and combinations thereof. Such HER3, HER2, and ESR1 antigens are provided, for example, in U.S. Patent Publication 2014/0377261, and International Application Publications WO 2016/007499 and WO 2016/007504.

The second polynucleotide encoding a cancer antigen may also be fused in frame to a third polynucleotide encoding fusion partners such as fusion polynucleotides or polypeptides which provide additional functionality to the antigenic cargo. In some embodiments, the polynucleotide constructs described herein include a second polynucleotide encoding a cancer antigen that is fused in frame to a third polynucleotide encoding a lactadherin polypeptide or portions thereof. Lactadherin is a protein that is trafficked to exosomes though its C1C2 domain, a lipid binding domain. The lactadherin polypeptide may include SEQ ID NOS: 3-6 (leader sequences and C1C2 domains of mouse and human lactadherin) or a homolog thereof.

In another embodiment the polynucleotides constructs or the encoded polypeptides may be fused with polynucleotides or their encoded polypeptides to allow delivery to and/or fusion with the cell. For example, fusion with a Herpes Simplex Virus VP16 may allow for the cellular delivery of the antigenic polypeptide. Other potential fusion protein partners are ligands for receptors found on the target cells such that the peptides will be taken up by the cells via receptor-mediated endocytosis.

The polypeptides described herein may also be altered to make them more stable for delivery. Polypeptides may also be circularized or dimerized using any other means known to those of skill in the art. Addition of a methionine to the N-terminus of the polypetides provided herein can be used as a target to generate a circularized peptide using the method of Tam and Xu (Biopolymers (1998) Methionine ligation strategy in the biomimetic synthesis of parathyroid hormones 46: 319-329). The polypeptides may have substituents bonded to either terminus of the peptide. For example, the peptide may have an acetyl or a carbamyl addition at the N-terminus, and/or an amide addition at the C-terminus. Those of skill in the art will appreciate that various additional modifications of the polypeptides provided herein may be made to increase the stability or half-life of the peptides in culture or in the subject after administration. For example fatty acids or other modifications may be added to the N-terminus including but not limited to formylation, myristoylation, or PEGylation. The polypeptide may be attached to a carrier protein to increase the stability of the peptide. The carrier protein-peptide may be a fusion protein and may be expressed as a recombinant protein using techniques available to those of skill in the art. The peptide bonds connecting the amino acids of the polypeptide may be altered or at least one peptide bond may be altered to make the peptides more resistant to degradation, for example a methyl group could be added. The amino acids could be replaced with functionally related non-natural amino acid that share similar side chains to the natural amino acid, such as replacement of the cysteine with homocysteine or α-methyl-cysteine.

Vectors including any one of the polynucleotides described herein are provided. The vectors may include an origin of replication suitable to allow maintenance of the polynucleotide within a prokaryotic or eukaryotic host cell or within a viral nucleic acid. The vector may be viral vectors including, without limitation, an adenovirus, adeno-associated virus, fowlpox, vaccinia, viral equine encephalitis virus, or venezuelan equine encephalitis virus. In some embodiments, the vector is a DNA-based plasmid vector.

In some embodiments, the vector may be a gene therapy vector. As used herein, a "gene therapy vector" may be any vector that is being used to deliver a polynucleotide into cells within a subject.

The vector may also be mini-circle DNA (mcDNA) vectors. Mini-circle DNA vectors are episomal DNA vectors that are produced as circular expression cassettes devoid of any bacterial plasmid DNA backbone. See, e.g. System Biosciences, Mountain View Calif., MN501A-1. Their smaller molecular size enables more efficient transfections and offers sustained expression over a period of weeks as compared to standard plasmid vectors that only work for a few days. The minicircle constructs can be derived from a plasmid with a bacterial origin of replication and optionally antibiotic resistance genes flanked by att sites to allow for recombination and exclusion of the DNA between the att sites and formation of the minicircle DNA.

Compositions including any of the MAVS polypeptides or polynucleotides and an anti-cancer therapeutic agent are also provided. In some embodiments, the anti-cancer therapeutic agent includes an agent targeting HER2, HER1, estrogen receptor, EGFR, or IGF1R.

The anti-cancer therapeutic agent may be any therapeutic agent that is used to treat cancer in a subject. Suitable anti-cancer therapeutic agents may include, without limitation, radiation, chemotherapy agents, anti-cancer biologics, or immunotherapy agents. Chemotherapy agents are chemotherapeutic compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25.

Anti-cancer biologics are biomolecules (e.g., polynucleotides, polypeptides, lipids, or carbohydrates) that may be used to treat cancer. Anti-cancer biologics may include, without limitation, cytokines such as IL-1α, IL-2, IL-2β, IL-3, IL-4, CTLA-2, IFN-α, IFN-γ, granulocyte-macrophage colony stimulating factor (GM-CSF), IL-12, IL-23, IL-15, IL-7, or any combination thereof; or anti-cancer antibodies such as Rituximab, Trastuzumab, Gemtuzumab, Alemtuzumab, Ibritumomab tiuxetan, Tositumomab, Cetuximab, Bevacizumab, Panitumumab, Ofatumumab, Brentuximab Vedotin, Pertuzumab, Adotrastuzumab emtansine, Lapatinib, Erlotanib, and Obinutuzumab.

Figure 6L:
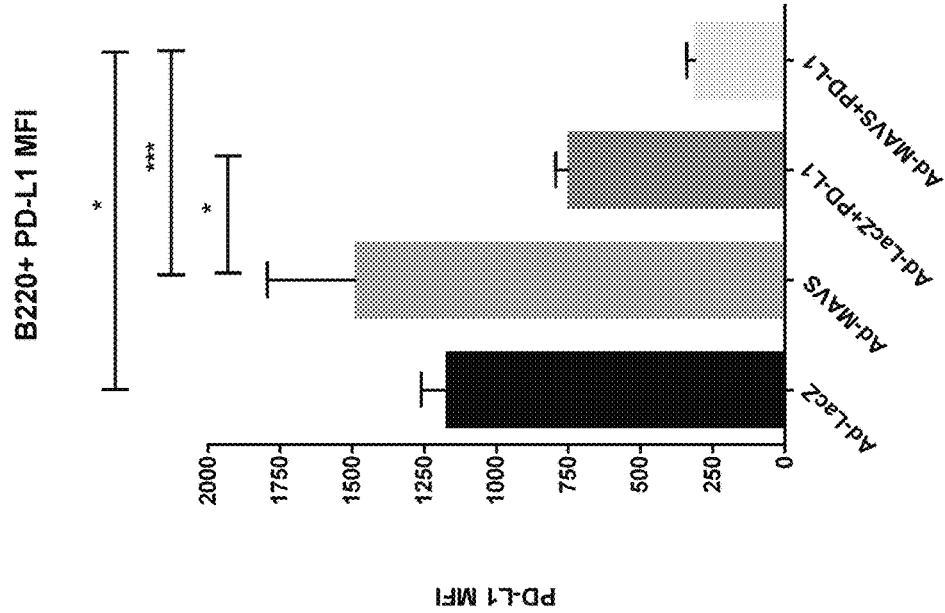
Figure 6M:
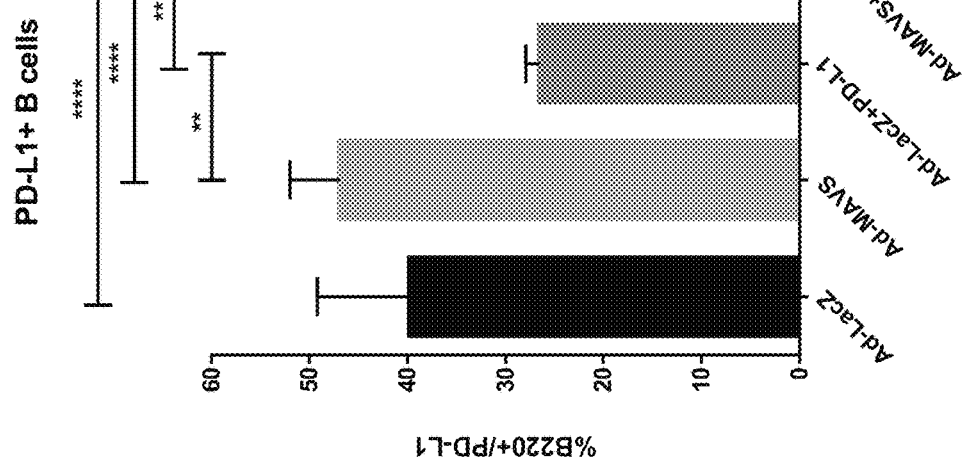
Figures 7A, 7B:
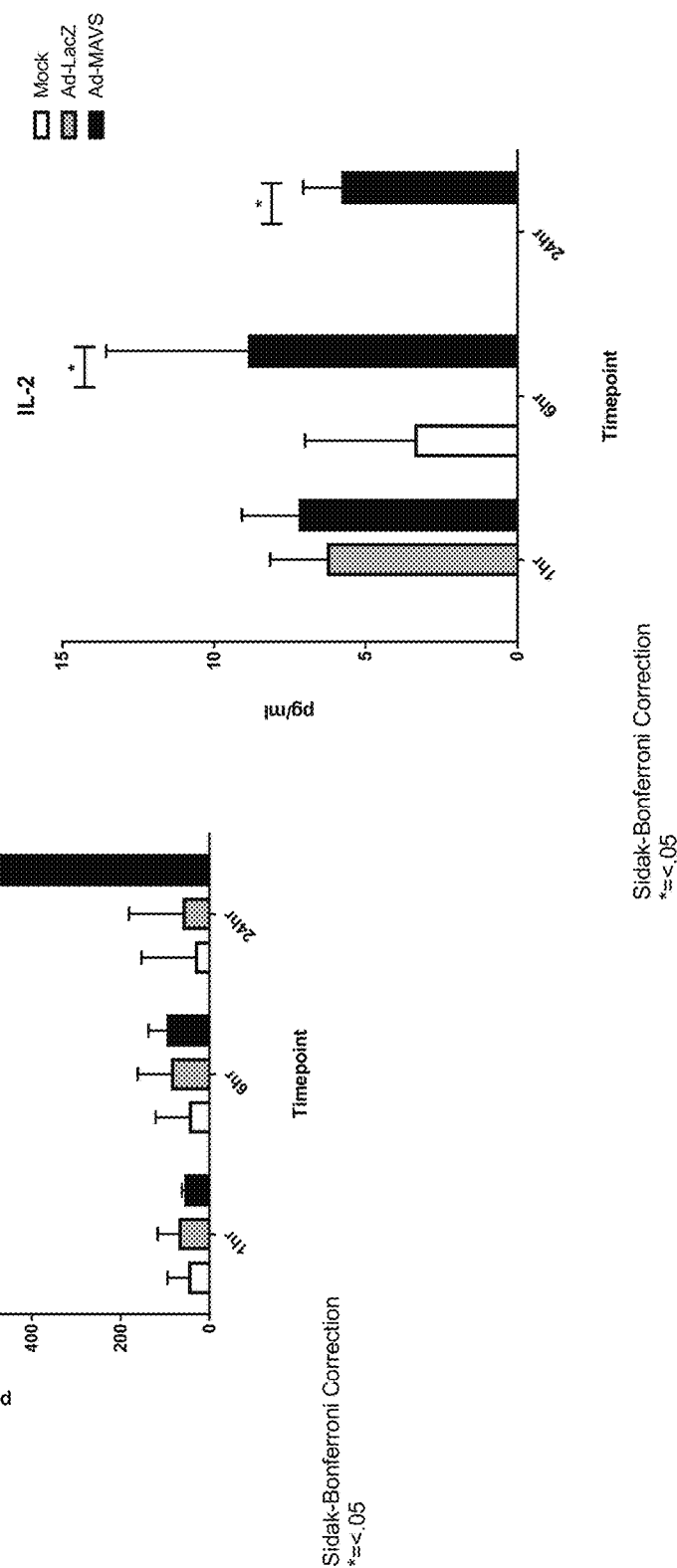
Figures 7C, 7D:
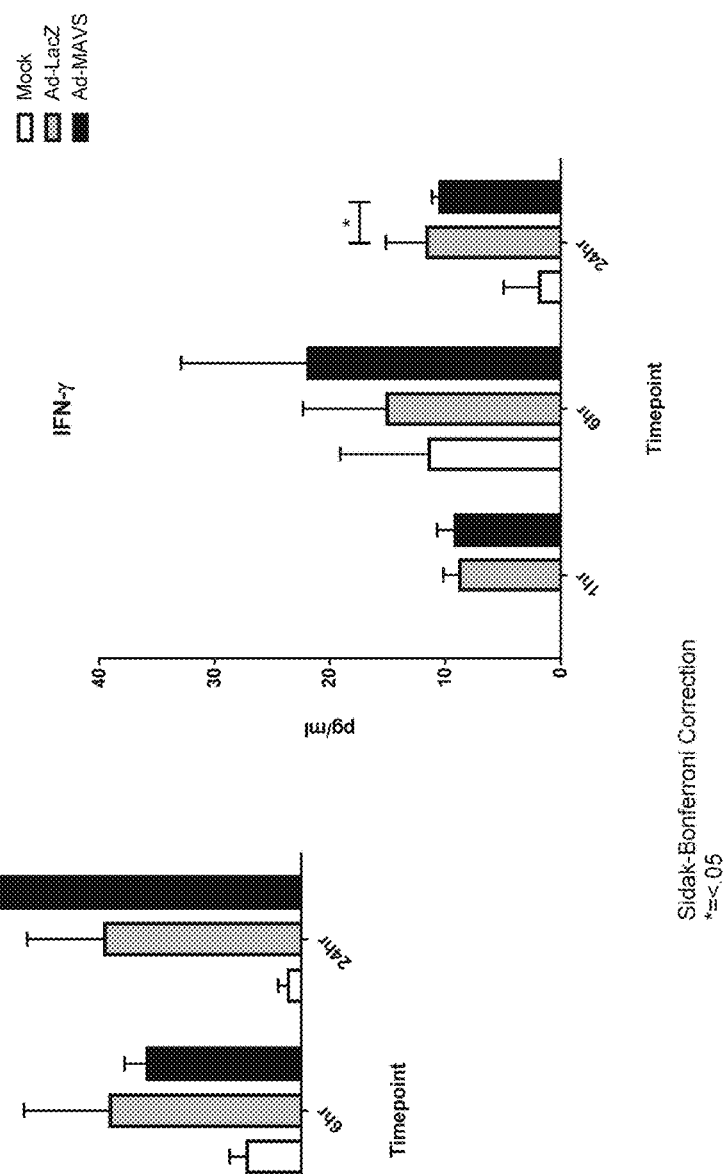
Figure 7K:
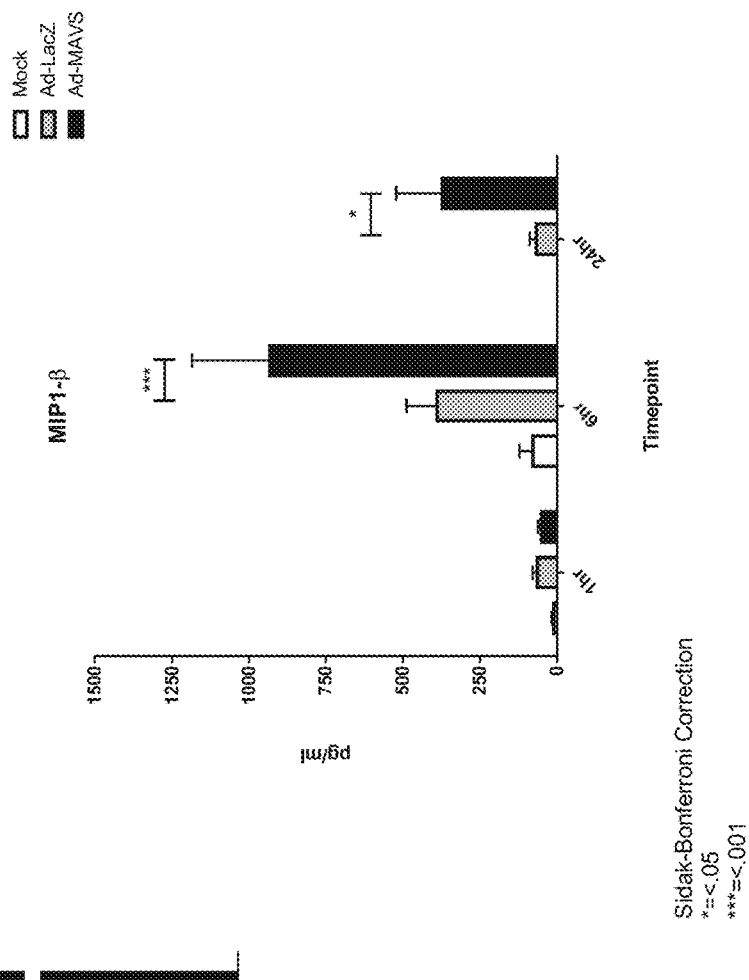
Figure 7L:
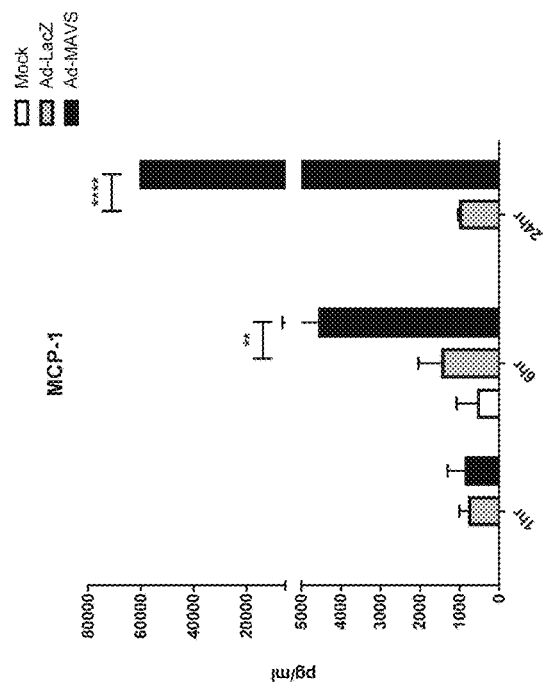
Figures 9A, 9B:
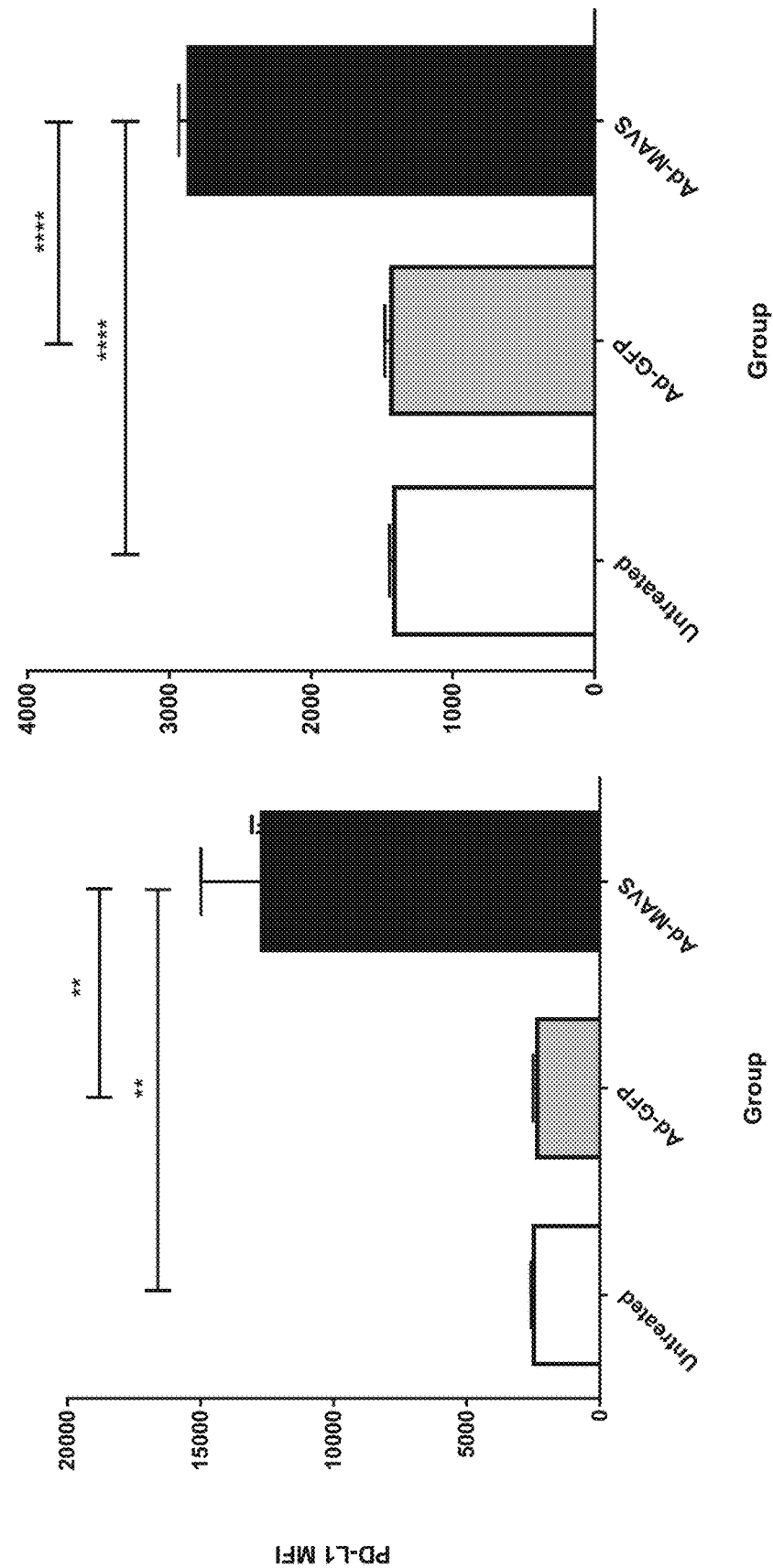
Figure 10B:
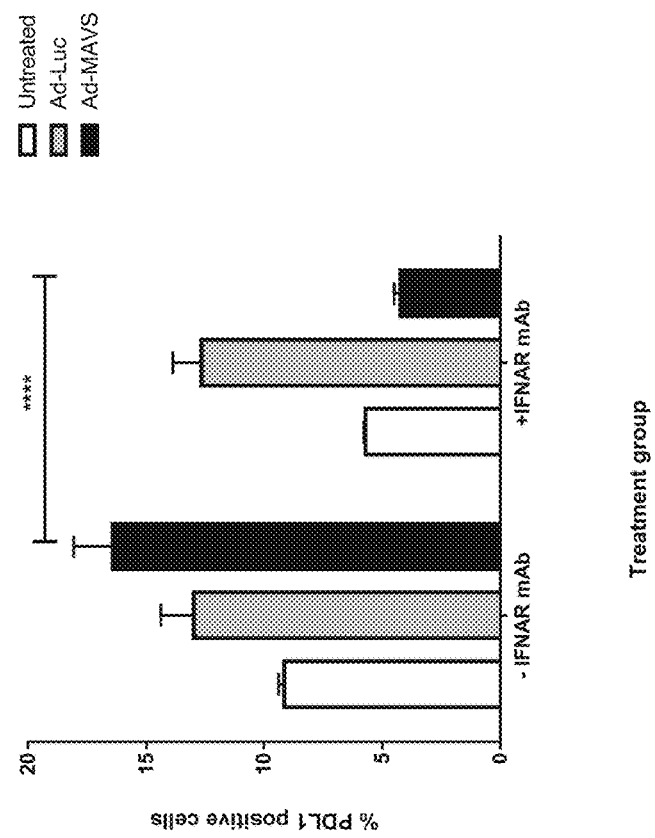
Figure 10A:
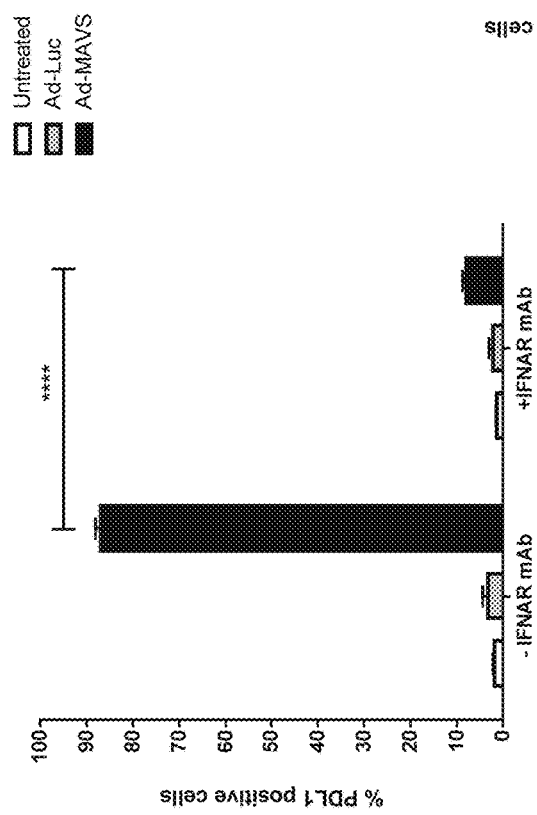
Figure 10D:
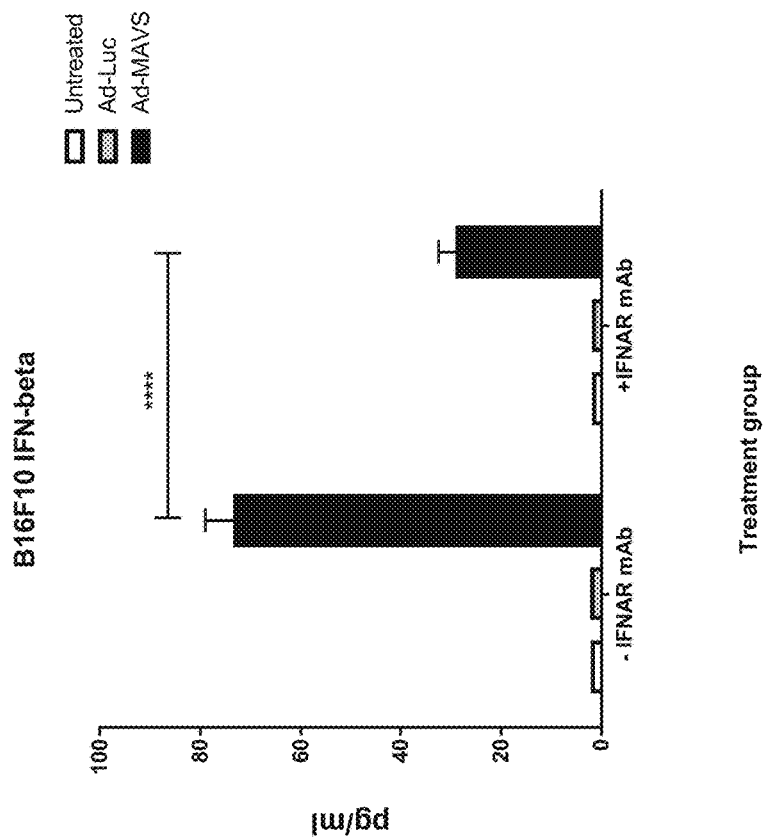
Figure 10C:
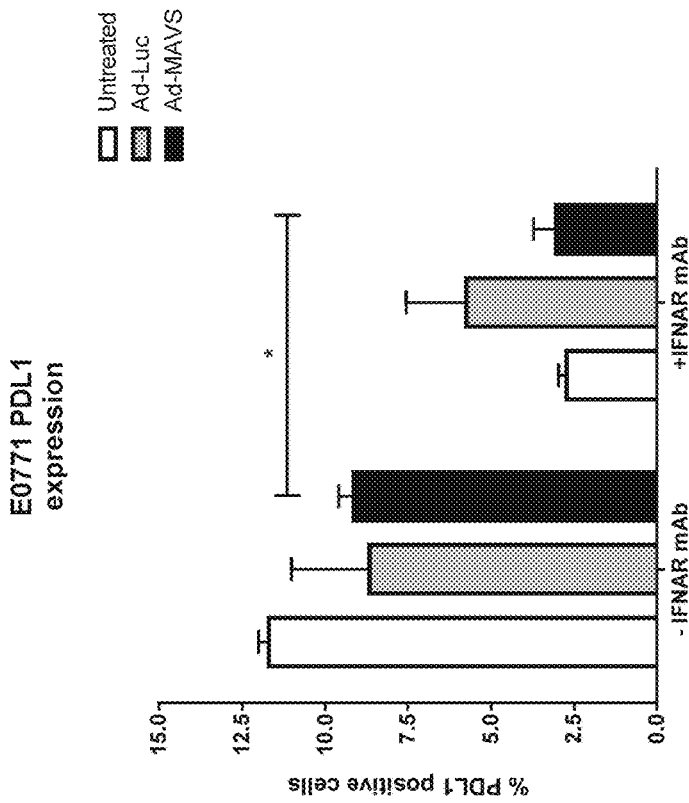
Figure 10I:
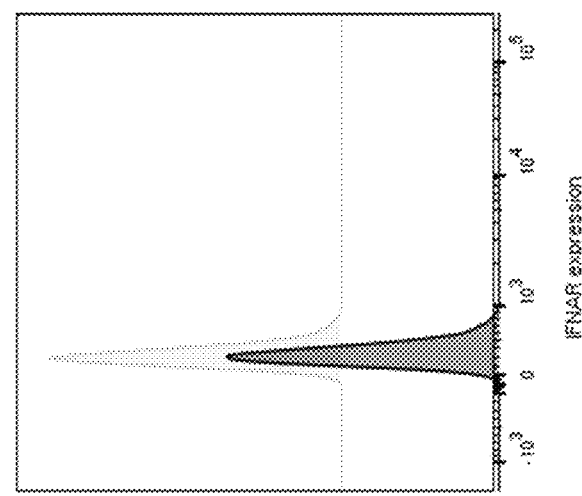
Figure 10H:
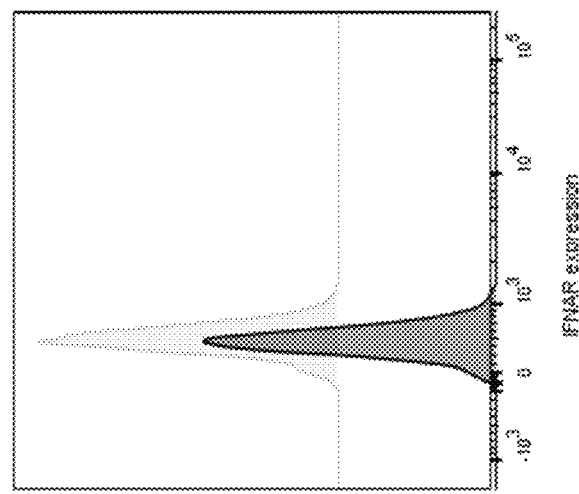
Figure 10G:
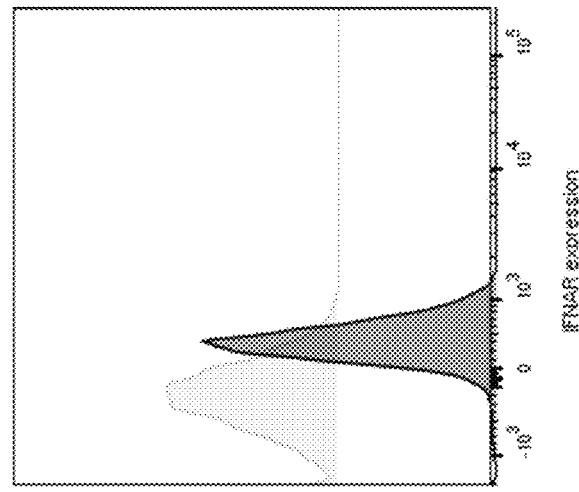
Figure 11A:
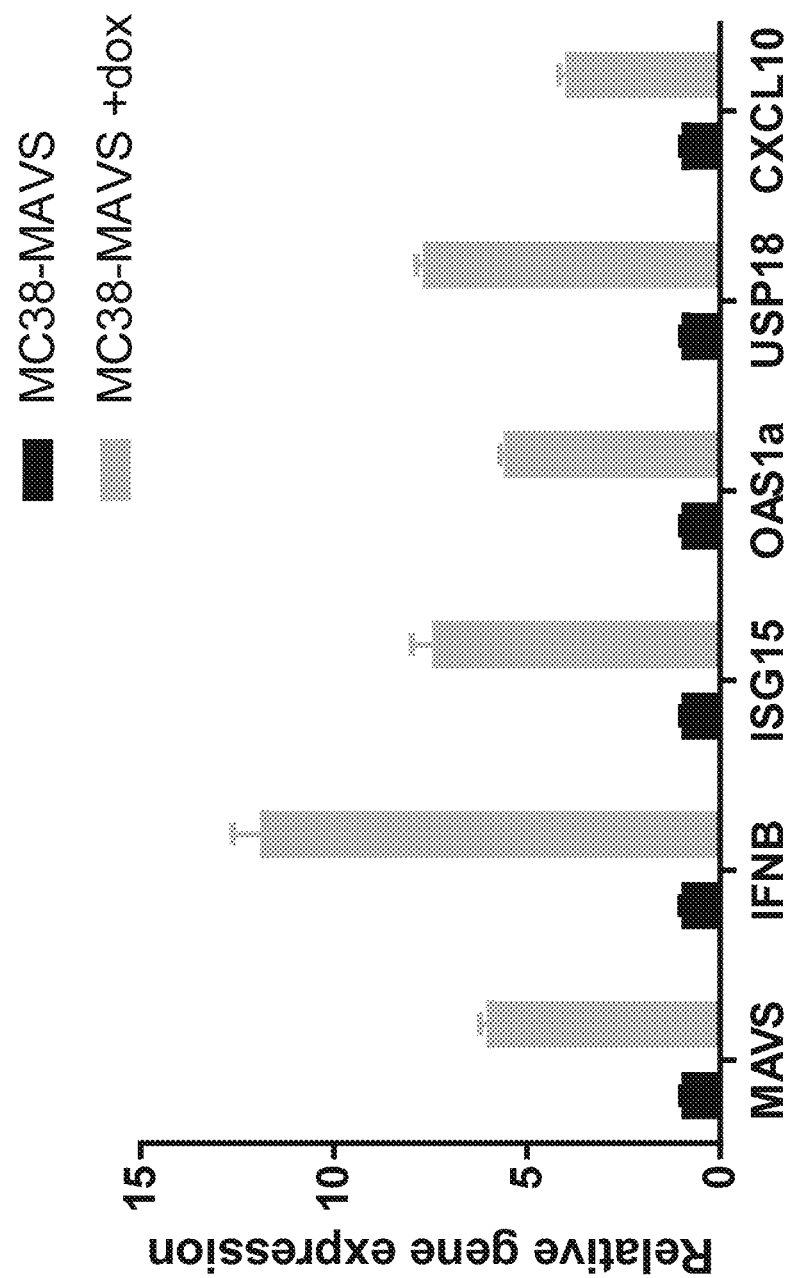
FIGS. 11A-11D show activation of innate immune adaptor MAVS induces innate immunity in colorectal cancer cells.
Figure 11B:
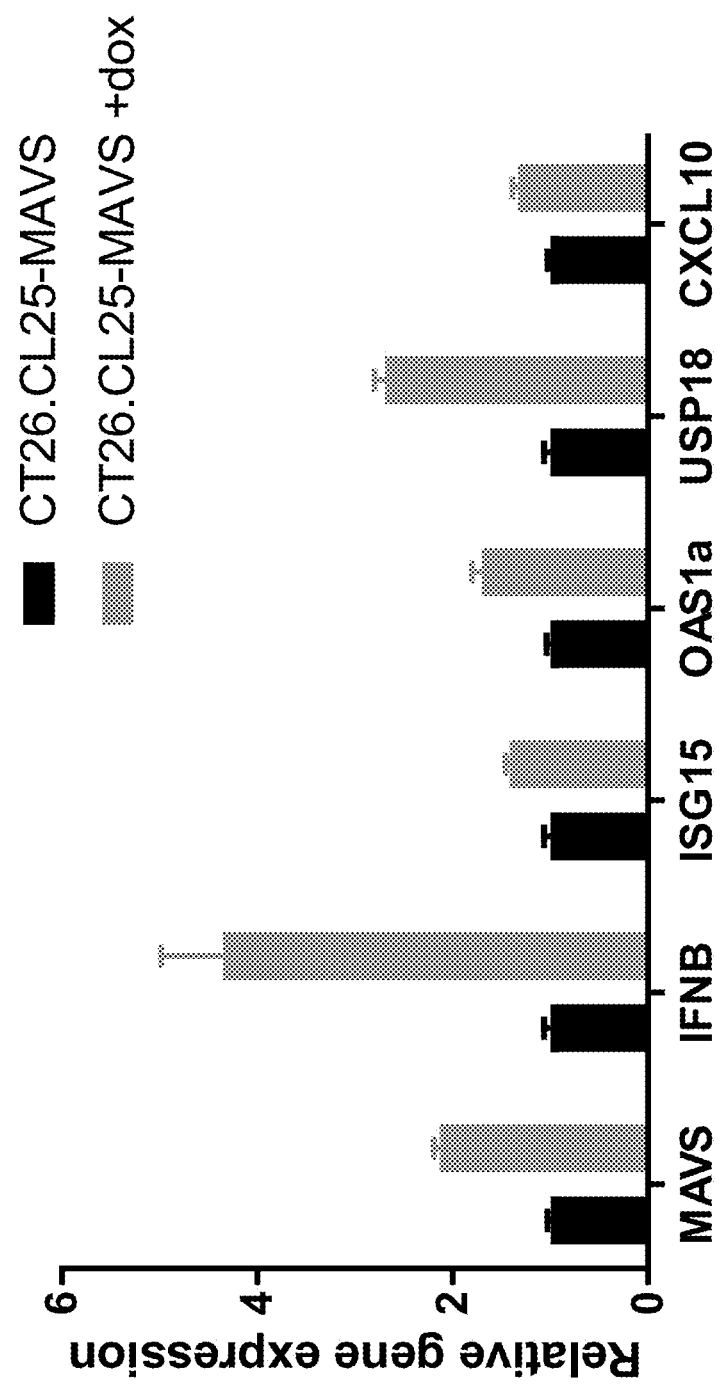
Figure 11C:
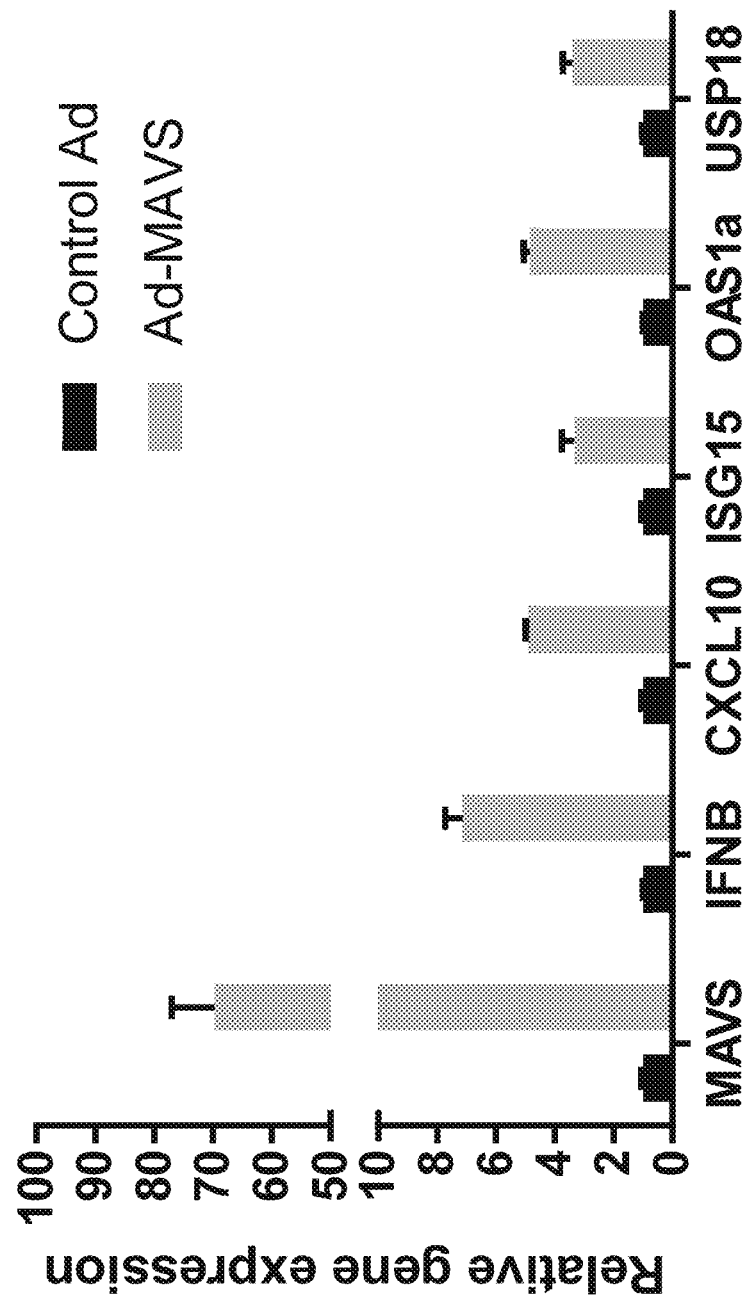
Figure 11D:
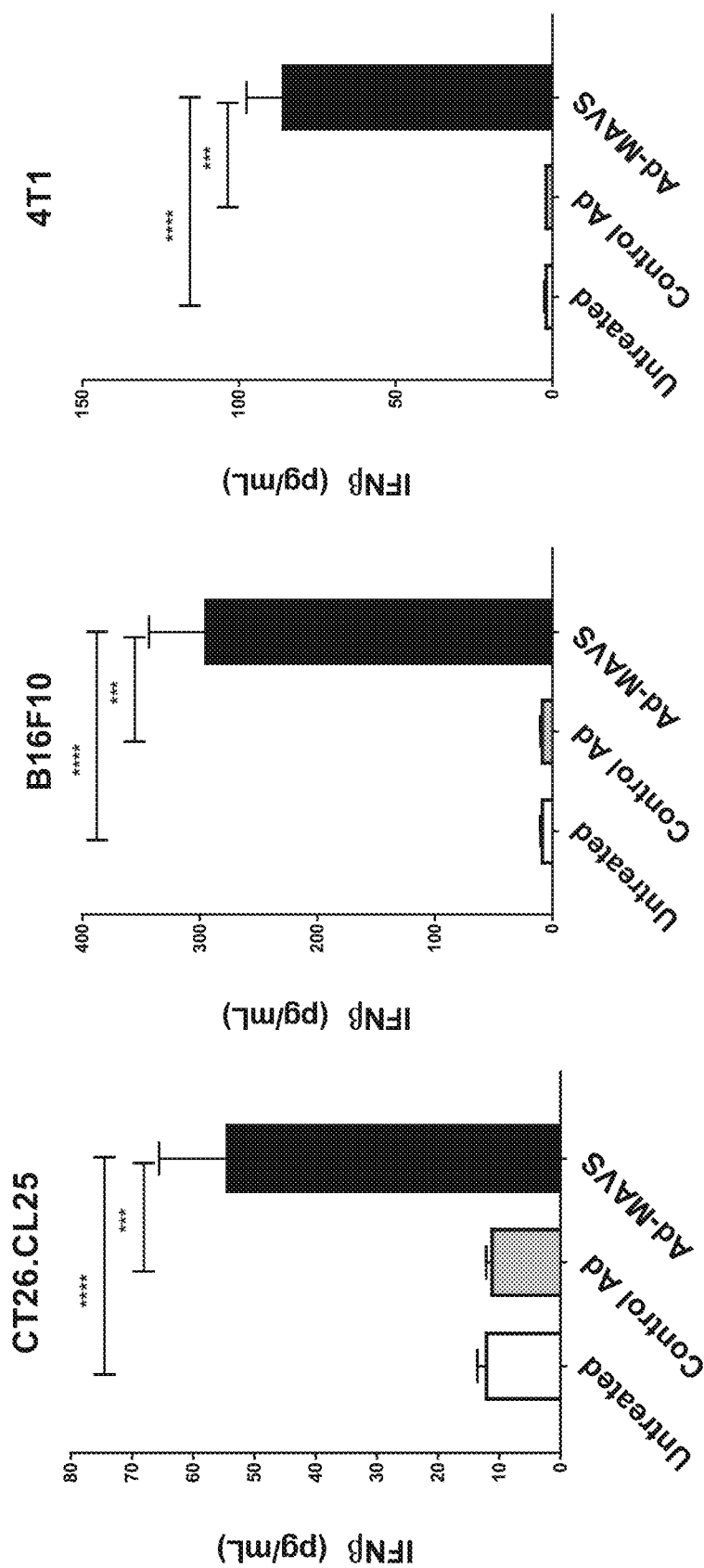
Figure 12A:
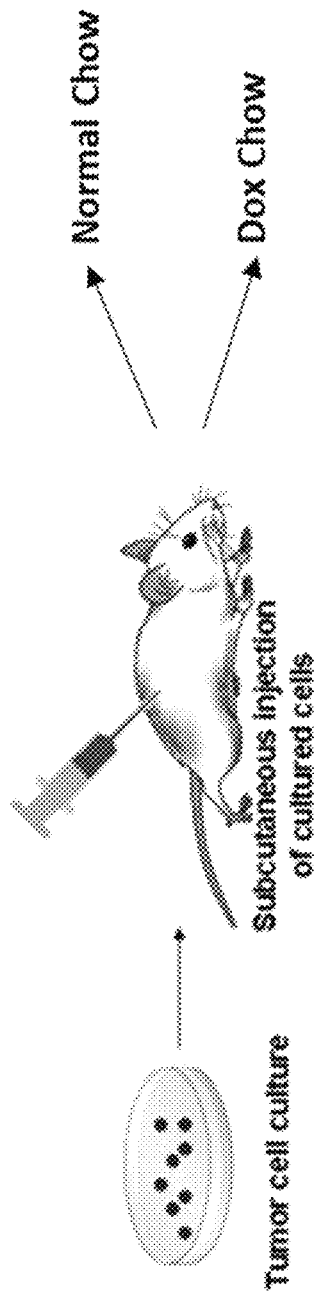
Figure 12B:
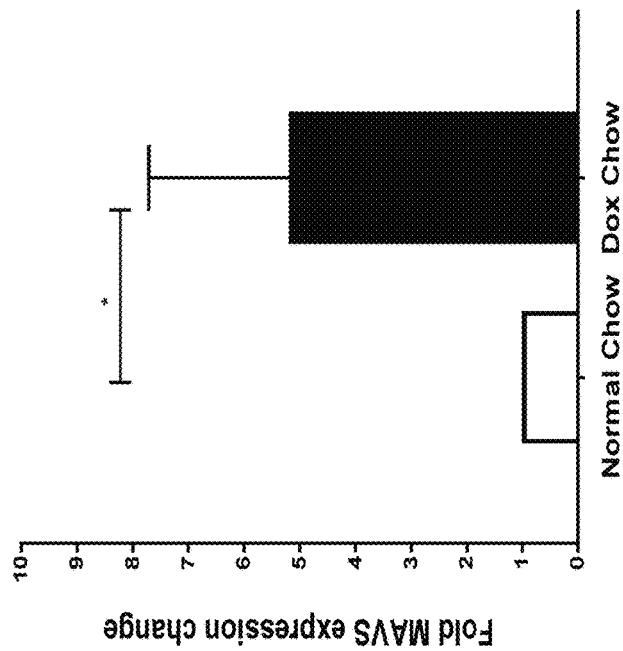
Figure 12D:
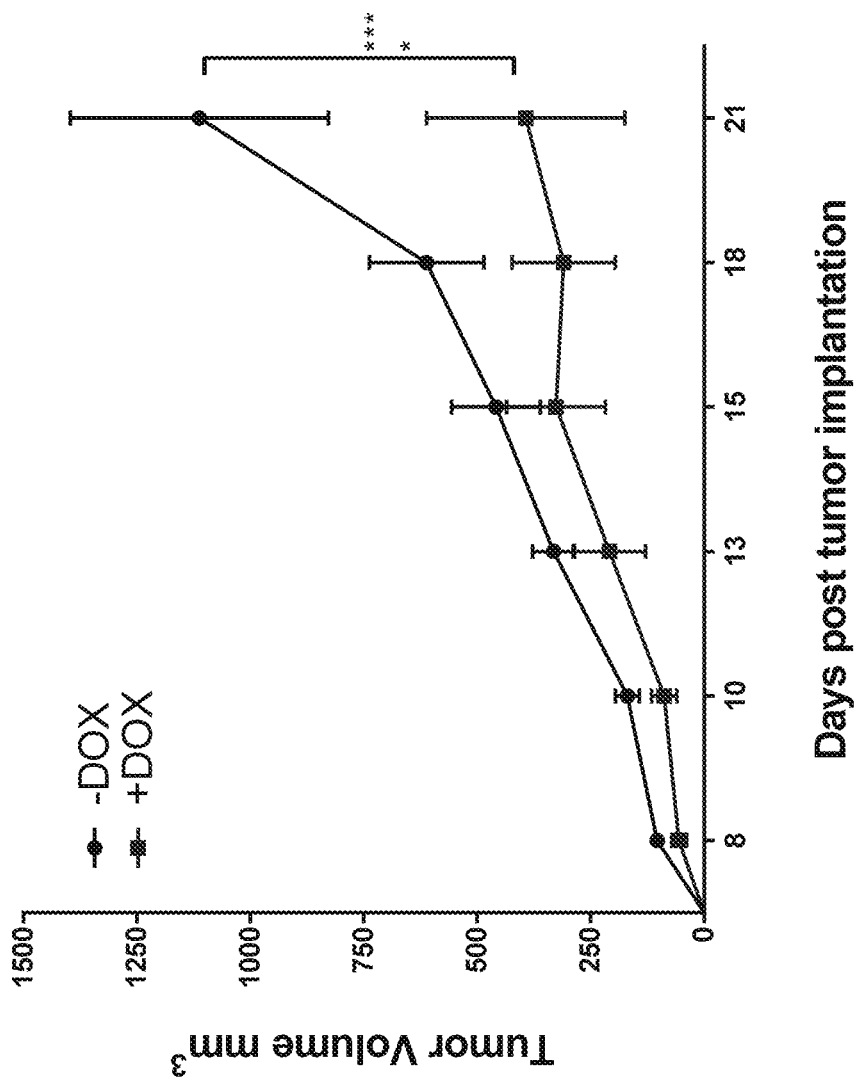

The term "immunotherapy agent(s)" refers to any therapeutic that is used to treat cancer in a subject by inducing and/or enhancing an immune response in that subject. Immunotherapy agents may include, without limitation, checkpoint inhibitors, cancer vaccines, immune cells such as engineered T cells, anti-cancer viruses, or bispecific antibodies. Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment. Checkpoint inhibitors, however, are not effective against all cancer types. Furthermore, not every patient that is expected to respond to immune checkpoint blockade actually benefits from treatment with such agents. In part, the present inventors have found that MAVS overexpression results in immunoregulatory feedback via PD-L1 and that the combined treatment with Ad-MAVS and PD-L1 inhibition leads to robust anti-tumor immunity. See, e.g., FIGS. 5-6. Thus, patients that do not respond to the administration of checkpoint inhibitors alone may benefit from administration of a checkpoint inhibitor(s) and MAVS overexpression.

Exemplary checkpoint inhibitors include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (Merck MK-3475), nivolumab (Bristol-Myers Squibb BMS-936558), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb) and tremelimumab (Pfizer).

Cancer vaccines stimulate the body's immune system to attack cancer cells. Cancer vaccines generally include a tumor antigen in an immunogenic formulation that activates tumor antigen-specific helper T cells and/or cytotoxic T cells and B cells. Vaccines can be in a variety of formulations, including, without limitation, dendritic cells, monocytes, viral, liposomal and DNA vaccines. Suitably, the dendritic cells are autologous and transfected with tumor cells or tumor antigens. Dendritic cells are immune cells that present antigens to T cells, which prompted their application in therapeutic cancer vaccines. Following the loading of dendritic cells with tumor antigens ex vivo, the dendritic cells may be administered as a cellular vaccine which has been found to induce protective and therapeutic anti-tumor immunity. Exemplary cancer vaccines include, without limitation, Sipuleucel-T (Provenge®, or APC8015). Sipuleucel-T is an FDA-approved cancer vaccine developed from autologous dendritic cells (DC) loaded with engineered fusion protein of prostatic acid phosphatase (PAP) and granulocyte-macrophage colony-stimulating factor (GM-CSF).

An immunotherapy agent may include immune cells (i.e., T cells or B cells) that are adoptively transferred into a subject to attack or reduce cancer cells or cancer cell growth. The immune cells may be autologous or derived from a subject that is different from the subject receiving the immune cells and modified to reduce rejection. The immune cells may also have a natural or genetically engineered reactivity to a subject's cancer. For example, natural autologous T cells have been shown to be effective in treating metastatic cancers. See, e.g., Rosenberg S A et al., Nat. Rev. Cancer 8 (4): 299-308 (2008). Natural autologous T cells may be found within a resected subject's tumor. Such T cells can be induced to multiply in vitro using high concentrations of IL-2, anti-CD3 and allo-reactive feeder cells. These T cells are then transferred back into the subject along with, for example, exogenous administration of IL-2 to further boost their anti-cancer activity.

The T cells may also include engineered T cells. Engineered T cells are T cells that have been genetically modified so as to direct T cells to specifically destroy a subject's cancer cells. Engineered T cells may, for example, include T cells that have been genetically modified to express chimeric antigen receptor (CAR) proteins or "CAR T cells." See, e.g., Liddy et al., *Nature Med.* 18:980-7 (2012); Grupp et al., *New England J. Med.* 368:1509-18, (2013). The CAR proteins may include a targeting moiety such as an extracellular single-chain variable fragment (scFv) capable of binding a tumor-associated antigen(s), a transmembrane domain, and intracellular signaling/activation domain(s). The intracellular signaling/activation domain(s) may include, without limitation, CD3ζ signaling domain, 41BB-signaling domains, CD28-signaling domains, or combinations thereof. Suitable tumor-associated antigens include, without limitation, CD19, carcinoembryonic antigen (CEA), diganglioside GD2, mesothelin, L1 cell adhesion molecule (L1CAM), human epidermal growth factor receptor 2 (HER2), fibroblast activation protein (FAP), interleukin 13 receptor α (IL13Rα), EGFR, or EGFR variant 3 (EGFRvIII).

CAR T cells have demonstrated remarkable success in treating blood-borne tumors such as certain kinds of leukemias. CAR T cells, however, have not been as effective at treating solid tumors, which present a number of unique barriers that are absent in blood-borne malignancies. For example, unlike the environment of blood-borne malignancies, CAR T cells must successfully traffic to solid tumor sites in spite of tumor signaling attempting to inhibit such trafficking. Furthermore, once trafficked to a tumor, CAR T cells must infiltrate into the solid tumor in order to elicit tumor-associated antigen-specific cytotoxicity. Even after successful trafficking and infiltration, CAR T cells must evade the immunosuppressive microenvironment of the tumor conferred by, for example, suppressive immune cells (regulatory T cells (Tregs), myeloid-derived suppressor cells (MDSC), tumor-associated macrophages (TAMs), and/or neutrophils (TAN). The present inventors have demonstrated that overexpressing MAVS protein in cells may dampen the immunosuppressive microenvironment in tumors. Given this ability to dampen the immunosuppressive microenvironment in tumors, the present inventors expect that T cell therapy such as CAR T cell therapy may be improved by also overexpressing MAVS protein in cancer or non-cancerous cells.

An immunotherapy agent may include an oncolytic virus. As used herein, an "oncolytic virus" refers to any virus that may be used to treat cancer. Exemplary oncolytic viruses include, without limitation, PVS-RIPO, T-VEC, and Onyx-015. PVS-RIPO is a genetically modified oral poliovirus that has been fast-tracked by the FDA for the treatment of recurrent glioblastoma multiforme (GBM). T-VEC (Imlygic) is an FDA-approved oncolytic virus for the treatment of melanoma in patients with inoperable tumors. Onyx-015 is an oncolytic adenovirus.

Bispecific antibodies may also be used as an immunotherapy agent in accordance with the present invention. A bispecific antibody is an antibody having binding sites for a tumor-associated antigen and for a T-cell surface receptor that can direct the lysis of specific tumor cells by T cells. Bispecific antibodies have been used, for example, to successfully treat brain tumors in human patients. See, e.g., Nitta et al., *Lancet* 355:368-371 (1990). Numerous methods to produce bispecific antibodies are known in art including, without limitation, the quadroma method (See, e.g., Milstein and Cuello, *Nature,* 305:537-540 (1983)), use of heterobifunctional cross-linkers to chemically tether two different antibodies or antibody fragments (See, e.g., Staerz et al., *Nature* 314:628-631 (1985); European Patent Application 0453082), or DOCK-AND-LOCK methods (See, e.g., U.S. Pat. Nos. 7,550,143; 7,521,056; 7,534,866; 7,527,787 and 7,666,400).

A bispecific antibody may include a trifunctional antibody that includes two heavy and two light chains, one each from two different antibodies. The two Fab regions are directed against two antigens while the Fc region is made up from the two heavy chains and forms the third binding site, which typically may elicit effector functions. A bispecific antibody may include chemically linked Fab regions, various types of bivalent and trivalent single-chain variable fragments (scFvs), or fusion proteins mimicking the variable domains of two antibodies. Suitable bispecific antibodies include, without limitation, Removab (Trion Pharma), Blincyto (Amgen), AMG-110 (Amgen), ABT-122 (Abbvie), ABT-981 (Abbvie), AFM13 (Affimed Therapeutics), MM-111 (Merrimack Pharmaceuticals), SAR156597 (Sanofi), RG7221 (Roche), RG6013 (Roche), RG7597 (Roche), ALX-0761 (Ablynx), MCLA-128 (Merus), MEDI-565 (AMG-211), MGD006 (Macrogenics), and REGN1979 (Regeneron).

Delivery particles including any one of the compositions disclosed herein are also provided. The delivery particles may be used to deliver either the MAVS polypeptide compositions or MAVS polynucleotide compositions into cells. Delivery particles suitable for delivering polynucleotides and/or proteins are known in the art and may include, without limitation, polymeric nanoparticles, liposomal nanoparticles, and nanoparticles including lipids and at least one type of polymer.

Polymeric nanoparticles have been described in the art. (See, e.g., Reis et al., Nanomedicine 2 (I) (2006) 8-21; Kumari et al., Colloids and Surfaces B: Biointerfaces 75 (2010) 1-18; and U.S. Patent Publication 20140066388). Polymeric nanoparticles may include or may be formed from biodegradable polymeric molecules, which in some embodiments may include dendrimers. Suitable dendrimers may include, but are not limited to, polyamidoamine (PAMAM) dendrimers. Polyamidoamine dendrimers have been used in the art as vehicles for intracellular delivery of therapeutics. (See Esfand et al., Drug Discov. Today (2001) 6(8):427-436; and Bharali, International Journal of Nanomedicine (2009) 4:1-7). Polyamidoamine dendrimers suitable for preparing the presently disclosed nanoparticles may include 3rd-, 4th-, 5th-, or preferably at least 6th-generation dendrimers.

Polymeric nanoparticles may also include or may be formed from other biodegradable polymeric molecules which may include, without limitation, polylactic acid (PLA), polygycolic acid (PGA), co-polymers of PLA and PGA (i.e., polyactic-co-glycolic acid (PLGA)), poly-ε-caprolactone (PCL), polyethylene glycol (PEG), poly(3-hydroxybutyrate), poly(p-dioxanone), polypropylene fumarate, poly(orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis (p-carboxypheonoxy)methane](PCPM), copolymers of PSA, PCPP and PCPM, poly (amino acids), poly(pseudo amino acids), polyphosphazenes, derivatives of poly[(dichloro)phosphazenes] and poly[(organo)phosphazenes], poly-hydroxybutyric acid, or S-caproic acid, elastin, gelatin, and chitosan. (See, e.g., Kumari et al., Colloids and Surfaces B: Biointerfaces 75 (2010) 1-18; and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425). In some embodiments, the nanoparticles may include a mixture of PLGA and PAMAM.

Polymeric nanoparticles may be prepared by methods known in the art. (See, e.g., Nagavarma et al., Asian J. of Pharma. And Clin. Res., Vol 5, Suppl 3, 2012, pages 16-23; Cismaru et al., Rev. Roum. Chim., 2010, 55(8), 433-442; and International Application Publication Nos. WO 2012/115806; and WO 2012/054425). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the disclosed methods may be subjected to further processing steps such as washing and lyophilization, as desired. Optionally, the nanoparticles may be combined with a preservative (e.g., trehalose).

Micelle and liposomal-based nanoparticles may also serve as suitable delivery particles. See, e.g., U.S. Pat. No. 8,252,324. Micelles are self-assembling spherical colloidal nanoparticles formed by amphiphilic molecules. Micelles are also described as aggregate surfactant molecules disbursed in a liquid colloid. The core of the micelle, which is segregated in an aqueous milieu, is capable of encapsulating polynucleotides and/or proteins protecting them from destruction and biological surroundings while improving their pharmacokinetics and biodistribution. Micelles are generally in the order of 5-50 nm in diameter, and are therefore capable of accumulating in pathological areas with leaky vasculature, such as infarct zones and tumors due to the enhanced permeability and retention effect. Micelles are also capable of evading a major obstacle in drug targeting by particulate systems: non-specific uptake by the reticuloendothelial systems and renal secretion.

Micelles may be formed by any of commonly known surfactants, such as sodium dodecylsulfate or phospholipids, but the performance of such surfactants as drug delivery systems is low compared to micelles composed of specially designed block copolymers, as described in Kataoka et al., supra and Torchilin et al., supra (2003). The flexible hydrophilic polymers, which are used as shell-forming segments for the polymer micelles, assemble into a dense palisade shell, which is cross-linked by numerous water molecules to achieve effective stabilization of the vesicle. Accordingly, the polymer micelles dissociate much more slowly than unmodified surfactant micelles, retain the loaded drugs for a longer period of time and accumulate the drug at the target site more efficiently. Further, polymer micelles are readily engineered to have sizes in the range of several tens of nanometers with a narrow size distribution which is a great advantage in regulating biodistribution.

In contrast to micelles, liposomes are bilayered phospholipid vesicles approximately 50 to 1,000 nm in diameter. Liposomes are biologically inert and completely biocompatible; they cause practically no toxic or antigenic reactions. Polynucleotides and/or proteins included in liposomes are protected from the destructive action of the external media by the liposomes. Thus, liposomes are able to deliver their content inside cells and even inside different cell compartments. Generally, liposomes are considered a promising carrier with significant therapeutic potential, as demonstrated in numerous laboratory tests and clinical trials, e.g., Torchilin, Nat. Rev. Drug discov. 4, 145-160 (2005).

It is known that liposomes and micelles can be stabilized by enhancing the outermost hydrophobic shell with water soluble polymers, such as polyethyleneglycol (PEG). The presence of hydrophilic polymers on the hydrophobic surface of these carrier particles attracts a water shell, resulting in reduced adsorption of opsonins to the carrier particles. This, in turn, results in a decrease in both the rate and extent of uptake of carrier particles by mononuclear phagocytes. Long circulating liposomes improved the therapeutic index of drugs and encapsulated therein. Currently, several preparations based on long circulating liposomes are commercially available, for example, Doxil®, a doxorubicin containing polyethyleneglycolated (PEGylated) liposomes, Sharp et al., Drugs 62 2089-2126 (2002). Doxil is manufactured by ortho biotech products, LP of bridgewater, N.J., USA. O'Shaughnessy, Clin. Breast cancer 4, 318-328, (2003), demonstrated selective delivery of doxorubicin into solid tumors in patients with breast carcinoma metastases was achieved by capsulation of the drug into PEGylated liposomes, which resulted in subsequent improvement of survival. Efficacy was also demonstrated by combining liposomal doxorubicin with paclitaxel (available as Taxol®, Bristol-Meyers Squibb Company, New York, N.Y., USA) caelyx (Schering-Plough corporation, Kenilworth, N.J., USA) and carboplatin (available as Paraplatin® from Bristol-Meyers Squibb company). Several preparations of liposomes have been approved for clinical application or undergoing clinical evaluation, Torchilin, supra, (2005).

Delivery particles may also include nanoparticles including lipids and polymer components. For example, nanoparticles including a phospholipid bilayer and poly(beta-amino ester) (PBAE) have been developed for the in vivo delivery of polynucleotides. See, e.g., Su et al., *Molecular Pharmaceutics,* 8(3):774-787 (2011).

The delivery particles may include a surfactant which may include a cationic surfactant. Suitable cationic surfactants may include but are not limited to quaternary ammonium compounds, for example, quaternary ammonium compounds or salts thereof having a formula $(X)_3N^+(CH_2)_n(CH_3)$ where X is $C_{1-6}$ alkyl or aryl, and n=(9, 11, 13, 15, or 17). Suitable salts of the quaternary ammonium compounds may include halide salts (e.g., $Cl^-$ or $Br^-$ salts) such as cetyltrimethylammonium bromide (CTAB).

The delivery particles preferably have physical properties that facilitate uptake by a targeted cell. For example, preferably the nanoparticles have a size and a charge that that facilitate uptake by a targeted cell. Typically, the nanoparticles have a mean effective diameter of less than 1 micron, and preferably the nanoparticles have a mean effective diameter of between about 25 nm and about 500 nm, and more preferably between about 50 nm and about 250 nm, and most preferably about 100 nm to about 150 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The disclosed delivery particles preferably have a zeta-potential that facilitates uptake by a target cell. Typically, the nanoparticles have a zeta-potential greater than 0. In some embodiments, the nanoparticles have a zeta-potential between about 5 mV to about 45 mV, between about 15 mV to about 35 mV, or between about 20 mV and about 30 mV. Zeta-potential may be experimental determined via characteristics that include electrophoretic mobility or dynamic electrophoretic mobility. Electrokinetic phenomena and electroacoustic phenomena may be utilized to calculate zeta-potential.

Delivery particles will be taken up by cells non-specifically even if the particles do not include a specific ligand on their surface. However, the disclosed delivery particles may be configured to also include a ligand that specifically targets a particular cell type. In order to achieve more specific targeting of delivery particles, such particles may be modified with various ligands using advance conjugation procedures. For example, antibodies and small peptides have been attached to the water exposed tips of polyethyleneglycol chains, Blume, et al. Biomembranes 1149, 180-184 (1993). Antibodies and small peptides have also been conjugated via reactive p-nitrophenylcarbonyl, N-benzotrazole carbonyl or maleimide terminated PEG-phosphatidylethanolamine, Moreira, Pharm. Res. 19, 265-269 (2002); Torchilin et al., supra (2001); Xiong, et al., J. Pharm. Sci. 94, 1782-1793 (2005).

Pharmaceutical compositions including any of the compositions described herein are also provided. The pharmaceutical compositions may include a pharmaceutical carrier, excipient, or diluent, which are nontoxic to the cell or subject being exposed thereto at the dosages and concentrations employed. Often a pharmaceutical diluent is in an aqueous pH buffered solution. Examples of pharmaceutical carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

The pharmaceutical compositions described herein may include adjuvants to increase immunogenicity of the composition. In some embodiments, these compositions comprise one or more of a mineral adjuvant, gel-based adjuvant, tensoactive agent, bacterial product, oil emulsion, particulated adjuvant, fusion protein, and lipopeptide. Mineral salt adjuvants include aluminum adjuvants, salts of calcium (e.g. calcium phosphate), iron and zirconium. Gel-based adjuvants include aluminum gel-based adjuvants and acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), cholera toxin or other bacterial toxins, and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein. Notably, several of the delivery particles noted above may also act as adjuvants.

In some embodiments, the pharmaceutical compositions further include cytokines (e.g. IFN-γ, granulocyte-macrophage colony stimulating factor (GM-CSF) IL-2, or IL-12) or immunostimulatory molecules such as FasL, CD40 ligand or a toll-like receptor agonist, or carbohydrate adjuvants (e.g. inulin-derived adjuvants, such as, gamma inulin, algammulin, and polysaccharides based on glucose and mannose, such as glucans, dextrans, lentinans, glucomannans and galactomannans). In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496 the contents of which are hereby incorporated by reference in their entireties.

In some embodiments, the adjuvant is an aluminum gel or salt, such as aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, pharmaceutical compositions include oil-in-water emulsion formulations, saponin adjuvants, ovalbumin, Freunds Adjuvant, cytokines, and/or chitosans. Illustrative compositions comprise one or more of the following.

(1) ovalbumin (e.g. ENDOFIT);

(2) oil-in-water emulsion formulations, with or without other specific immunostimulating agents, such as: (a) MF59 (PCT Publ. No. WO 90/14837), which may contain 5% Squalene, 0.5% Tween 80, and 0.5% Span 85 (optionally containing various amounts of MTP-PE) formulated into submicron particles, (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+CWS (DETOX™); and (d) ADDAVAX (Invitrogen);

(3) saponin adjuvants, such as STIMULON (Cambridge Bioscience, Worcester, Mass.);

(4) Complete Freunds Adjuvant (CFA) and Incomplete Freunds Adjuvant (IFA);

(5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc;

(6) chitosans and other derivatives of chitin or poly-N-acetyl-D-glucosamine in which the greater proportion of the N-acetyl groups have been removed through hydrolysis; and (7) other substances that act as immunostimulating agents to enhance the effectiveness of the composition, e.g., monophosphoryl lipid A.

In other embodiments, adjuvants include a flagellin-based agent, an aluminium salt or gel, a pattern recognition receptors (PRR) agonist, CpG ODNs and imidazoquinolines. In some embodiments, adjuvants include a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

Methods of treating a cancer or precancer in a subject are also provided. The methods may include administering to the subject a therapeutically effective amount of any one of the MAVS compositions described herein to the subject having the cancer or precancer. As used herein, the "subject" may be any mammal, suitably a human, or domesticated animal such as a dog, cat, horse, cow, pig, or a mouse or rat. Exemplary cancers in accordance with the present invention include, without limitation, primary and metastatic breast, ovarian, liver, pancreatic, prostate, bladder, lung, osteosarcoma, pancreatic, gastric, esophageal, colon, skin cancers (basal and squamous carcinoma; melanoma), testicular, colorectal, urothelial, renal cell, hepatocellular, leukemia, lymphoma, multiple myeloma, head and neck, and central nervous system cancers or pre-cancers.

Treating cancer includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

A "therapeutically effective amount" or an "effective amount" as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions and pharmaceutical compositions described herein may be administered by any means known to those skilled in the art, including, without limitation, intralesionally, intravenously, intra-tumorally, intradermally, topically, intraperitoneally, intramuscularly, parenterally, or subcutaneously. Thus the compositions may be formulated as an injectable, topical or ingestible, suppository formulation. Administration of the compositions and pharmaceutical compositions to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of a a MAVS composition and/or anti-cancer therapeutic agent administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of a a MAVS composition and/or anti-cancer therapeutic agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of a a MAVS composition and/or anti-cancer therapeutic agent for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer by, for example, by reducing tumor size or decreasing the rate of tumor growth by least 10%, 20%, 30%, 40%, 50%, 60%, 70%, 80%, 90%, 100% or more as compared to no treatment.

The effective dosage amounts of a a MAVS composition and/or anti-cancer therapeutic agent herein refer to total amounts administered, that is, if more than one composition is administered, the effective dosage amounts of a a MAVS composition and/or anti-cancer therapeutic agent corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The compositions and pharmaceutical compositions described herein may be administered one time or more than one time to the subject to effectively treat cancer. Suitable dosage ranges for a a MAVS composition and/or anti-cancer therapeutic agent may be of the order of several hundred micrograms of the inhibitor and/or agent with a range from about 0.001 to 10 mg/kg/day, preferably in the range from about 0.01 to 1 mg/kg/day. Precise amounts of a MAVS composition and/or anti-cancer therapeutic agent required to be administered depend on the judgment of the practitioner and may be peculiar to each subject. It will be apparent to those of skill in the art that the therapeutically effective amount of the compositions and pharmaceutical compositions described herein will depend, inter alia, upon the administration schedule, the unit dose of agent administered, whether the composition is administered in combination with other therapeutic agents, the status and health of the recipient, and the therapeutic activity of the particular composition.

The effectiveness of an anti-cancer therapeutic agent may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% when combined with a a MAVS composition and relative to a control treated with the anti-cancer therapeutic agent alone. Suitably, the MAVS compositions and methods described herein may reduce the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as saline or relative to administration of the anti-cancer therapeutic agent alone.

The methods of the present invention also include methods of treating cancer in a subject including administering to the subject a therapeutically effective amount of any of the MAVS compositions described herein and administering to the subject a therapeutically effective amount of an anti-cancer therapeutic agent to the subject. The MAVS composition may be administered before, after, or concurrently with the anti-cancer therapeutic agent. In some embodiments, the MAVS composition is administered at least 6 hours, 12 hours, 18 hours, 1 day, 2 days, 3 days, 4 days, 5 days, or more prior to the anti-cancer therapeutic agent. In some embodiments, the anti-cancer therapeutic agent is administered at least 6 hours, 12 hours, 18 hours, 1 day, 2 days, 3 days, 4 days, 5 days, or more prior to the MAVS composition.

Kits are also provided. The kits may include any of the MAVS compositions described herein and an anti-cancer therapeutic agent. The kits may further include the components required to perform any of the methods disclosed herein.

Cells engineered to have reduced or no expression of at least one innate immune signaling gene are also provided. The innate immune signaling gene may be any gene involved in an innate immune signaling pathway within a cell. In some embodiments, the innate immune signaling gene may be MyD88, TRIF, MAVS, IRAK4, or TRAF6. The cells may be any type of cell suitable for production of a virus such as mammlian cells including, without limitation, CHO cells, HEK293 cells, HEK293T cells, HeLa cells, NS0 cells, Sp2/0 cells, COS cells, BK cells, MDCK cells, or Vero cells.

The cells may be engineered to have reduced or no expression of at least one innate immune signaling gene using recombinant and/or genome engineering techniques well known in the art. In some embodiments, the cell includes an shRNA, microRNA, an antisense construct, or RNAi construct targeting the innate immune signaling gene. A person of ordinary skill in the art would also appreciate that the expression of the innate immune signaling gene could be reduced or eliminated by introducing modification to the gene itself using genome engineering techniques such as CRISPR/Cas methods.

Methods of producing a virus in a cell are also provided. The methods may include introducing a virus into any one of the engineered cells described herein. Optionally, the methods may further include purifying the virus from the cell. The virus may be replication defective retroviruses, herpes simplex virus, lentiviruses, adenoviruses or adeno-associated viruses.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Intralesional Vaccination with Ad-MAVS Alters the Immunosuppressive Tumor Microenvironment and Elicits Robust Anti-Tumor Immunity in Non-Immunogenic Cancers Methods:
MAVS Production To generate an adenoviral vector expressing MAVS, we subcloned MAVS directly into a pshuttle CMV vector either directly or using a PCR amplification strategy. Upon successful subcloning, we then used standard recombination procedures (with the PadEasy-1 system) to generate [E1-E3-] Ad vectors using standard procedures and protocols (1). In cases where we needed to insert a second gene into Ad vectors, an E3 shuttle was constructed (details available upon request) and recombined with genomic backbone plasmids in BJ5183 cells. To grow adenoviral vectors, PacI digested (linearized) plasmids were transiently transfected into 293T cells. In previous experiments, we found that innate immune responses inhibited early Ad growth, thus we generated a series of specialized 293T cells with inhibited innate immune responses (using shRNA KD of innate immune genes or overexpression of immune-suppressive pp65) that enhanced early vector growth to allow for more rapid production of adenovirus (see Table 1 below for experiments with MyD88 adaptor viruses). For the studies reported in the Figures, we utilized 293T-IRAK4KD-pp65 overexpressing cell lines to generate the initial viral titer that was subsequently expanded and purified in 293 cells. In these studies the shRNA targeting TRAF6 (for example, AAACTCATCCCTGAATATC (SEQ ID NO: 7) mature antisense sequence) or its Untranslated region (UTR) and/or IRAK4 (for example, ATTACCACCAACAGAAATG (SEQ ID NO: 8) mature antisense sequence) or its Untranslated region (UTR).

TABLE 1

Viral Growth Table

| Stable Cell Lines | Ad-MyD88(Mm) | Ad-MyD88(Hs) | Ad-MyD88(Mm)-LacZ | Ad-MyD88(Mm)-CEA |
|---|---|---|---|---|
| 293T Derivative cell lines | − | − | − | − |
| Untreated | − | − | − | − |
| MyD88KD | − | − | − | − |
| TRIF KD | − | − | − | − |
| MAVS KD | − | − | − | − |
| IRAK4 KD | − | − | − | − |
| TRAF6KD | − | − | − | − |
| IRAK4-TRAF6-KD | + | ++ | + | − |
| TRAF6-IRAK4 KD | + | ++ | + | + |
| IRAK4KD-pp65 Overexpression | + | ++ | + | − |
| TRAF6KD-pp65 Overexpression | ++ | ++ | ++ | − |

++ = More than 3 wells showing Cytopathic Effect (CPE)
+ = 1-2 wells showing CPE
− = No CPE or evidence of viral growth Additionally, the enhanced growth allowed for less time to permit recombination of Ad E1 genes with the vector backbone. All Ad vector stocks were evaluated for replication-competent adenovirus (RCA) via a polymerase chain reaction (PCR)-based RCA assay, as described by Lochmuller et al. (2). Once adenoviral vectors were scaled up, elevated MOIs permitted robust growth without the use of specialized cell lines. Ad preps were also tested for LPS contamination using an E-Toxate kit (Sigma, St. Louis, Mo.) per the manufacturers' recommendations with all preps containing <1 EU per ml.

Evaluation of Ad-MAVS Overexpression

In order to determine the possible effect MAVS would have on different cell types within the tumor microenvironment we infected a range of primary and cancer cells types (Bone-marrow derived dendritic cells (BMDCs), primary fibroblasts, as well as 5 different murine tumor cell lines representing breast-4T1, colon-CT26CL25, bladder-MB49, melanoma-B16F10, and prostate-TRAMPC2) with Ad-MAVS or a control Ad. Innate immune responses were measured via luminex ELISA, microarray, and RT-qPCR. The impact on tumor growth was assessed by MTT and expression of PD-L1 by FACS. Lastly, we measured the anti-tumor effect and adaptive immune responses of animals treated with various combinations of Ad-MAVS, a control Ad, and PD-L1 targeting antibodies in vivo utilizing various immunocompetent and immune-compromised mouse models.

Generation of Doxycycline-Inducible MAVS in Mouse Cell Lines (MC38 and CT26.CL25)

Dox-inducible MAVS cells lines were generated using a version of Dox-inducible lentiviral vectors that consitutatively express EGFP from a EF1a promoter (similar to those described in Hartman et al., Can Res., 2013) that was engineered using a cDNA for the murine form of MAVS. High titers of these viruses were generated by transient transduction of 293T cells and concentration by ultracentrifugation using standard methods. After infection, cells were selected by FACS for GFP to establish stable lines that could be induced to express MAVS.

Results:

In vitro infection of BMDCs, MEFs, and murine tumor cell lines demonstrated that MAVS expression elicited widespread production of cytokines and chemokines indicative of a type I immune response (such as IL-12, TNF-alpha, RANTES, etc.) and interferon beta. See, e.g., FIGS. 1A-1G, FIGS. 2A-2E, and FIGS. 10A-10I. These profound responses also triggered immune regulatory feedback expression of PD-L1, enabling their targeting by PD-L1 antibodies. See, e.g., FIGS. 5A-5F, FIGS. 6A-6M, FIGS. 9A-9F, and FIGS. 10A-10I. Additionally, we found that Ad-MAVS infection of tumor cell lines significantly inhibited their proliferation in vitro, likely via interferon pathways. See, e.g., FIGS. 3A-3D. In vivo, treatment with Ad-MAVS also elicited robust stimulation of innate immune responses and numerous type I inflammatory cytokines. See, e.g., FIGS. 4A-4F, FIGS. 6A-6M, and FIGS. 10A-10I. Moreover, in multiple types of tumor bearing animals, we found that a single intralesional treatment of Ad-MAVS significantly prolonged overall survival and was capable of eliciting systemic anti-tumor adaptive immunity to non-immunogenic tumors. See, e.g., FIGS. 7A-7L.

Tables 2A-2D also shows the gene expression alterations in response to Ad-MAVS infection in fibroblasts indicative of a innate immune responses, particularly those mediated by interferon induction.

TABLE 2A

| Index | Name | P-value | Z-score | Combined Score* |
|---|---|---|---|---|
| 1 | response to other organism (GO: 0051707) | 0.000001351 | −2.41 | 15.24 |
| 2 | regulation of innate immune response (GO: 0045088) | 0.000001418 | −2.39 | 15.08 |
| 3 | positive regulation of interferon-beta production (GO: 0032728) | 0.00005676 | −2.56 | 11.09 |
| 4 | response to virus (GO: 0009615) | 0.00002306 | −2.37 | 10.48 |
| 5 | positive regulation of defense response (GO: 0031349) | 0.00005542 | −2.42 | 10.46 |
| 6 | positive regulation of innate immune response (GO: 0045089) | 0.00002969 | −2.34 | 10.33 |

TABLE 2A-continued

| Index | Name | P-value | Z-score | Combined Score* |
|---|---|---|---|---|
| 7 | negative regulation of viral genome replication (GO: 0045071) | 0.00004274 | −2.33 | 10.29 |
| 8 | regulation of type I interferon production (GO: 0032479) | 0.00004099 | −2.27 | 10.01 |
| 9 | regulation of symbiosis, encompassing mutualism through parasitism (GO: 0043903) | 0.00006343 | −2.31 | 10.00 |
| 10 | positive regulation of type I interferon production (GO: 0032481) | 0.00002587 | −2.24 | 9.90 |

TABLE 2B

| Index | Name | P-value | Z-score | Combined Score* |
|---|---|---|---|---|
| 1 | cytokine cytokine receptor interaction | 0.001513 | −2.08 | 5.03 |
| 2 | jak stat signaling pathway | 0.002282 | −1.90 | 4.59 |
| 3 | toll like receptor signaling pathway | 0.02041 | −1.78 | 1.13 |
| 4 | prostate cancer* | 0.04759 | −1.87 | 0.79 |
| 5 | acute myeloid leukemia* | 0.05084 | −1.70 | 0.72 |
| 6 | natural killer cell mediated cytotoxicity | 0.05249 | −1.69 | 0.72 |
| 7 | mapk signaling pathway | 0.09162 | −1.66 | 0.71 |
| 8 | b cell receptor signaling pathway* | 0.07615 | −1.45 | 0.62 |
| 9 | fc epsilon ri signaling pathway* | 0.1124 | −1.31 | 0.56 |
| 10 | adipocytokine signaling pathway* | 0.1028 | −1.29 | 0.55 |

TABLE 2C

| Index | Name | P-value | Z-score | Combined Score* |
|---|---|---|---|---|
| 1 | small molecule biosynthetic process (GO: 0044283) | 0.0001333 | −2.38 | 4.46 |
| 2 | pyrimidine ribonucleoside triphosphate metabolic process (GO: 0009208)* | 0.007418 | −2.83 | 2.13 |
| 3 | pyrimidine nucleoside triphosphate biosynthetic process (GO: 0009148)* | 0.008795 | −2.82 | 2.12 |
| 4 | pyrimidine ribonucleoside triphosphate biosynthetic process (GO: 0009209)* | 0.006769 | −2.81 | 2.12 |
| 5 | UTP metabolic process (GO: 0046051)* | 0.004452 | −2.79 | 2.10 |
| 6 | UTP biosynthetic process (GO: 0006228)* | 0.003943 | −2.78 | 2.10 |
| 7 | regulation of fatty acid oxidation (GO: 0046320)* | 0.01028 | −2.78 | 2.10 |
| 8 | positive regulation of cGMP metabolic process (GO: 0030825)* | 0.007418 | −2.75 | 2.07 |
| 9 | isoprenoid biosynthetic process (GO: 0008299)* | 0.009523 | −2.73 | 2.06 |
| 10 | Rac protein signal transduction (GO: 0016601)* | 0.005555 | −2.73 | 2.06 |

TABLE 2D

| Index | Name | P-value | Z-score | Combined Score* |
|---|---|---|---|---|
| 1 | biosynthesis of steroids* | 0.0009785 | −1.80 | 6.18 |
| 2 | aminosugars metabolism* | 0.02547 | −1.79 | 2.38 |
| 3 | basal transcription factors* | 0.03195 | −1.69 | 2.24 |
| 4 | pyrimidine metabolism* | 0.03217 | −1.64 | 2.18 |
| 5 | n glycan biosynthesis* | 0.04660 | −1.54 | 1.84 |
| 6 | hedgehog signaling pathway* | 0.08157 | −1.45 | 1.39 |
| 7 | cell cycle* | 0.2111 | −1.33 | 0.83 |
| 8 | purine metabolism* | 0.3170 | −0.85 | 0.53 |
| 9 | glycosylphosphatidylinositol anchor biosynthesis* | 0.1776 | −0.69 | 0.43 |
| 10 | dna polymerase* | 0.1843 | −0.63 | 0.39 |

Activation of MAVS Induces Innate Immunity in Colorectal Cancer Cells

We investigated the expression of innate immune genes after doxycycline-mediated MAVS induction in MC38 and CT26.CL25 colorectal carcinoma cells through quantitative real-time PCR for multiple interferon induced gene targets. These studies demonstrate that MAVS expression can elicit widespread canonical Interferon beta signaling in different cell lines through different methods (either by inducible expression in stable cell lines or through overexpression by adenoviral vector transduction). See, e.g., FIGS. 11A-11D.

MAVS Induction in Tumor Microenvironment Suppresses Tumor Growth

To investigate how induction of MAVS would affect tumor growth, we engrafted 10^6 MC38-MAVS cells or 10^5 CT26.CL25-MAVS cells subcutaneously in the flank of a mouse line. One week post engraftment, mice were given normal or doxycycline-containing chow for MAVS induction in the tumor microenvironment. See, e.g., FIGS. 12A-12D. These studies demonstrate that induction of MAVS expression can have a robust anti-tumor effect on tumor cell growth in immunocompetent mice.

Figure 13A:
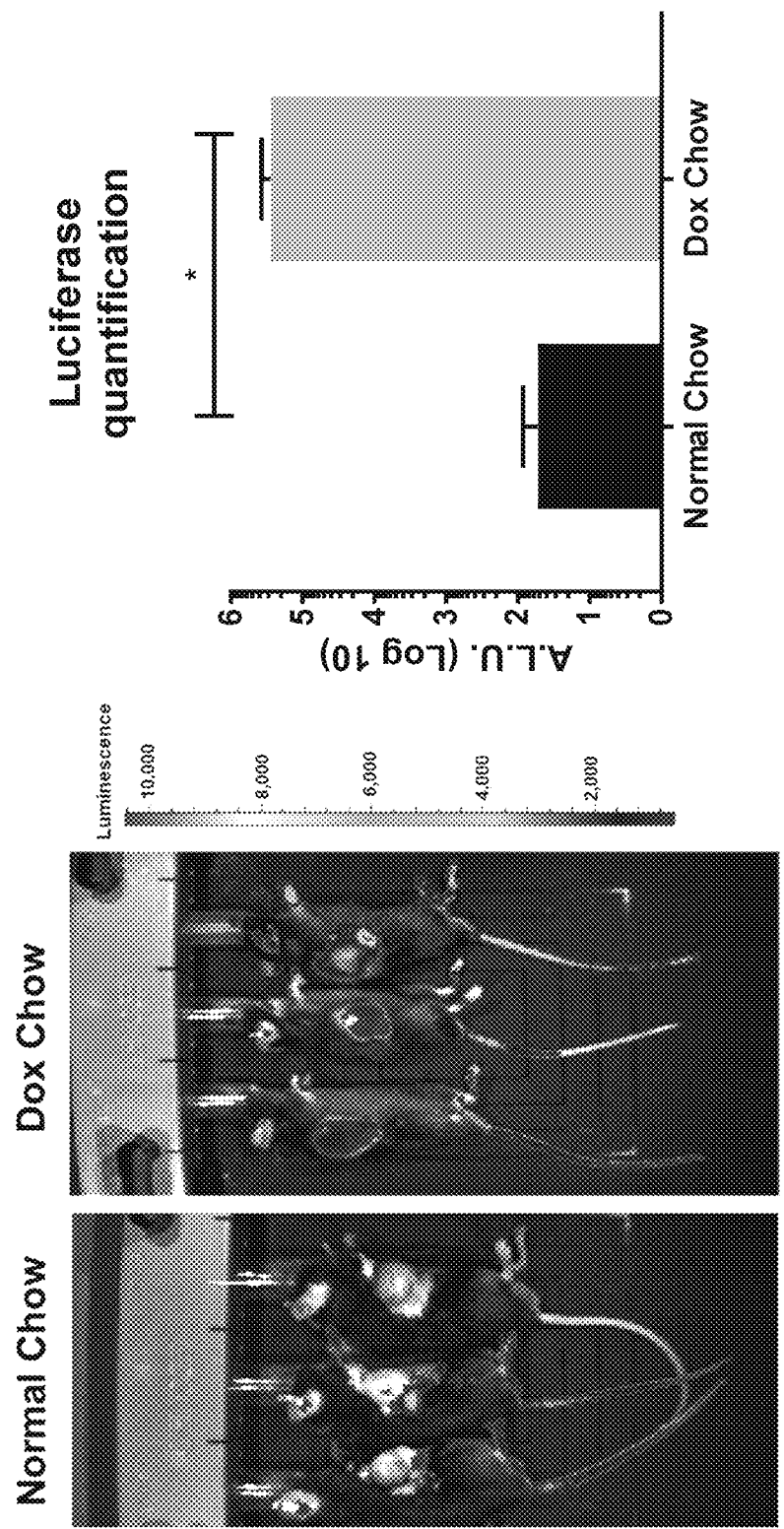

MAVS Induction in the Tumor Microenvironment Promotes Immune Cell Infiltration and Anti-Tumor Specific Immune Responses To determine the affect of MAVS induction on an anti-tumor response and tumor immune cell infiltration, MC38 cells with dox-inducible MAVS were engrafted into a transgenic T-LUX mice, in which T-cells express luciferase expressed from a CD2 promoter (Chewning et al., BMC Immuno., 2009) See, e.g., FIGS. 13A-13C. These results demonstrate that MAVS expression can elicit enhanced T-cell, as well as NK cell, infiltration into tumors.

MAVS Activation Induces Expression of the Immune Checkpoint Protein PD-L1 in Tumor Microenvironment.

Figure 14A:
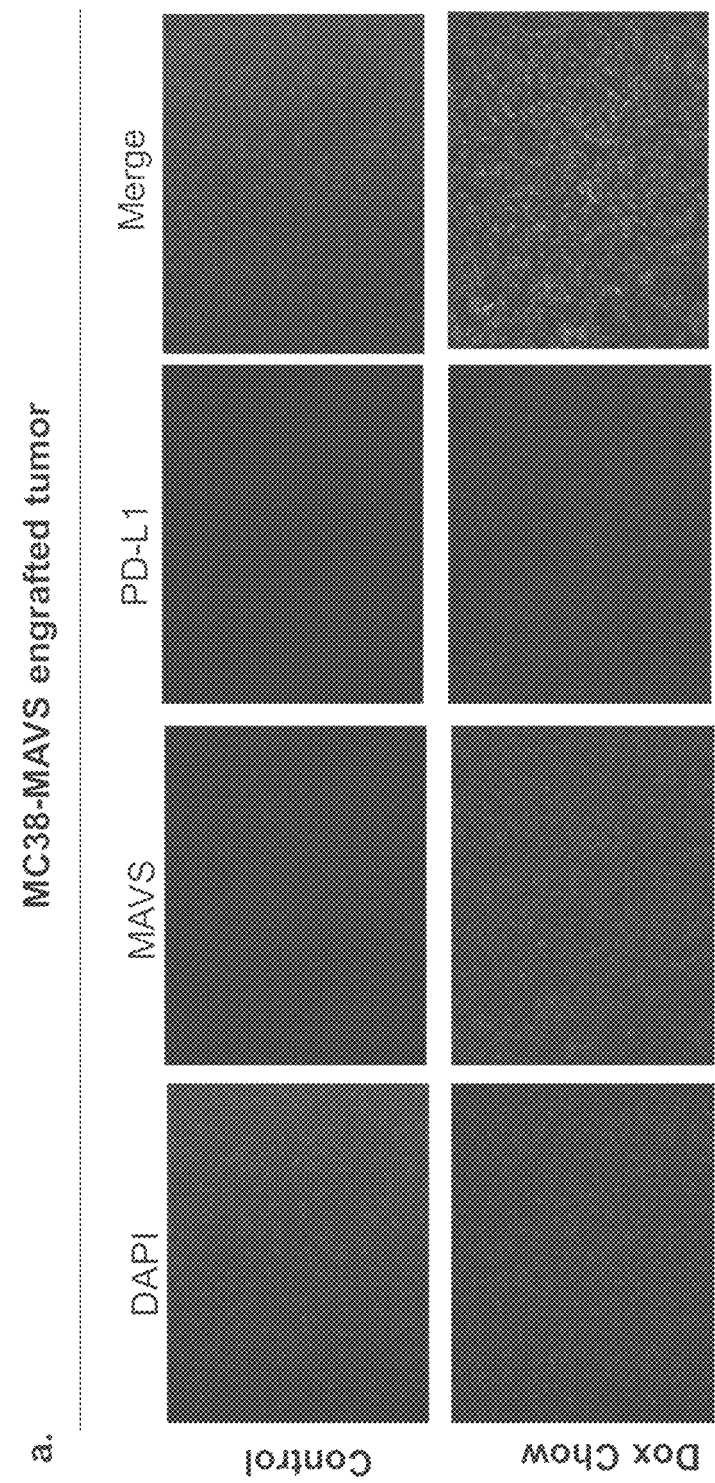
FIGS. 14A-14B show MAVS activation induces expression of the immune checkpoint protein PD-L1 in tumor microenvironment.
Figure 14B:
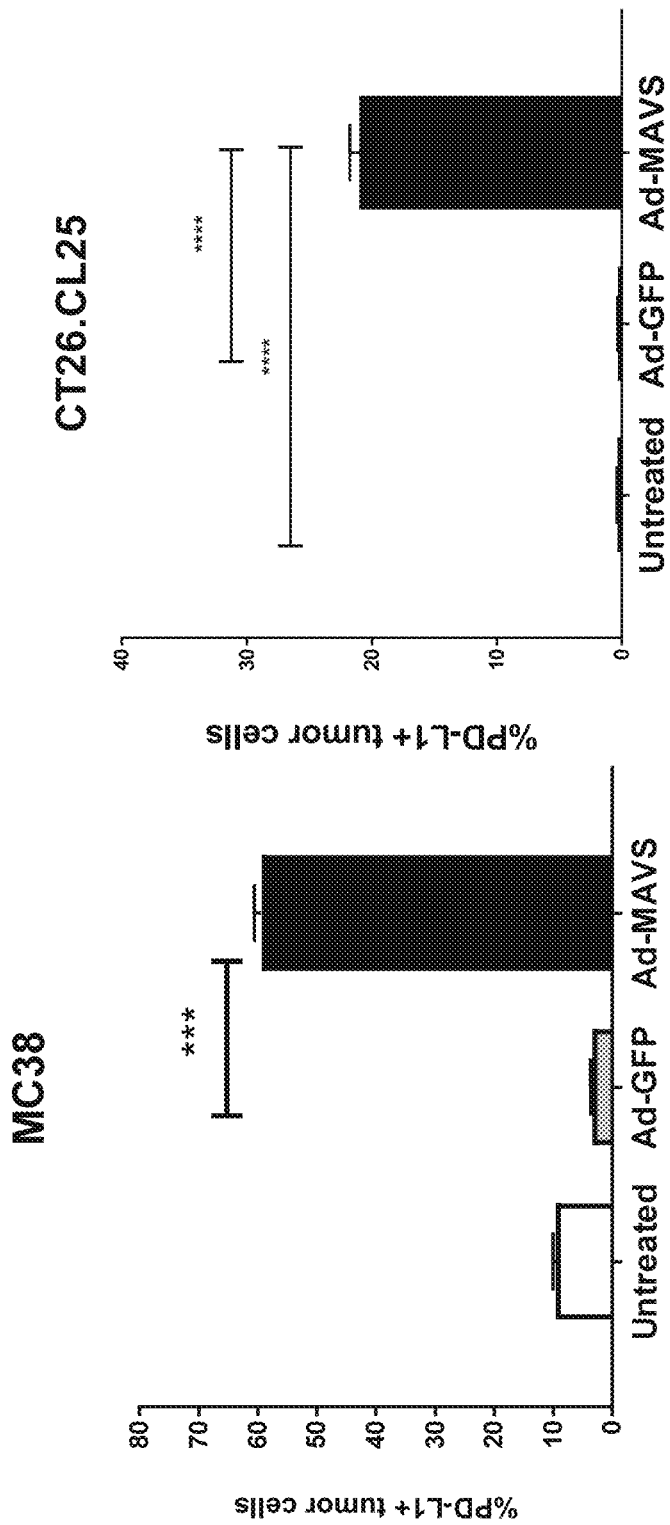

To determine the affect of MAVS induction on immune checkpoint expression, MC38-MAVS engrafted tumors (4 weeks) as described above were analyzed by immunofluorescence staining for MAVS (Green) and PDL1 (Red). See, e.g., FIGS. 14A-14B. These results demonstrate that MAVS expression also induces the expression of PDL1 on T-cells that infiltrate into the tumor microenvironment (TME), which may make these tumors more attractive candidates for PDL1 or PD1 antibody therapies.

Our study identifies that MAVS expression can elicit the production of a significant number of Th1-type cytokines, chemokines, and interferon-beta in multiple cell types within the tumor microenvironment. We also demonstrate that overexpression of MAVS results in the direct suppression of tumor cell growth and stimulation of tumor PD-L1 expression. These activities were also observed in vivo, as intralesional injection of Ad-MAVS elicited Th1 cytokines and anti-tumor immunity in multiple tumor types, which correlated with enhanced systemic T-cell responses to tumor-specific epitopes, as well as enhanced T-cell infiltration into tumors as well as elevated PDL1 expression in tumor lesions. Collectively, these data demonstrate that intralesion injection of Ad-MAVS alters the tumor microenvironment to stimulate anti-tumor immunity and potentially sensitizes non-immunogenic tumors to PD-L1 (or PD-1) therapies. As such, Ad-MAVS represents a novel approach of stimulating anti-tumor immunity via activation of innate adaptor molecules to improve immunogenic anti-tumor responses and potentially the therapeutic efficacy of PD-L1 or PD-1 immune checkpoint blockade.

REFERENCES

1. He T C, Zhou S, da Costa L T, Yu J, Kinzler K W, and Vogelstein B. A simplified system for generating recombinant adenoviruses. *ProcNatlAcadSciUSA*. 1998; 95(5): 2509-14.
2. Lochmuller H, Jani A, Huard J, Prescott S, Simoneau M, Massie B, Karpati G, and Acsadi G. Emergence of early region 1-containing replication-competent adenovirus in stocks of replication-defective adenovirus recombinants (delta E1+delta E3) during multiple passages in 293 cells. *HumGene Ther*. 1994; 5(12):1485-91.

We claim:

1. A method of treating a cancer or precancer in a subject comprising administering to the subject a therapeutically effective amount of a gene therapy vector comprising a polynucleotide comprising a first heterologous promoter operably connected to a first polynucleotide encoding a Mitochondrial Antiviral Signaling (MAVS) polypeptide to the subject having the cancer or precancer, wherein the MAVS polypeptide has at least 95% sequence identity to SEQ ID NO: 1 or SEQ ID NO: 2.

2. The method of claim 1, wherein the composition is administered intralesionally.

3. The method of claim 1, further comprising administering a therapeutically effective amount of an anti-cancer therapeutic agent to the subject.

4. The method of claim 3, wherein the composition is administered concurrently with or prior to administration of the anti-cancer therapeutic agent.

5. The method of claim 3, wherein the anti-cancer therapeutic agent is selected from the group consisting of an anti-cancer biologic, a checkpoint inhibitor, a cancer vaccine, a T cell, an oncolytic virus, and a bispecific antibody.

6. The method of claim 3, wherein the anti-cancer therapeutic agent is selected from the group consisting of an Antigen-4 (CTLA-4) inhibitor, a programmed death-I/programmed death-ligands (PD-1/PD-L) inhibitor, and a T cell immunoglobulin mucin-3 (TIM-3) inhibitor.

7. The method of claim 3, wherein the anti-cancer therapeutic agent is selected from the group consisting of an anti-CTLA-4 antibody, an anti-PD-1 antibody, and an anti-PD-L1 antibody.

8. The method of claim 1, wherein the subject is human.

9. The method of claim 1, wherein the gene therapy vector further comprises a second polynucleotide encoding a cancer antigen operably connected to the first promoter or a second promoter.

10. The method of claim 9, wherein the cancer antigen is selected from the group consisting of an ESR1 polypeptide, mutant or portion thereof; a HER3 polypeptide, mutant or portion thereof; a mutant HER2 polypeptide or portions thereof, and combinations thereof.

11. The method of claim 9, wherein the second polynucleotide is fused in frame to a third polynucleotide encoding a lactadherin polypeptide or portions thereof.

12. The gene therapy vector of claim 11, wherein the lactadherin polypeptide comprises any one of SEQ ID NOS: 3-6 or a homolog thereof.

13. The method of claim 1, wherein the gene therapy vector is selected from the group consisting of an adenoviral vector, a fowlpox vector, a vaccinia vector, a VEE vector, and a mini-circle DNA (mcDNA) vector.

* * * * *

SEQUENCE LISTING

<160> NUMBER OF SEQ ID NOS: 8

<210> SEQ ID NO 1
<211> LENGTH: 540
<212> TYPE: PRT
<213> ORGANISM: Homo sapiens
<220> FEATURE:
<221> NAME/KEY: misc_feature
<222> LOCATION: (1)..(540)
<223> OTHER INFORMATION: Human MAVS protein (Mitochondrial antiviral-
      signaling protein)

<400> SEQUENCE: 1

Met Pro Phe Ala Glu Asp Lys Thr Tyr Lys Tyr Ile Cys Arg Asn Phe
1               5                   10                  15

Ser Asn Phe Cys Asn Val Asp Val Val Glu Ile Leu Pro Tyr Leu Pro
            20                  25                  30

Cys Leu Thr Ala Arg Asp Gln Asp Arg Leu Arg Ala Thr Cys Thr Leu
        35                  40                  45

Ser Gly Asn Arg Asp Thr Leu Trp His Leu Phe Asn Thr Leu Gln Arg
    50                  55                  60

Arg Pro Gly Trp Val Glu Tyr Phe Ile Ala Ala Leu Arg Gly Cys Glu
65                  70                  75                  80

Leu Val Asp Leu Ala Asp Glu Val Ala Ser Val Tyr Gln Ser Tyr Gln
                85                  90                  95

Pro Arg Thr Ser Asp Arg Pro Pro Asp Pro Leu Glu Pro Pro Ser Leu
            100                 105                 110

Pro Ala Glu Arg Pro Gly Pro Pro Thr Pro Ala Ala Ala His Ser Ile
        115                 120                 125

Pro Tyr Asn Ser Cys Arg Glu Lys Glu Pro Ser Tyr Pro Met Pro Val
    130                 135                 140

Gln Glu Thr Gln Ala Pro Glu Ser Pro Gly Glu Asn Ser Glu Gln Ala
145                 150                 155                 160

Leu Gln Thr Leu Ser Pro Arg Ala Ile Pro Arg Asn Pro Asp Gly Gly
                165                 170                 175

Pro Leu Glu Ser Ser Ser Asp Leu Ala Ala Leu Ser Pro Leu Thr Ser
            180                 185                 190

Ser Gly His Gln Glu Gln Asp Thr Glu Leu Gly Ser Thr His Thr Ala
        195                 200                 205

Gly Ala Thr Ser Ser Leu Thr Pro Ser Arg Gly Pro Val Ser Pro Ser
    210                 215                 220

-continued

Val Ser Phe Gln Pro Leu Ala Arg Ser Thr Pro Arg Ala Ser Arg Leu
225                 230                 235                 240

Pro Gly Pro Thr Gly Ser Val Val Ser Thr Gly Thr Ser Phe Ser Ser
            245                 250                 255

Ser Ser Pro Gly Leu Ala Ser Ala Gly Ala Glu Gly Lys Gln Gly
        260                 265                 270

Ala Glu Ser Asp Gln Ala Glu Pro Ile Ile Cys Ser Ser Gly Ala Glu
            275                 280                 285

Ala Pro Ala Asn Ser Leu Pro Ser Lys Val Pro Thr Thr Leu Met Pro
        290                 295                 300

Val Asn Thr Val Ala Leu Lys Val Pro Ala Asn Pro Ala Ser Val Ser
305                 310                 315                 320

Thr Val Pro Ser Lys Leu Pro Thr Ser Ser Lys Pro Pro Gly Ala Val
                325                 330                 335

Pro Ser Asn Ala Leu Thr Asn Pro Ala Pro Ser Lys Leu Pro Ile Asn
            340                 345                 350

Ser Thr Arg Ala Gly Met Val Pro Ser Lys Val Pro Thr Ser Met Val
        355                 360                 365

Leu Thr Lys Val Ser Ala Ser Thr Val Pro Thr Asp Gly Ser Ser Arg
    370                 375                 380

Asn Glu Glu Thr Pro Ala Ala Pro Thr Pro Ala Gly Ala Thr Gly Gly
385                 390                 395                 400

Ser Ser Ala Trp Leu Asp Ser Ser Ser Glu Asn Arg Gly Leu Gly Ser
                405                 410                 415

Glu Leu Ser Lys Pro Gly Val Leu Ala Ser Gln Val Asp Ser Pro Phe
            420                 425                 430

Ser Gly Cys Phe Glu Asp Leu Ala Ile Ser Ala Ser Thr Ser Leu Gly
        435                 440                 445

Met Gly Pro Cys His Gly Pro Glu Glu Asn Glu Tyr Lys Ser Glu Gly
    450                 455                 460

Thr Phe Gly Ile His Val Ala Glu Asn Pro Ser Ile Gln Leu Leu Glu
465                 470                 475                 480

Gly Asn Pro Gly Pro Pro Ala Asp Pro Asp Gly Gly Pro Arg Pro Gln
                485                 490                 495

Ala Asp Arg Lys Phe Gln Glu Arg Glu Val Pro Cys His Arg Pro Ser
            500                 505                 510

Pro Gly Ala Leu Trp Leu Gln Val Ala Val Thr Gly Val Leu Val Val
        515                 520                 525

Thr Leu Leu Val Val Leu Tyr Arg Arg Arg Leu His
    530                 535                 540

<210> SEQ ID NO 2
<211> LENGTH: 503
<212> TYPE: PRT
<213> ORGANISM: Mus musculus
<220> FEATURE:
<221> NAME/KEY: misc_feature
<222> LOCATION: (1)..(503)
<223> OTHER INFORMATION: Mitochondrial antiviral-signaling protein

<400> SEQUENCE: 2

Met Thr Phe Ala Glu Asp Lys Thr Tyr Lys Tyr Ile Arg Asp Asn His
1               5                   10                  15

Ser Lys Phe Cys Cys Val Asp Val Leu Glu Ile Leu Pro Tyr Leu Ser
            20                  25                  30

```
Cys Leu Thr Ala Ser Asp Gln Asp Arg Leu Arg Ala Ser Tyr Arg Gln
            35                  40                  45

Ile Gly Asn Arg Asp Thr Leu Trp Gly Leu Phe Asn Asn Leu Gln Arg
 50                  55                  60

Arg Pro Gly Trp Val Glu Val Phe Ile Arg Ala Leu Gln Ile Cys Glu
 65                  70                  75                  80

Leu Pro Gly Leu Ala Asp Gln Val Thr Arg Val Tyr Gln Ser Tyr Leu
                 85                  90                  95

Pro Pro Gly Thr Ser Leu Arg Ser Leu Glu Pro Leu Gln Leu Pro Asp
            100                 105                 110

Phe Pro Ala Ala Val Ser Gly Pro Ser Ala Phe Ala Pro Gly His Asn
            115                 120                 125

Ile Pro Asp His Gly Leu Arg Glu Thr Pro Ser Cys Pro Lys Pro Val
130                 135                 140

Gln Asp Thr Gln Pro Glu Ser Pro Val Glu Asn Ser Glu Gln Leu
145                 150                 155                 160

Leu Gln Thr Asn Ser Gly Ala Val Ala Arg Met Ser Gly Gly Ser Leu
                165                 170                 175

Ile Pro Ser Pro Asn Gln Gln Ala Leu Ser Pro Gln Pro Ser Arg Glu
            180                 185                 190

His Gln Glu Gln Glu Pro Glu Leu Gly Gly Ala His Ala Ala Asn Val
            195                 200                 205

Ala Ser Val Pro Ile Ala Thr Tyr Gly Pro Val Ser Pro Thr Val Ser
            210                 215                 220

Phe Gln Pro Leu Pro Arg Thr Ala Leu Arg Thr Asn Leu Leu Ser Gly
225                 230                 235                 240

Val Thr Val Ser Ala Leu Ser Ala Asp Thr Ser Leu Ser Ser Ser Ser
                245                 250                 255

Thr Gly Ser Ala Phe Ala Lys Gly Ala Gly Asp Gln Ala Lys Ala Ala
            260                 265                 270

Thr Cys Phe Ser Thr Thr Leu Thr Asn Ser Val Thr Thr Ser Ser Val
            275                 280                 285

Pro Ser Pro Arg Leu Val Pro Val Lys Thr Met Ser Ser Lys Leu Pro
290                 295                 300

Leu Ser Ser Lys Ser Thr Ala Ala Met Thr Ser Thr Val Leu Thr Asn
305                 310                 315                 320

Thr Ala Pro Ser Lys Leu Pro Ser Asn Ser Val Tyr Ala Gly Thr Val
                325                 330                 335

Pro Ser Arg Val Pro Ala Ser Val Ala Lys Ala Pro Ala Asn Thr Ile
            340                 345                 350

Pro Pro Glu Arg Asn Ser Lys Gln Ala Lys Glu Thr Pro Glu Gly Pro
            355                 360                 365

Ala Thr Lys Val Thr Thr Gly Gly Asn Gln Thr Gly Pro Asn Ser Ser
            370                 375                 380

Ile Arg Ser Leu His Ser Gly Pro Glu Met Ser Lys Pro Gly Val Leu
385                 390                 395                 400

Val Ser Gln Leu Asp Glu Pro Phe Ser Ala Cys Ser Val Asp Leu Ala
                405                 410                 415

Ile Ser Pro Ser Ser Leu Val Ser Glu Pro Asn His Gly Pro Glu
            420                 425                 430

Glu Asn Glu Tyr Ser Ser Phe Arg Ile Gln Val Asp Glu Ser Pro Ser
            435                 440                 445

Ala Asp Leu Leu Gly Ser Pro Glu Pro Leu Ala Thr Gln Gln Pro Gln
```

```
                450                 455                 460
Glu Glu Glu Glu His Cys Ala Ser Ser Met Pro Trp Ala Lys Trp Leu
465                 470                 475                 480

Gly Ala Thr Ser Ala Leu Leu Ala Val Phe Leu Ala Val Met Leu Tyr
                485                 490                 495

Arg Ser Arg Arg Leu Ala Gln
            500

<210> SEQ ID NO 3
<211> LENGTH: 351
<212> TYPE: PRT
<213> ORGANISM: Mus musculus
<220> FEATURE:
<221> NAME/KEY: misc_feature
<222> LOCATION: (1)..(351)
<223> OTHER INFORMATION: C1C2 domains of mouse lactadherin

<400> SEQUENCE: 3

Thr Glu Tyr Ile Cys Gln Cys Pro Val Gly Tyr Ser Gly Ile His Cys
1               5                   10                  15

Glu Thr Gly Cys Ser Thr Gln Leu Gly Met Glu Gly Gly Ala Ile Ala
            20                  25                  30

Asp Ser Gln Ile Ser Ala Ser Ser Val Tyr Met Gly Phe Met Gly Leu
        35                  40                  45

Gln Arg Trp Gly Pro Glu Leu Ala Arg Leu Tyr Arg Thr Gly Ile Val
    50                  55                  60

Asn Ala Trp Thr Ala Ser Asn Tyr Asp Ser Lys Pro Trp Ile Gln Val
65                  70                  75                  80

Asn Leu Leu Arg Lys Met Arg Val Ser Gly Val Met Thr Gln Gly Ala
                85                  90                  95

Ser Arg Ala Gly Arg Ala Glu Tyr Leu Lys Thr Phe Lys Val Ala Tyr
            100                 105                 110

Ser Leu Asp Gly Arg Lys Phe Glu Phe Ile Gln Asp Glu Ser Gly Gly
        115                 120                 125

Asp Lys Glu Phe Leu Gly Asn Leu Asp Asn Asn Ser Leu Lys Val Asn
    130                 135                 140

Met Phe Asn Pro Thr Leu Glu Ala Gln Tyr Ile Lys Leu Tyr Pro Val
145                 150                 155                 160

Ser Cys His Arg Gly Cys Thr Leu Arg Phe Glu Leu Leu Gly Cys Glu
                165                 170                 175

Leu His Gly Cys Ser Glu Pro Leu Gly Leu Lys Asn Asn Thr Ile Pro
            180                 185                 190

Asp Ser Gln Met Ser Ala Ser Ser Tyr Lys Thr Trp Asn Leu Arg
        195                 200                 205

Ala Phe Gly Trp Tyr Pro His Leu Gly Arg Leu Asp Asn Gln Gly Lys
    210                 215                 220

Ile Asn Ala Trp Thr Ala Gln Ser Asn Ser Ala Lys Glu Trp Leu Gln
225                 230                 235                 240

Val Asp Leu Gly Thr Gln Arg Gln Val Thr Gly Ile Ile Thr Gln Gly
                245                 250                 255

Ala Arg Asp Phe Gly His Ile Gln Tyr Val Ala Ser Tyr Lys Val Ala
            260                 265                 270

His Ser Asp Asp Gly Val Gln Trp Thr Val Tyr Glu Glu Gln Gly Ser
        275                 280                 285

Ser Lys Val Phe Gln Gly Asn Leu Asp Asn Asn Ser His Lys Lys Asn
    290                 295                 300
```

```
Ile Phe Glu Lys Pro Phe Met Ala Arg Tyr Val Arg Val Leu Pro Val
305                 310                 315                 320

Ser Trp His Asn Arg Ile Thr Leu Arg Leu Glu Leu Leu Gly Cys Phe
            325                 330                 335

Glu Gln Lys Leu Ile Ser Glu Glu Asp Leu Asn Met His Thr Gly
            340                 345                 350

<210> SEQ ID NO 4
<211> LENGTH: 24
<212> TYPE: PRT
<213> ORGANISM: Mus musculus
<220> FEATURE:
<221> NAME/KEY: misc_feature
<222> LOCATION: (1)..(24)
<223> OTHER INFORMATION: leader sequence of mouse lactadherin

<400> SEQUENCE: 4

Met Gln Val Ser Arg Val Leu Ala Ala Leu Cys Gly Met Leu Leu Cys
1               5                   10                  15

Ala Ser Gly Leu Phe Ala Ala Ser
            20

<210> SEQ ID NO 5
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: C1C2 domains of human lactadherin

<400> SEQUENCE: 5

Tyr Ala Gly Asn His Cys Glu Thr Lys Cys Val Glu Pro Leu Gly Met
1               5                   10                  15

Glu Asn Gly Asn Ile Ala Asn Ser Gln Ile Ala Ala Ser Ser Val Arg
            20                  25                  30

Val Thr Phe Leu Gly Leu Gln His Trp Val Pro Glu Leu Ala Arg Leu
        35                  40                  45

Asn Arg Ala Gly Met Val Asn Ala Trp Thr Pro Ser Ser Asn Asp Asp
    50                  55                  60

Asn Pro Trp Ile Gln Val Asn Leu Leu Arg Arg Met Trp Val Thr Gly
65                  70                  75                  80

Val Val Thr Gln Gly Ala Ser Arg Leu Ala Ser His Glu Tyr Leu Lys
                85                  90                  95

Ala Phe Lys Val Ala Tyr Ser Leu Asn Gly His Glu Phe Asp Phe Ile
            100                 105                 110

His Asp Val Asn Lys Lys His Lys Glu Phe Val Gly Asn Trp Asn Lys
        115                 120                 125

Asn Ala Val His Val Asn Leu Phe Glu Thr Pro Val Glu Ala Gln Tyr
    130                 135                 140

Val Arg Leu Tyr Pro Thr Ser Cys His Thr Ala Cys Thr Leu Arg Phe
145                 150                 155                 160

Glu Leu Leu Gly Cys Glu Leu Asn Gly Cys Ala Asn Pro Leu Gly Leu
                165                 170                 175

Lys Asn Asn Ser Ile Pro Asp Lys Gln Ile Thr Ala Ser Ser Ser Tyr
            180                 185                 190

Lys Thr Trp Gly Leu His Leu Phe Ser Trp Asn Pro Ser Tyr Ala Arg
        195                 200                 205
```

```
Leu Asp Lys Gln Gly Asn Phe Asn Ala Trp Val Ala Gly Ser Tyr Gly
    210                 215                 220

Asn Asp Gln Trp Leu Gln Val Asp Leu Gly Ser Ser Lys Glu Val Thr
225                 230                 235                 240

Gly Ile Ile Thr Gln Gly Ala Arg Asn Phe Gly Ser Val Gln Phe Val
                245                 250                 255

Ala Ser Tyr Lys Val Ala Tyr Ser Asn Asp Ser Ala Asn Trp Thr Glu
                260                 265                 270

Tyr Gln Asp Pro Arg Thr Gly Ser Ser Lys Ile Phe Pro Gly Asn Trp
            275                 280                 285

Asp Asn His Ser His Lys Lys Asn Leu Phe Glu Thr Pro Ile Leu Ala
    290                 295                 300

Arg Tyr Val Arg Ile Leu Pro Val Ala Trp His Asn Arg Ile Ala Leu
305                 310                 315                 320

Arg Leu Glu Leu Leu Gly Cys
                325

<210> SEQ ID NO 6
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: leader sequence of human lactadherin

<400> SEQUENCE: 6

Tyr Thr Cys Thr Cys Leu Lys Gly
1               5

<210> SEQ ID NO 7
<211> LENGTH: 19
<212> TYPE: DNA
<213> ORGANISM: Artificial Sequence
<220> FEATURE:
<223> OTHER INFORMATION: Synthetic: mature antisense sequence for shRNA
      targeting TRAF6

<400> SEQUENCE: 7
aaactcatcc ctgaatatc                                              19

<210> SEQ ID NO 8
<211> LENGTH: 19
<212> TYPE: DNA
<213> ORGANISM: Artificial Sequence
<220> FEATURE:
<223> OTHER INFORMATION: Synthetic: mature antisense sequence for shRNA
      targeting IRAK4

<400> SEQUENCE: 8
attaccacca acagaaatg                                              19
```